(12) United States Patent
Babakhani et al.

(10) Patent No.: US 12,711,335 B2
(45) Date of Patent: Aug. 18, 2026

(54) METHODS AND SYSTEMS RELATED TO REMOTE MEASURING AND SENSING

(71) Applicant: William Marsh Rice University, Houston, TX (US)

(72) Inventors: Aydin Babakhani, Houston, TX (US); Seyed Mohammad Kazem Pour, Tehran (IR); Mahdi Forghani, Tehran (IR); Yuxiang Sun, Houston, TX (US); Yaswanth Kumar Cherivirala, Houston, TX (US)

(73) Assignee: William Marsh Rice University, Houston, TX (US)

(*) Notice: Subject to any disclaimer, the term of this patent is extended or adjusted under 35 U.S.C. 154(b) by 1041 days.

(21) Appl. No.: 17/682,012

(22) Filed: Feb. 28, 2022

(65) Prior Publication Data

US 2022/0180080 A1 Jun. 9, 2022

Related U.S. Application Data

(63) Continuation of application No. 17/322,532, filed on May 17, 2021, now Pat. No. 11,263,412, which is a (Continued)

(51) Int. Cl.
*G06K 7/10* (2006.01)
*A61B 5/0205* (2006.01)

(Continued)

(52) U.S. Cl.
CPC ........ *G06K 7/10366* (2013.01); *A61B 5/0205* (2013.01); *E21B 41/0085* (2013.01);

(Continued)

(58) Field of Classification Search
CPC ........... G06K 7/10366; G06K 7/10356; G06K 19/0707; G06K 19/0708; G06K 19/0715;

(Continued)

(56) References Cited

U.S. PATENT DOCUMENTS 4,525,873 A * 6/1985 Baues .................. H04B 10/807 398/168
5,631,562 A 5/1997 Cram et al.

(Continued)

FOREIGN PATENT DOCUMENTS

WO 2016108904 A1 7/2016
WO 2016137480 A1 9/2016

(Continued)

OTHER PUBLICATIONS

Warneke et al., Smart Dust: communicating with a cubic-millimeter computer, in Computer, vol. 34, No. 1, pp. 44-51, Jan. 2001, doi: 10.1109/2.895117. (Year: 2001).*

(Continued)

*Primary Examiner* — Peter Radkowski
(74) *Attorney, Agent, or Firm* — Dickinson Wright PLLC; Ross Spencer Garsson

(57) ABSTRACT

Remote measuring and sensing. Some example embodiment related to optical energy harvesting by identification device, such as infrared identification device (IRID devices). Other embodiments relate to RFID device localization using low frequency source signals. Yet still other embodiments related to energy harvesting by RFID in electric fields in both conductive and non-conductive environments.

18 Claims, 27 Drawing Sheets

Related U.S. Application Data continuation of application No. 16/303,060, filed as application No. PCT/US2017/034374 on May 25, 2017, now Pat. No. 11,048,893.

(60) Provisional application No. 62/341,388, filed on May 25, 2016, provisional application No. 62/341,359, filed on May 25, 2016, provisional application No. 62/341,312, filed on May 25, 2016.

(51) Int. Cl.

| | |
|---|---|
| ***E21B 41/00*** | (2006.01) |
| ***E21B 43/267*** | (2006.01) |
| ***E21B 47/005*** | (2012.01) |
| ***E21B 47/13*** | (2012.01) |
| ***E21B 49/00*** | (2006.01) |
| ***G06K 19/07*** | (2006.01) |
| ***G06K 19/077*** | (2006.01) |
| *A61B 5/00* | (2006.01) |
| *G02B 6/12* | (2006.01) |
| *G02B 6/34* | (2006.01) |
| *G02F 1/025* | (2006.01) |
| *G02F 1/21* | (2006.01) |
| *G02F 1/225* | (2006.01) |

(52) U.S. Cl.

CPC .......... *E21B 43/267* (2013.01); *E21B 47/005* (2020.05); *E21B 47/13* (2020.05); *E21B 49/00* (2013.01); *G06K 7/10356* (2013.01); *G06K 19/0707* (2013.01); *G06K 19/0708* (2013.01); *G06K 19/0715* (2013.01); *G06K 19/0716* (2013.01); *G06K 19/0723* (2013.01); *G06K 19/07766* (2013.01); *A61B 5/0028* (2013.01); *A61B 5/0031* (2013.01); *A61B 5/02055* (2013.01); *A61B 5/7225* (2013.01); *A61B 2560/0219* (2013.01); *A61B 2562/0209* (2013.01); *G02B 6/12004* (2013.01); *G02B 6/34* (2013.01); *G02F 1/025* (2013.01); *G02F 1/212* (2021.01); *G02F 1/2257* (2013.01)

(58) Field of Classification Search

CPC ............. G06K 19/0716; G06K 19/072; G06K 19/07766; F21B 47/005; F21B 47/13; A61B 5/0205; A61B 2560/0219; A61B 2562/0209; A61B 5/0028; A61B 5/003; A61B 5/02055; A61B 5/7225; E21B 41/0085; E21B 43/267; E21B 47/005; E21B 47/13; E21B 47/138; E21B 49/00; G02B 6/12004; G02B 6/34; G02F 1/025; G02F 1/212; G02F 1/2257

See application file for complete search history.

(56) References Cited

U.S. PATENT DOCUMENTS 6,094,173 A * 7/2000 Nylander ............. H01Q 1/2216 343/866
6,184,841 B1 * 2/2001 Shober ................... H01Q 21/08 342/44
6,286,762 B1 * 9/2001 Reynolds ............. G06K 7/0008 235/472.01
6,408,943 B1 6/2002 Schultz et al.
6,976,535 B2 12/2005 Aronstam et al.
7,082,993 B2 8/2006 Ayoub et al.
7,089,099 B2 * 8/2006 Shostak ................ B60C 23/005 701/34.3
7,228,900 B2 6/2007 Schultz et al.
7,403,120 B2 * 7/2008 Duron ..................... G01S 13/46 700/214
7,424,911 B2 9/2008 McCarthy et al.
7,475,158 B2 * 1/2009 Ferri ....................... H04L 45/22 709/239
7,602,668 B2 * 10/2009 Liang ...................... E21B 47/26 367/25
7,712,342 B2 * 5/2010 Loughlin ................ E05B 19/00 70/366
8,041,834 B2 * 10/2011 Ferri ....................... H04L 45/02 709/239
8,072,220 B2 12/2011 Dolgin et al.
8,168,570 B2 5/2012 Barron et al.
8,207,827 B2 * 6/2012 Potyrailo ........... G06K 19/0717 324/633
8,222,996 B2 * 7/2012 Smith ................ G06K 19/0723 340/815.87
8,253,417 B2 8/2012 Pisklak et al.
8,269,501 B2 9/2012 Schmidt et al.
8,316,936 B2 * 11/2012 Roddy .................. E21B 47/005 166/253.1
8,397,810 B2 * 3/2013 Verret ................... E21B 47/005 166/250.12
8,494,775 B2 7/2013 Parsche
8,517,275 B2 * 8/2013 Tsuchiya ............ G06K 19/0723 235/487
8,636,063 B2 1/2014 Ravi et al.
8,682,170 B2 * 3/2014 Prucnal .................. H04B 1/109 398/115
8,683,707 B1 4/2014 Horton
8,693,810 B2 * 4/2014 Suarez .................... G02F 2/002 370/278
8,693,910 B2 * 4/2014 Sekihara .............. G03G 15/205 399/69
8,730,044 B2 * 5/2014 Campero ........... G08B 13/2474 340/10.2
8,736,362 B2 * 5/2014 Huang ...................... H03F 3/38 330/10
8,736,425 B2 * 5/2014 Potyrailo ............... G01D 21/00 340/572.1
8,787,752 B2 * 7/2014 Scherer ..................... G01J 3/02 398/118
8,826,972 B2 * 9/2014 Flint ................... E21B 17/0283 166/250.11
8,841,914 B2 9/2014 Qu et al.
8,881,809 B2 * 11/2014 Verret ................... E21B 47/005 166/250.12
8,937,530 B2 * 1/2015 Smith .............. G06K 19/07703 235/385
9,062,539 B2 * 6/2015 Schmidt ................ E21B 47/138
9,063,252 B2 6/2015 Kamal et al.
9,091,144 B2 7/2015 Swanson et al.
9,097,097 B2 8/2015 DiFoggio et al.
9,133,705 B2 * 9/2015 Angeles Boza ........ E21B 47/12
9,187,993 B2 11/2015 Schmidt et al.
9,201,157 B2 * 12/2015 Mohamadi ............ E21B 43/267
9,208,365 B2 * 12/2015 Nikitin ................. G07B 15/063
9,394,756 B2 * 7/2016 Roberson ................ E21B 47/10
9,394,785 B2 * 7/2016 Goodwin ............. E21B 47/138
9,494,032 B2 * 11/2016 Roberson ................ E21B 33/13
9,532,118 B2 12/2016 Vuran et al.
9,574,441 B2 * 2/2017 Liu ......................... E21B 47/24
9,589,224 B2 * 3/2017 Patterson ........... G06K 19/0707
9,645,234 B2 * 5/2017 Khan ................. G06K 7/10366
9,822,631 B2 * 11/2017 Ravi ....................... E21B 43/25
9,905,939 B2 * 2/2018 Yamagajo ............. H01Q 21/24
10,048,073 B2 8/2018 Dolgin et al.
10,098,544 B2 * 10/2018 Marcus .................. A61B 5/316
10,287,877 B2 5/2019 Gianchandani et al.
10,349,249 B2 7/2019 Akyildiz et al.
10,415,372 B2 * 9/2019 Roberson .............. E21B 43/267
10,422,214 B2 * 9/2019 Babakhani .............. E21B 47/09
10,704,377 B2 * 7/2020 Barfoot ................. E21B 47/113
10,914,698 B2 * 2/2021 Potyrailo ........... G01N 33/1893
11,048,893 B2 * 6/2021 Babakhani ............ E21B 47/005
11,263,412 B2 * 3/2022 Babakhani ......... G06K 7/10366
2002/0044096 A1 * 4/2002 Chung ............... G08B 13/2462 343/742

(56) References Cited

U.S. PATENT DOCUMENTS

2005/0275532 A1* 12/2005 Ferri ........ H04L 45/02 340/870.11
2006/0017545 A1* 1/2006 Volpi ........ G06K 19/0739 340/10.4
2006/0025897 A1* 2/2006 Shostak ........ G06K 19/0717 701/1
2006/0071790 A1* 4/2006 Duron ........ G06K 17/00 340/572.1
2006/0096343 A1* 5/2006 Loughlin ........ E05B 37/08 70/366
2006/0208579 A1* 9/2006 Hohberger ........ H02K 35/02 310/12.12
2007/0023185 A1* 2/2007 Hall ........ E21B 17/006 166/65.1
2007/0278008 A1 12/2007 Kuckes et al.
2008/0106972 A1* 5/2008 Liang ........ E21B 47/26 367/25
2008/0156886 A1* 7/2008 Tsuchiya ........ G06K 19/07749 235/492
2008/0157972 A1* 7/2008 Duron ........ G01S 13/46 340/572.1
2008/0166095 A1* 7/2008 Popovic ........ G02B 6/107 385/15
2008/0251247 A1* 10/2008 Flint ........ E21B 17/006 166/380
2009/0002151 A1* 1/2009 Ferri ........ H04W 40/246 340/539.1
2009/0166509 A1 7/2009 Kline
2009/0167495 A1* 7/2009 Smith ........ G06K 19/07703 340/10.1
2009/0189739 A1* 7/2009 Wang ........ H04Q 9/00 340/10.1
2009/0211754 A1* 8/2009 Verret ........ E21B 47/138 166/250.12
2011/0012736 A1* 1/2011 Potyrailo ........ G06K 19/0717 340/572.1
2011/0044694 A1* 2/2011 Scherer ........ H03F 3/082 250/341.1
2011/0101996 A1* 5/2011 Potyrailo ........ G01D 21/00 324/655
2011/0163857 A1* 7/2011 August ........ G06K 19/0707 340/10.42
2011/0186290 A1* 8/2011 Roddy ........ E21B 47/138 166/253.1
2012/0050086 A1 3/2012 Ito
2012/0105210 A1* 5/2012 Smith ........ G06K 19/0723 340/10.1
2012/0176227 A1* 7/2012 Nikitin ........ G06K 7/10019 340/10.2
2012/0178653 A1* 7/2012 McClung, III ........ E21B 47/11 977/734
2012/0229207 A1* 9/2012 Huang ........ H03F 3/38 330/124 R
2012/0251031 A1* 10/2012 Suarez ........ H04B 1/525 385/2
2012/0273192 A1* 11/2012 Schmidt ........ E21B 47/138 166/250.1
2012/0294608 A1* 11/2012 Prucnal ........ H04K 3/228 398/39
2012/0323092 A1 12/2012 Jain et al.
2013/0093591 A1* 4/2013 Campero ........ G06K 7/0008 340/572.1
2013/0118733 A1* 5/2013 Kumar ........ E21B 47/26 166/254.2
2013/0175024 A1* 7/2013 Verret ........ E21B 47/11 166/66
2013/0248172 A1* 9/2013 Angeles Boza ........ E21B 47/13 166/278
2013/0328693 A1* 12/2013 Mohamadi ........ E21B 43/267 340/854.6
2014/0111349 A1* 4/2014 Roberson ........ E21B 47/138 235/492
2014/0174732 A1* 6/2014 Goodwin ........ E21B 47/13 166/255.1
2014/0182845 A1* 7/2014 Roberson ........ E21B 47/005 166/250.07
2014/0224472 A1 8/2014 Parsche
2015/0090494 A1* 4/2015 Lazarev ........ E21B 47/13 175/40
2015/0115983 A1* 4/2015 Potyrailo ........ G01N 33/2888 324/693
2015/0123816 A1 5/2015 Breed
2015/0198708 A1* 7/2015 Khan ........ G01S 13/878 342/146
2015/0263190 A1* 9/2015 Knights ........ H01L 31/02327 250/201.1
2015/0330217 A1* 11/2015 Liu ........ E21B 47/24 367/83
2016/0040524 A1* 2/2016 Ravi ........ E21B 33/13 166/253.1
2016/0155040 A1* 6/2016 Patterson ........ G06K 19/0711 235/492
2016/0204518 A1* 7/2016 Yamagajo ........ H01Q 21/24 343/809
2016/0259085 A1 9/2016 Wilson et al.
2016/0262619 A1* 9/2016 Marcus ........ A61B 5/303
2017/0204721 A1* 7/2017 Babakhani ........ E21B 43/267
2017/0254191 A1* 9/2017 Barfoot ........ G01V 3/18
2018/0030824 A1* 2/2018 Roberson ........ E21B 33/14
2019/0180065 A1* 6/2019 Babakhani ........ G06K 19/0723
2021/0326545 A1* 10/2021 Babakhani ........ G06K 19/0723

FOREIGN PATENT DOCUMENTS

WO 2016144347 A1 9/2016
WO 2017205565 A9 11/2017

OTHER PUBLICATIONS

Buettner et al., 2008. RFID sensor networks with the Intel WISP. In Proceedings of the 6th ACM conference on Embedded network sensor systems (SenSys '08). Association for Computing Machinery, New York, NY, USA, 393-394. https://doi.org/10.1145/1460412.1460468 (Year: 2008).*

Liu et al., Optically Powered Energy Source in a Standard CMOS Process for Integration in Smart Dust Applications, in IEEE Journal of the Electron Devices Society, vol. 2, No. 6, pp. 158-163, Nov. 2014, doi: 10.1109/JEDS.2014.2341602 (Year: 2014).*

Kahn et al., 1999. Next century challenges: mobile networking for Smart Dust. In Proceedings of the 5th annual ACM/IEEE international conference on Mobile computing and networking (MobiCom '99). Association for Computing Machinery, New York, NY, USA, 271-278. https://doi.org/10.1145/313451.313558 (Year: 1999).*

Sarioglu et al., An Optically Powered CMOS Tracking System for 3 T Magnetic Resonance Environment, in IEEE Transactions on Biomedical Circuits and Systems, vol. 9, No. 1, pp. 12-20, Feb. 2015, doi: 10.1109/TBCAS.2014.2311474 (Year: 2015).*

Zhu et al., A Customized RFID-Based Sensor System for Intelligent Oilwell, in IEEE Sensors Journal, vol. 16, No. 13, pp. 5426-5432 , Jul. 1, 2016, doi: 10.1109/JSEN.2016.2562681. (Year: 2016).*

Z. Zhang et al., "A WDM silicon photonic transmitter based on Mach-Zehnder modulator with surface-normal optical interface," 2015 IEEE 12th International Conference on Group IV Photonics (GFP), Vancouver, BC, Canada, 2015, pp. 79-80, doi: 10.1109/Group4.2015.7305956. (Year: 2015).*

Chang et al., Optical Analog Self-Interference Cancellation Using Electro-Absorption Modulators, in IEEE Microwave and Wireless Components Letters, vol. 23, No. 2, pp. 99-101, Feb. 2013, doi: 10.1109/LMWC.2013.2240288. (Year: 2013).*

Chen et al., A 30GHz impulse radiator with on-chip antennas for high-resolution 3D imaging, 2015 IEEE Radio and Wireless Symposium (RWS), San Diego, CA, USA, 2015, pp. 32-34, doi: 10.1109/RWS.2015.7129717.A (Year: 2015).*

Sakamoto et al., 10 GHZ, 2.4 ps pulse generation using a single-stage dual-drive Mach-Zehnder modulator, Opt. Lett. 33, 890-892 (2008) (Year: 2008).*

(56) References Cited

OTHER PUBLICATIONS

Sepehrian et al., Multi-stage 20 Gbaud driver in 130 nm CMOS for segmented Mach-Zehnder optical modulators, 2016 IEEE International Symposium on Circuits and Systems (ISCAS), Montreal, QC, Canada, May 25, 2016, pp. 201-204, doi: 10.1109/ISCAS.2016.7527205. (Year: 2016).*
Zhang et al., Self-calibrating measurement of high-speed electro-optic phase modulators based on two-tone modulation, Opt. Lett. 39, 3504-3507 (2014) (Year: 2014).*
Zhang et al., Self-interference cancellation using dual-drive Mach-Zehnder modulator for in-band full-duplex radio-over-fiber system. Opt Express. Dec. 28, 2015;23(26):33205-13. doi: 10.1364/OE.23.033205. PMID: 26831988. (Year: 2015).*
Lasser et al., "Self-interference noise limitations of RFID readers," 2015 IEEE International Conference on RFID (RFID), San Diego, CA, USA, 2015, pp. 145-150, doi: 10.1109/RFID.2015.7113085. (Year: 2015).*
Duval et al., Grating couplers integrated on Mach-Zehnder interferometric biosensors operating in the visible range, in IEEE Photonics Journal, vol. 5, No. 2, pp. 3700108-3700108, Apr. 2013, Art No. 3700108, doi: 10.1109/JPHOT.2013.2251873. (Year: 2013).*
Rosenberg et al., A 25 Gbps silicon microring modulator based on an interleaved junction, Opt. Express 20, 26411-26423 (2012) (Year: 2012).*
Darmawan et al., Nested-ring Mach-Zehnder interferometer in silicon-on-insulator, Proceedings vol. 6996, Silicon Photonics and Photonic Integrated Circuits; 69960P (2008) https://doi.org/10.1117/12.779475 (Year: 2008).*
Agilent Technologies: "Agilent HFBR-0400, HFBR-14xx and HFBR-24xx Series Low Cost, Miniature Fiber Optic Components with ST, SMA, SC and FC Ports Data Sheet," Aug. 11, 2003, pp. 1-25 XP055399503, retrieved from the Internet: URL: http://data.datasheetlib.com/pdf1/64/18/641816/agilent-hewlett-packard-hfbr-1424_a5687861aa.pdf?take+binary [retrieved on Aug. 17, 2017].
Akyildiz, et al., "Wireless underground sensor networks: Research challenges", Science Direct, Ad Hoc Networks 4, 2006, pp. 669-686.
EIA: "Trends in U.S. Oil and Natural Gas Upstream Costs"; Independent Statistics and Analysis Report prepared by U. S. Energy Information Administration (EIA), U.S. Department of Energy; Mar. 2016, 141 pages.
Linear Technology: "LTC1502-3.3 Datasheet," Jan. 1, 1999, pp. 1-8, XP055399496, Retrieved from the Internet: URL:http://cds.linear.com/docs/en/datasheet/15023f.pdf [retrieved on Aug. 17, 2017].
Zao, Ersted, "Cable fault locator TDR-109 for power lines"; Product Sheet; http://fault-locator.com/power-inesreflectometer-tdr-109/; Accessed Dec. 24, 2016; 8 pages; copyright Ersted Zao—TDR Cable Fault Locators; Russian Federation.
International Search Report and Written Opinion mail date Feb. 28, 2018 for international application PCT/US2017/034374 filed May 25, 2017, 22 pages.
International Search Report and Written Opinion mail date Oct. 16, 2017 for international application PCT/US2017/034374 filed May 25, 2017, 19 pages.
International Preliminary report on Patentability mail date Nov. 27, 2018 for international application PCT/US2017/034374 filed May 25, 2017, 12 pages.

* cited by examiner

METHODS AND SYSTEMS RELATED TO REMOTE MEASURING AND SENSING

CROSS-REFERENCE TO RELATED APPLICATIONS

This application is a continuation of U.S. application Ser. No. 17/322,532 filed May 17, 2021 titled "Methods and Systems Related to Remote Measuring and Sensing." The Ser. No. 17/322,532 application is a continuation of U.S. application Ser. No. 16/303,060 filed Nov. 19, 2018 titled "Methods and Systems Related to Remote Measuring and Sensing." The Ser. No. 16/303,060 application is a national phase entry of PCT/US2017/034374 filed May 25, 2017 titled "Methods and Systems Related to Remote Measuring and Sensing." The PCT/US2017/034374 claims the benefit of U.S. Provisional Application No. 62/341,388 filed 25 May 2016 titled "Sensor Tag Based on Optical Energy Harvesting and Data Transmission," and U.S. Provisional Application No. 62/341,312 filed 25 May 2016 titled "3D Localizations of Micro-sensors in Subterranean Formations Using Low-Frequency Magnetic Field Triangulation," and U.S. Provisional Application No. 62/341,359 filed 25 May 2016 titled "Low-Power Temperature Sensor and Electric-Field Charging of Microchip Sensors." All the noted applications are incorporated by reference herein as if reproduced in full below.

GOVERNMENT INTEREST

None

BACKGROUND

Technology surrounding radio frequency identification (RFID) tags, and related devices such as infrared identification (IRID) tags (collectively just ID tags), continues to grow. Two technological areas are the focus of academic research, including how to shrink the overall size of the ID tags, and relatedly how to provide power to the ID tags such that the ID tags can be used in a variety of situations.

Any technological advance which improves these or other technological areas associated with ID tags would provide a competitive advantage in the market place.

SUMMARY

At least some of the various embodiments are directed devices with optical energy harvesting. Example embodiments are an optoelectronic device on a substrate, the optoelectronic device comprising: a photodetector configured to convert optical energy into electrical energy at a first voltage, the optical energy having a wavelength of less than 1.2 microns; a voltage regulator electrically coupled to the photodetector, the voltage regulator configured to convert the electrical energy to a second voltage different than the first voltage; a sensor electrically coupled to the voltage regulator, the sensor configured to create sensor data; and a means for transmitting the sensor data to a reader device, such as by an optical beam or a propagating electromagnetic wave.

In some cases, the optoelectronic device may include: a first waveguide that defines a first end, a second end, and a length between the first end and the second end, the first waveguide has an internal volume of silicon; a first grating coupler optically coupled to the first end of the first waveguide, the first grating coupler having a plurality of ridges parallel to each other, and the ridges transverse to the length of the first slab waveguide; a second grating coupler optically coupled to the second end of the first waveguide, the second grating coupler having a plurality of ridges parallel to each other, and the ridges of the second grating coupler transverse to the length of the first slab waveguide; a modulator disposed between the first and second grating couplers, the modulator configured to modulate optical waves that propagate through the first waveguide using the electrical energy from the photodetector; and a driver circuit electrically coupled to the modulator, the driver circuit configured to selectively change a state of the modulator responsive to data.

In example cases, the photodetector is a photodiode that converts optical energy with a wavelength of about 850 nanometers into electrical energy at a first voltage. And the optoelectronic device includes a voltage regulator electrically coupled to the photodetector and the driver circuit, the voltage regulator configured to convert the electrical energy to a second voltage different than the first voltage.

In example cases the photodetector may be any of the following: a photodiode exposed on an outer surface of the optoelectronic device; a plurality of photodiodes connected in series and exposed on the outer surface of the optoelectronic device; a photodiode optically coupled to the first waveguide.

The modulator of the optoelectronic device may include: a first optical path having a first length and a second optical path having a second length, the second optical path distinct from the first optical path, and the first and second optical paths form a portion of the first waveguide; and a depletion region of a semiconductor junction disposed within the first optical path. The first optical path electrically coupled to the driver circuit. The first optical path and depletion region have a first state in which the first optical path induces a 180 degree phase shift in an optical wave that traverses the first optical path relative to an optical wave that simultaneously traverses the second optical path. The first optical path and depletion region have a second state in which the first path induces 90 degrees or less of phase shift in an optical wave that traverses the first optical path relative to an optical wave that simultaneously traverses the second optical path.

In other cases the modulator of the optoelectronic device may include: a second waveguide that defines a closed path with a length and a silicon internal volume, a first region of the second waveguide evanescently coupled to the first waveguide; and a depletion region of a semiconductor junction disposed at a second region within the closed path of the second slab waveguide, the second region distinct from the first region, and the second region coupled to the driver circuit. The second waveguide and the depletion region are configured to selectively induce a phase shift in an optical wave that traverses the second waveguide.

In other cases the modulator of the optoelectronic device may include a second waveguide that defines a closed path with a length and has a silicon internal volume, a portion of the closed path of the second waveguide evanescently coupled to the first waveguide; a first depletion region within the closed path of the second waveguide, the first depletion region electrically coupled to the driver circuit; a third waveguide that defines a closed path with a length and has a silicon internal volume, a portion of the closed path of the third waveguide evanescently coupled to the first waveguide; a second depletion region within the closed path of the second waveguide, the second depletion region electrically coupled to the driver circuit; a fourth waveguide that defines a closed path with a length and has a silicon internal volume, a portion of the closed path of the fourth slab wave guide evanescently coupled to the first waveguide; and a fourth depletion region within the closed path of the fourth waveguide, the third depletion region electrically coupled to the driver circuit. The first, second and third depletion regions are each configured to selectively induce a phase shift in optical waves that traverse the second third and fourth slap waveguides, respectively. Moreover, the length of the second waveguide is shorter than the length of the third waveguide, and the length of the third waveguide is shorter than the length of the fourth waveguide.

In example cases, the optoelectronic device has a sensor electrically coupled to the driver circuit, the sensor configured to sense a physical parameter in proximity of the optoelectronic device, and to create the data responsive to the physical parameter. The sensor may sense any of a variety of parameters, such as: electrical current through the optoelectronic device; electric field in the area of the optoelectronic device pressure proximate the optoelectronic device; temperature proximate the optoelectronic device; and movement of the optoelectronic device.

In further example cases, the optoelectronic device has a relatively small size. For example, in some cases the optoelectronic device may have a length of 100 microns or less, a width of 100 microns or less, and a thickness of 100 microns or less. In other cases, the optoelectronic device may have a length of 100 microns or less measured parallel to the first slab waveguide, a width of 100 microns or less measured perpendicular to the length and parallel to the substrate, and a thickness of 400 microns or less measured perpendicular to the substrate.

Other example embodiments related to the optoelectronic devices are methods including: receiving a light by a photodetector exposed on an outer surface of the optoelectronic device; generating electrical current from the light; powering a sensor from the electrical current, the sensor creates sensor data based on the electrical current; and wirelessly transmitting the sensor data from the optoelectronic device to a receiving device remote from the optoelectronic device.

In example cases, wirelessly transmitting may include: receiving a first infrared light by an optical coupler defined on an optoelectronic device; receiving a second light by a photodetector exposed on an outer surface of the optoelectronic device; generating electrical current from the second light; coupling the first infrared light to a first waveguide of the optoelectronic device, and propagating the first infrared light along a first portion of the first waveguide; and modulating the first infrared light responsive to data to create modulated infrared light, the modulating using electrical current generated from the second light; propagating the modulated infrared light along a second portion of the waveguide distinct from the first portion; and coupling the modulated infrared light toward out of the first waveguide and towards a receiving device remote from the optoelectronic device.

In some cases, the method of receiving the second light further includes receiving the second light having a wavelength such as: less than 1.2 microns; less than 1.0 microns; and 850 nanometers.

The second light in the example method can be used to electrically power a driver circuit coupled to a modulator that implements the modulation. In some cases the second light the second light has a wavelength of 1.0 micron or less, and the first infrared light has a wavelength of 1.2 microns or greater.

The method of coupling the first infrared light to the waveguide may further include coupling by way of a first optical coupler that comprises a first grating structure. And the method of coupling the modulated infrared light out of the first waveguide may include coupling by way of a second optical coupler that comprises a second grating structure.

Modulating may take any suitable form. In some cases, the modulating may be by way of a Mach-Zehnder modulator disposed within the optical path of the first waveguide. In other cases, the modeling may be by an optical ring modulator having a first closed path. And in some cases the optical ring modulator may have a plurality of closed paths.

The method related to the optoelectronic device may further include, prior to modulating: sensing a physical parameter by way of a sensor of the optoelectronic device; and creating the data based on the physical parameter. The sensing may be any suitable parameter, such as: electrical current through the optoelectronic device; pressure proximate to the optoelectronic device; temperature proximate to the optoelectronic device; and movement of the optoelectronic device.

Other example embodiments are directed methods and related systems of RFID device localization. Example methods of locating an RFID device include: pumping the RFID device into a target volume, the target volume comprising materials of heterogeneous dielectric constant greater than one; generating a first source signal at a first location outside the target volume, the first source signal is electromagnetic having a first frequency, and the first source signal propagates into the target volume; generating a second source signal at a second location, the second source signal is electromagnetic having a second frequency different than the first frequency, and the second source signal propagates into the target volume; generating a third source signal at a third location outside the volume, the third source signal is electromagnetic having a third frequency different than the first and second frequencies, and the third source signal propagates into the target volume; receiving the first through third source signals by the RFID device at a location within the target volume, and recording data within the RFID device regarding amplitude of each of the first through third source signals; returning the RFID device to a location outside the volume; reading the data regarding amplitude of the first through third source signals; and determining the location of the RFID device within the target volume.

Receiving the source signals and recording data in the example method may include recording values indicative of amplitude of magnetic field for each of the first through third source signals.

Receiving the source signals and recording the data may further include: receiving a combined signal by way of an inductor defined on the RFID device; filtering the combined signal to extract values indicative of amplitude of the first signal source and storing the values indicative of amplitude from the first signal source; filtering the combined signal to extract values indicative of amplitude of the second source signal and storing the values indicative of amplitude from the second signal source; and filtering the combined signal to extract values indicative of amplitude if the third source signal and storing the values indicative of amplitude from the third source signal.

The filtering in some example methods may further include filtering in an analog domain. The filtering in other example methods may further include converting the combined signal from an analog domain to a digital domain, filtering in the digital domain.

In further example methods pumping the RFID device into the target volume further includes pumping the RFID device entrained in fluid into an underground formation that contains hydrocarbons.

In further example methods related to the RFID device, generating the first source signal at a first location outside the target volume may include generating the first source signal at the first location on the Earth's surface above the underground formation. Generating the second source signal may include generating the second source signal at the second location beneath the Earth's surface within a borehole.

In yet still other example cases reading the data regarding the amplitude of the first through third source signals further includes: enabling a portion of the fluid to flow back to the Earth's surface, the RFID device entrained in the fluid; and reading the RFID device with an interrogating signal as the RFID device passes a reader device.

Reading the RFID with the interrogating signal may further include interrogating the RFID device with the interrogating signal being an electromagnetic signal with a frequency above 1 Megahertz.

In example cases the first through third frequencies are each at least one selected from a group such as: less than 1 Megahertz (MHz); and below 500 Kilohertz (KHz).

In further example cases, the methods may include measuring a property of the target volume contemporaneously with receiving and recording the first through third source signals.

The RFID device of the localization embodiments may include: a substrate that defines an outer perimeter; an inductor of metallic material defined on the substrate, the inductor defines a first lead and a second lead; a first capacitor defined on the substrate, the first capacitor coupled between the first lead and the second lead, the inductor and first capacitor considered together have a resonant frequency below 1000 Megahertz; a first analog-to-digital (AD) converter defined on the substrate, the first AD converted electrically coupled to the inductor; a memory defined on the substrate, the memory electrically coupled to the first AD converter, and the memory configured to store data; and a first antenna defined on the substrate, the first antenna has a resonant frequency above 1 Megahertz. The first AD converter reads values indicative of amplitude of electromagnetic signals read by the inductor, and the RFID device is configured to store the values in the memory. The RFID device is configured to broadcast the values indicative of amplitude responsive to an interrogation signal received by the first antenna.

The RFID device may further include a sensor defined on the substrate, the sensor electrically coupled to the memory, and the sensor configured to read a physical parameter proximate to the RFID device. The RFID device is configured to read the sensor and store a value indicative of the physical parameter in the memory, the read of the sensor and storage of the value indicative of the physical parameter contemporaneous with reading values indicate of amplitude of the electromagnetic signals.

The sensor of the RFID device may any suitable sensor, such as: a temperature sensor; a pressure sensor; a pH sensor; a conductivity sensor.

The inductor of the RFID device may further include a first plurality of loops of strips of metallic material, the first plurality defined a first depth within the RFID device. In some cases, the inductor may further include a second plurality of loops of strips of metallic material defined at a second depth within the RFID device, the second depth different than the first depth, and the second plurality of loops electrically coupled in series with the first plurality of loops.

In example cases, the substrate of the RFID device includes a first edge and a second edge parallel to the first edge, a third edge and a fourth edge parallel to the third edge, and the first through fourth edges define the perimeter. The plurality of loops of wire reside at sides of the substrate proximate the perimeter, and the AD converter, memory, and first antenna reside within the plurality of loops of wire.

The RFID device may further include a second antenna defined on the substrate, the second antenna has a resonant frequency above 1 Megahertz. When the RFID device broadcasts the values indicative of amplitude, the RFID device is configured to broadcast by way of the second antenna responsive to receiving an interrogating signal by way of the first antenna.

The RFID device of these embodiments may further include a digital signal processor defined on the substrate, the digital signal processor electrically coupled to the first AD converter and the memory. The digital signal processor reads values indicative of amplitude of electromagnetic signals received by the inductor and first capacitor from the first AD converter, bandpass filters the values indicative of amplitude, and stores values indicative of amplitude of electromagnetic signals for a plurality of frequencies.

The RFID device may further include: a first analog filter defined on the substrate and electrically disposed between the inductor and the first AD converter, the first analog filter has first center frequency; a second AD converter defined on the substrate, the second AD converter electrically coupled to the inductor and the memory; a second analog filter defined on the substrate and electrically disposed between the inductor and the second AD converter, the second analog filter has a second center frequency different than the first center frequency; a third AD converter defined on the substrate, the third AD converter electrically coupled to the inductor and the memory; a third analog filter defined on the substrate and electrically disposed between the inductor and the third AD converter, the third analog filter has a third center frequency different than the first and second center frequencies. The second AD converter is configured to read values indicative of amplitude of electromagnetic signals read by the inductor and first capacitor, and the RFID device is configured to store the values in the memory. The third AD converter is configured to read values indicative of amplitude of electromagnetic signals read by the inductor and first capacitor, and the RFID device is configured to store the values in the memory.

In some cases, the largest external dimension of the RFID device is 1000 microns or less. And in example cases the memory of the RFID device is non-volatile memory.

Yet sill other embodiments are directed to electric field charging of RFID chips. Example methods include: applying an electric field across a sample volume, a first RFID chip disposed within the sample volume; extracting energy responsive to the electric field by the first RFID chip, the extracting by a first electrode of the first RFID chip and a second electrode of the first RFID chip, and the extracting creates extracted energy; and sensing a parameter associated with the sample volume by the first RFID chip, the sensing utilizing the extracted energy.

Applying the electric field in the example method may include applying the electrical field across the sample volume being a non-conductive environment.

The example method may further include, after sensing, broadcasting the values indicative of the parameter from the first RFID chip by way of a first antenna at a frequency greater than 1 Megahertz.

In some example situations, applying the electric field includes applying the electric field across the sample volume being an underground reservoir containing hydrocarbons. Applying the electric field may also include applying the electric field across a casing of first borehole with respect to a casing of a second borehole, the casing of the second borehole spaced apart from the casing of the first borehole.

In other cases, applying the electric field may include applying the electric field across the sample volume being an annulus between a casing of a borehole and ground, the annulus filled with cement.

The example methods related to electric field charging may further include: extracting energy responsive to the electric field by a second RFID chip, the extracting by a first electrode of the second RFID chip and a second electrode of the second RFID chip; and after sensing by the first RFID chip broadcasting values indicative of the parameter from the first RFID chip by way of a first antenna of the first RFID chip at a frequency greater than 1 Megahertz; and receiving and rebroadcasting the values indicative of the parameter, the rebroadcasting by way of a first antenna of the second RFID chip at a frequency greater than 1 Megahertz, and the receiving and rebroadcasting using energy from the extracting step by the second RFID chip.

Applying the electric field in the example method may alternatively include applying the electrical field across the sample volume being a conductive environment. Extracting energy responsive to the electric field by the first RFID chip further in the conductive environment may include extracting based on flow of electrons through the conductive environment.

In some cases, applying the electric field further includes applying the electric field across the sample volume being a volume of organic tissue.

The example methods in the conductive environment may further include, after sensing the parameter associated with the sample volume, transmitting a value indicative of the parameter by inducing electrical current flow between two electrodes defined on the first RFID chip. Inducing electrical current flow on two electrodes may further include inducing across a third electrode a fourth electrode, the third and fourth electrodes distinct from the first and second electrode, and the inducing using the extracted energy.

In further example embodiments, inducing electrical current flow on two electrodes may further include: storing the extracted energy on the first RFID chip; ceasing extraction of energy by the first electrode and second electrode; and then inducing the electrical current flow between the first electrode and second electrode.

Electric field charging of RFID chips may also include novel RFID chips. Such RFID chips may include: a substrate, the substrate defines a thickness, length, and width; a memory defined on the substrate; a sensor defined on the substrate, the sensor electrically coupled to the memory, and the sensor configured to read a physical parameter proximate to the RFID chip; a first electrode defined on the substrate; a second electrode defined on the substrate, the second electrode disposed at a distance from the first electrode, the distance being at least the half the width; and a power management unit defined on the substrate, the power management unit electrically coupled to the first electrode and the second electrode, the power management unit configured to extract energy based on interaction of the first and second electrode with an electric field external to the RFID chip. The RFID chip is configured read the physical parameter and store a value indicative of the physical parameter in the memory using energy extracted based on interaction of the first and second electrode with the electric field external to the RFID chip.

The sensor of the RFID chips may take any suitable form, such as: a temperature sensor; a pressure sensor; a pH sensor; a conductivity sensor.

The RFID chips may further include: a first antenna (e.g., a dipole antenna) defined on the substrate, the first antenna has a resonant frequency above 1 Gigahertz, and the first antenna distinct from the first and second electrodes; and a transmission controller defined on the substrate, the transmission controller electrically coupled to the first antenna, the memory, and the power management unit, the transmission controller configured to broadcast the value indicative of the physical parameter in the memory, the broadcast by way of the first antenna.

The RFID chips may further include: a first antenna (e.g., a dipole antenna) defined on the substrate, the first antenna has a resonant frequency above about 1 Gigahertz, and the first distinct from first and second electrodes; a second antenna (e.g., a dipole antenna) defined on the substrate, the second antenna has a resonant frequency above about 2 Gigahertz, and the first antenna distinct from the first and second electrodes; and a transmission controller on the substrate, the transmission controller electrically coupled to the first antenna, the second antenna, the memory, and the power management unit, the transmission controller configured to broadcast the value indicative of the physical parameter in the memory, the broadcast by way of the first antenna, and the broadcast responsive to a signal received by the second antenna.

The sensor of the RFID chips may further include: a ring oscillator, the ring oscillator comprising a plurality of NOT gates connected in series; a frequency-to-digital (FD) converter, the FD converter coupled to the ring oscillator and the memory. At least one NOT gate of the ring oscillator may include: a first transistor coupled between a power source a p-channel MOSFET; a second transistor coupled between the p-channel MOSFET and an n-channel MOSFET; an output port of the at least on NOT gate coupled to the gates of the p-channel and the n-channel MOSFETs.

BRIEF DESCRIPTION OF THE DRAWINGS

For a detailed description of example embodiments, reference will now be made to the accompanying drawings (not necessarily to scale) in which.

DEFINITIONS

Figure 1:
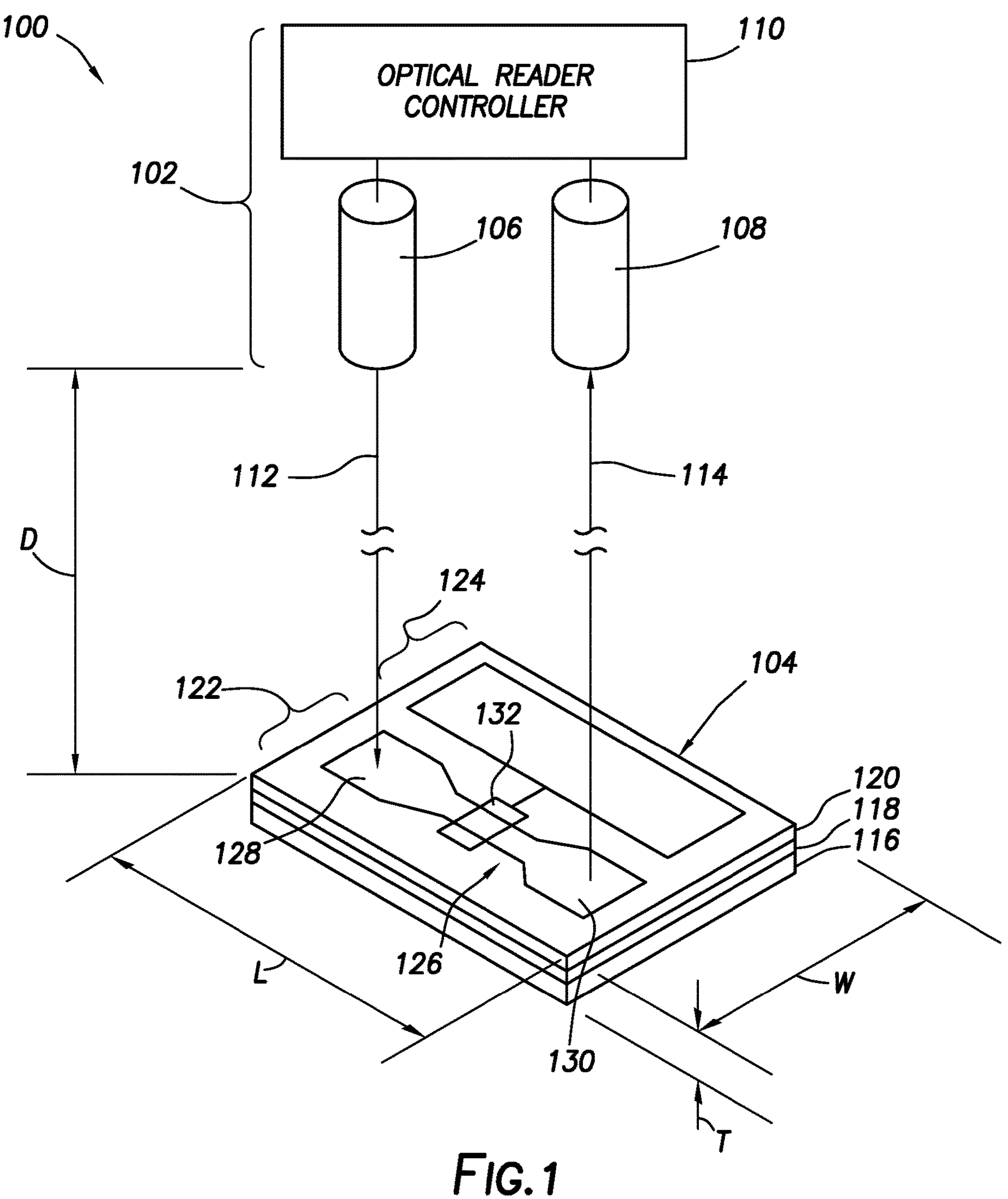
FIG. 1 shows a system in accordance with at least some embodiments.

Various terms are used to refer to particular system components. Different companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or a direct connection. Thus, if a first device couples to a second device, that connection may be through a direct connection or through an indirect connection via other devices and connections.

"About" in reference to a recited value (e.g., length, width, thickness, wavelength) shall mean a range of values centered at the recited value and +/−10% of the recited value.

"Mach-Zehnder modulator" shall mean an optical system where incoming light is split into a first path and a distinct second path, the phase of the light traveling along the first path is selectively changed, and then the light from the first and second paths are combined resulting in constructive or destructive interference.

"Optical ring modulator" shall mean an optical system where light traveling along a primary waveguide is evanescently coupled to a secondary waveguide that defines a closed path. A portion of the light travels around the closed path of the secondary waveguide, and then constructively or destructively interferes with light traveling in the primary waveguide at the location of evanescent coupling.

"Electromagnetic" regarding a source signal shall mean the source signal is at least one selected from the group comprising: an electric field; a magnetic field; and a combined electric field and magnetic field.

"Sample volume" shall mean a volume comprising constituent components, and the average density across the volume is greater than air at standard temperature and pressure.

"Non-conductive environment" shall mean an environment having electrical conductivity less than 10.0 milli-Siemens/meter.

"Conductive environment" shall mean an environment having electrical conductivity of 10.0 milli-Siemens/meter or greater.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Optoelectronic Device

Various embodiments are directed to a mixed optical and electrical system for remote tagging and/or remote measurement of physical parameters. More specifically, various embodiments are directed to optically activating passive optoelectronic devices, and receiving return optical signals modulated with data by the optoelectronic devices. Because the optoelectronic devices are remotely activated using optical energy, the activation and reading of optoelectronic devices may occur over distances of a kilometer or more. Moreover, because the example optoelectronic devices return data in the form of modulated optical energy, the optoelectronic devices may be significantly smaller than radio frequency identification (RFID) devices whose size is limited by receiving and/or transmitting antennas on the chip. In some of the various embodiments, the optoelectronic devices can be constructed as integrated circuits without contact pads, and thus may have dimensions on the order of 100 microns or smaller.

FIG. 1 shows a system 100 in accordance with at least some embodiments. In particular, the system 100 comprises an optical reader 102 optically coupled to an optoelectronic device 104. As shown, the optical reader 102 is remote from the optoelectronic device 104 by a distance D, which distance D may be on the order of a few meters to a kilometer or more. Although the optical reader 102 is shown to be directly above the optoelectronic device 104, the precise relationship shown in the figure is not required and the optical reader may be positioned at substantially any location facing the various optical components that are exposed on one face of the optoelectronic device 104. The sizes of the optical reader 102 and the optoelectronic device 104 of FIG. 1 are not to scale, and in fact the optoelectronic device 104 may have a length L and width W (described more fully below) of 100 microns or less.

The optical reader 102 comprises an optical source 106, an optical receiver 108, and an optical reader controller 110. The optical reader controller 110 operationally couples to both the optical source 106 and the optical receiver 108. On command of the optical reader controller 110, the optical source 106 generates infrared light 112 that is incident upon or shined on the optoelectronic device 104. The infrared light 112 is shown as a line so as not to unduly complicate the figure, but in practice the infrared light will be a beam of optical waves at infrared wavelengths. In example systems, the optical source 106 is a laser that produces the infrared light (i.e., electromagnetic waves with wavelengths of around 1 or 2 microns). Based on structures of the optoelectronic device 104 discussed more below, the optoelectronic device 104 receives the infrared light 112, modulates the infrared light with data (e.g., sensor data or an identification number), and returns infrared light as modulated infrared light 114 to optical receiver 108 of the optical reader 102. The optical reader 102, specifically the optical reader controller 110, decodes the data from the modulated infrared light 114, and passes the decoded data to other devices.

In accordance with example embodiments, the optoelectronic device 104 is constructed using complementary metal oxide semiconductor (CMOS) processes; and more particularly, the example optoelectronic device 104 comprises a silicon-on-insulator (SOI) construction. Thus, the optoelectronic device comprises a substrate 116 (e.g., silicon) covered by insulation layer 118 (e.g., oxide layer), and an active area 120. The relative thicknesses of the layers are not shown to scale in the figure. Nevertheless, in example systems the substrate 116 may have a thickness of about 300 microns, the insulation layer 118 may have a thickness of about 1 micron, and the active area 120 may have a thickness of about 10 to 100 nanometers depending on specific design criteria for the device. Thus, the optoelectronic device 104 may have a thickness T of 400 microns or less (measured perpendicular to the substrate 116). In some cases, the optoelectronic device 104 may have a thickness T of about 320 microns or less. Further in example systems, the optoelectronic device may have a length L of 100 microns or less, and a width W of 100 microns or less, as L and W are depicted in FIG. 1 (i.e., measured in a plane parallel to the substrate 116).

The optoelectronic device 104 may be conceptually divided into optical components 122 and electrical components 124. The division into optical components 122 and electrical components 124 is merely conceptual to help organize the explanation of the overall device, and as discussed more below the various optical and electrical components coexist in some areas (e.g., the modulator) to implement the overall functionality. Conceptually then, the infrared light 112 is incident upon the optical components 122. A portion of the infrared light is coupled into a primary waveguide 126 by way of the optical coupler 128, and the infrared light then propagates along the primary waveguide 126 toward optical coupler 130. The primary waveguide 126 is associated with a modulator 132 that is configured to modulate infrared light traveling along the primary waveguide 126 (i.e., the modulator 132 modulates optical waves that propagate through the primary waveguide 126). The modulation is based on data received from the electrical components 124, and the data could be based on any of a variety of information discussed more below. The modulator 132 thus creates modulated infrared light that propagates along the primary waveguide 126 toward the optical coupler 130. When the modulated infrared light encounters the optical coupler 130, the modulated infrared light is coupled out of the primary waveguide 126, and in the example systems is directed back toward the optical receiver 108 in the form of modulated infrared light 114.

Figure 2:
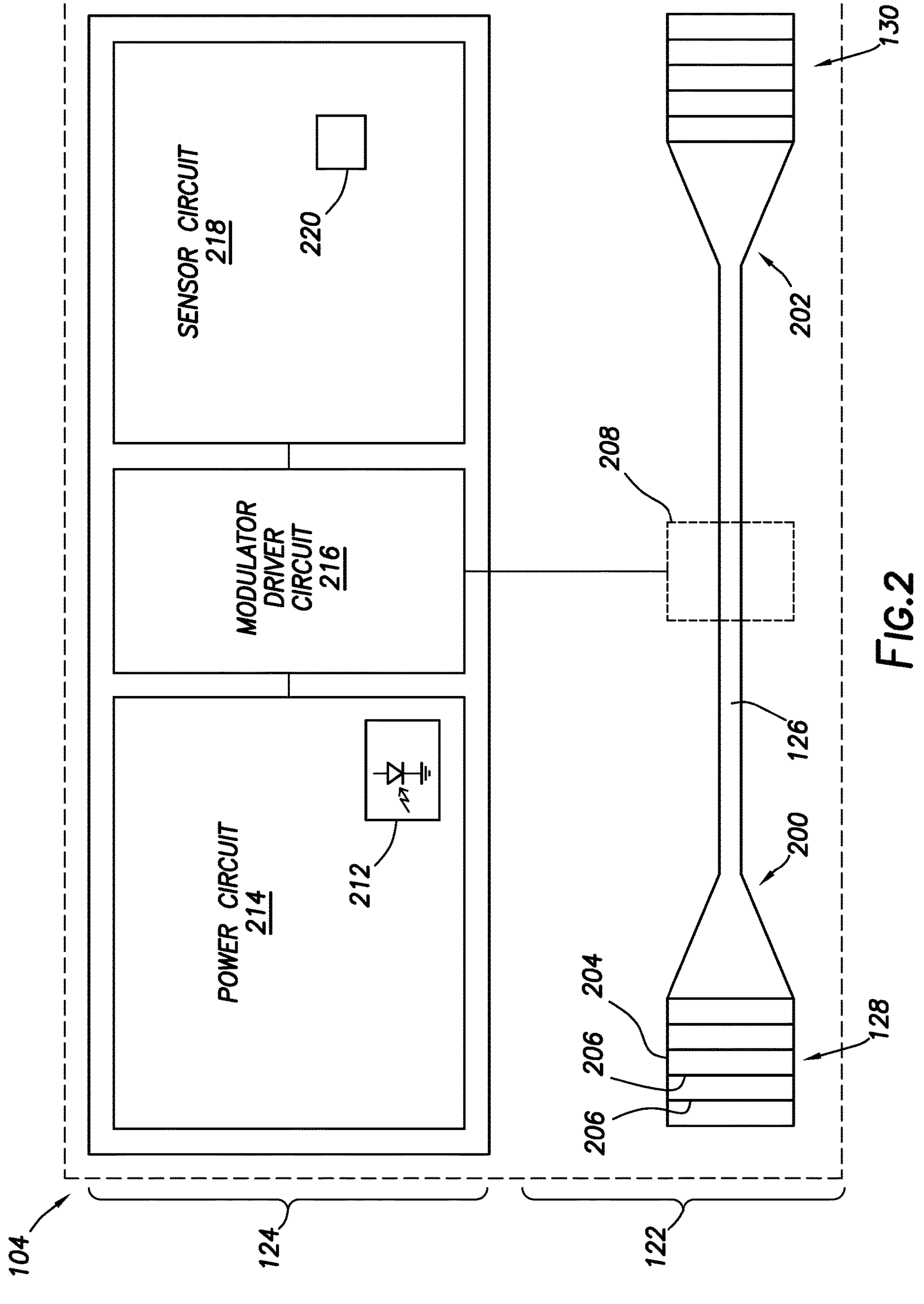
FIG. 2 shows a block diagram of an optoelectronic device 104 in accordance with at least some embodiments.

FIG. 2 shows a block diagram of the optoelectronic device 104 in accordance with example systems. In particular, visible in FIG. 1 are the conceptual optical components 122 and electrical components 124. Focusing initially on the optical components 122, better shown in FIG. 2 is the primary waveguide 126. The primary waveguide 126 defines a first end 200 and the second end 202 opposite the first end 200. The primary waveguide defines a length between the first end 200 and the second end 202. In example systems, the primary waveguide 126 is made of silicon with oxide layers along the outer surfaces of the silicon. Thus, the primary waveguide 126 has an internal volume of silicon through which infrared light propagates in one or more resonant modes.

On the first end 200 of the primary waveguide 126 resides optical coupler 128. Optical coupler 128 is optically coupled to the primary waveguide 126 such that at least some infrared light incident upon optical coupler 128 is coupled into the primary waveguide 126. In the example system, the optical coupler 128 is shown as a grating structure or grating coupler 204 having a plurality of ridges 206 that are parallel to each other, and the plurality of ridges 206 are transverse to the length of the primary waveguide 126. As specifically shown, the plurality of ridges 206 are perpendicular to the length of the primary waveguide 126, but any grating arrangement that couples incident infrared light into the primary waveguide may be used (e.g., parallel but semicircular ridges that focus reflected/refracted infrared light into the primary waveguide 126). Moreover, while the plurality of ridges 206 are shown equally spaced, any suitable arrangement of the ridges may be used (e.g., apodized grated to reduce parasitic escape of infrared light out of the optical coupler 128 before reaching the primary waveguide 126).

Still referring to FIG. 2, on the second end 202 of the primary waveguide 126 resides optical coupler 130. Optical coupler 130 is optically coupled to the primary waveguide 126 such that infrared light propagating toward the optical coupler 130 (e.g., modulated infrared light) is coupled out of the primary waveguide 126 into air or free space. In the example system, the optical coupler 130 is shown to have a similar structure as grating coupler 204 having a plurality of ridges (the grating coupler of optical coupler 130 not specifically numbered); however, any grating arrangement that couples infrared light within the primary waveguide 126 into air or free space may be used. Moreover, the grating structure as between the optical coupler 128 and the optical coupler 130 need not be the same. For example, the optical coupler 128 may have a grating structure tuned for receiving infrared light (e.g., apodized grating designed for higher performance of inbound infrared light), and the optical coupler 130 may have a grating structure tuned for coupling optical energy out of the primary waveguide 126 (e.g., apodized grating designed for higher performance of outbound infrared light).

The example optoelectronic device 104 further comprises a modulator 208 disposed between the first end 200 and the second end 202 of the primary waveguide 126. In the example system, the modulator is centered between the first end 200 and second end 202, and the modulator 208 has a depicted size, but any suitable size and location along the primary waveguide 126 may be used. The modulator 208 is configured to modulate optical waves or optical energy in the form of infrared light propagating through the primary waveguide 126. More particularly, the modulator 208 is configured to modulate the infrared light propagating through the primary waveguide 126 responsive to data. The modulator 208 may take any suitable form, such as a Mach-Zehnder modulator or an optical-ring modulator, as discussed more below.

In accordance with example embodiments, the optoelectronic device 104 comprises a photodetector 212 (e.g., a photodiode) that harvests optical energy (e.g., ambient optical energy) to produce electrical power for the various electrical components 124. In the example system, the photodetector 212 is located in power circuit 214. In another example arrangement the photodetector 212 may be positioned in close proximity to the optical coupler 128 and/or the primary waveguide 126 (e.g., the grating coupler 204 may be disposed on an outer surface of the optoelectronic device 104, and the photodetector 212 may be positioned beneath the grating coupler 204 to harvest optical energy from ambient light that is not coupled into the primary waveguide 126). In yet still other cases, the photodetector 212 may be exposed on an outer surface of the optoelectronic device 104 as shown such that ambient light may be received directly by the photodetector 212.

The electrical components 124 may be conceptually divided into a power circuit 214, a modular driver circuit 216 (hereafter just driver circuit 216), and a sensor circuit 218. The conceptual division into the three circuits is merely to aid in organizing and describing the various structures and functions, but does not necessarily denote any physical relationships in the operational optoelectronic device 104. As the name implies, the power circuit 214 is configured to receive optical energy harvested by the photodetector 212, and create from the harvested optical energy various supply voltages and clock signals used by the driver circuit 216 and/or the sensor circuit 218. Example power circuits are discussed in greater detail below.

Sensor circuit 218 may include a sensor 220, and the sensor circuit 218 and/or sensor 220 are configured to sense a physical parameter in proximity of the optoelectronic device 104. The sensor circuit 218 and/or sensor 220 may thus directly or indirectly create data that are provided to the driver circuit 216 to be used in the modulation of the infrared light propagating along the primary waveguide 126. Any suitable parameter that can be measured by a sensor 220 constructed monolithically with the remaining components may be used. As an example, the sensor circuit 218 and/or sensor 220 may measure: electrical current through the optoelectronic device (e.g., if the optoelectronic device is in a conductive medium); electric field in the area of the optoelectronic device 104 (e.g., voltage across the sensor 220 in the form of two spaced apart electrodes); pressure proximate the optoelectronic device; temperature proximate the optoelectronic device; and movement of the optoelectronic device (e.g., seismic vibrations). Other physical parameters are possible and thus the list shall not be read to be limiting.

The driver circuit 216 is electrically coupled to the power circuit 214, the sensor circuit 218, and the modulator 208. Using power from the power circuit 214, and the data provided by the sensor circuit 218, the driver circuit 216 operates modulator 208 to modulate the infrared light propagating within the primary waveguide 126 responsive to the data such that optical reader 102 (FIG. 1) can decode and utilize the data. The specification now describes various embodiments of the modulator 208.

Figure 3:
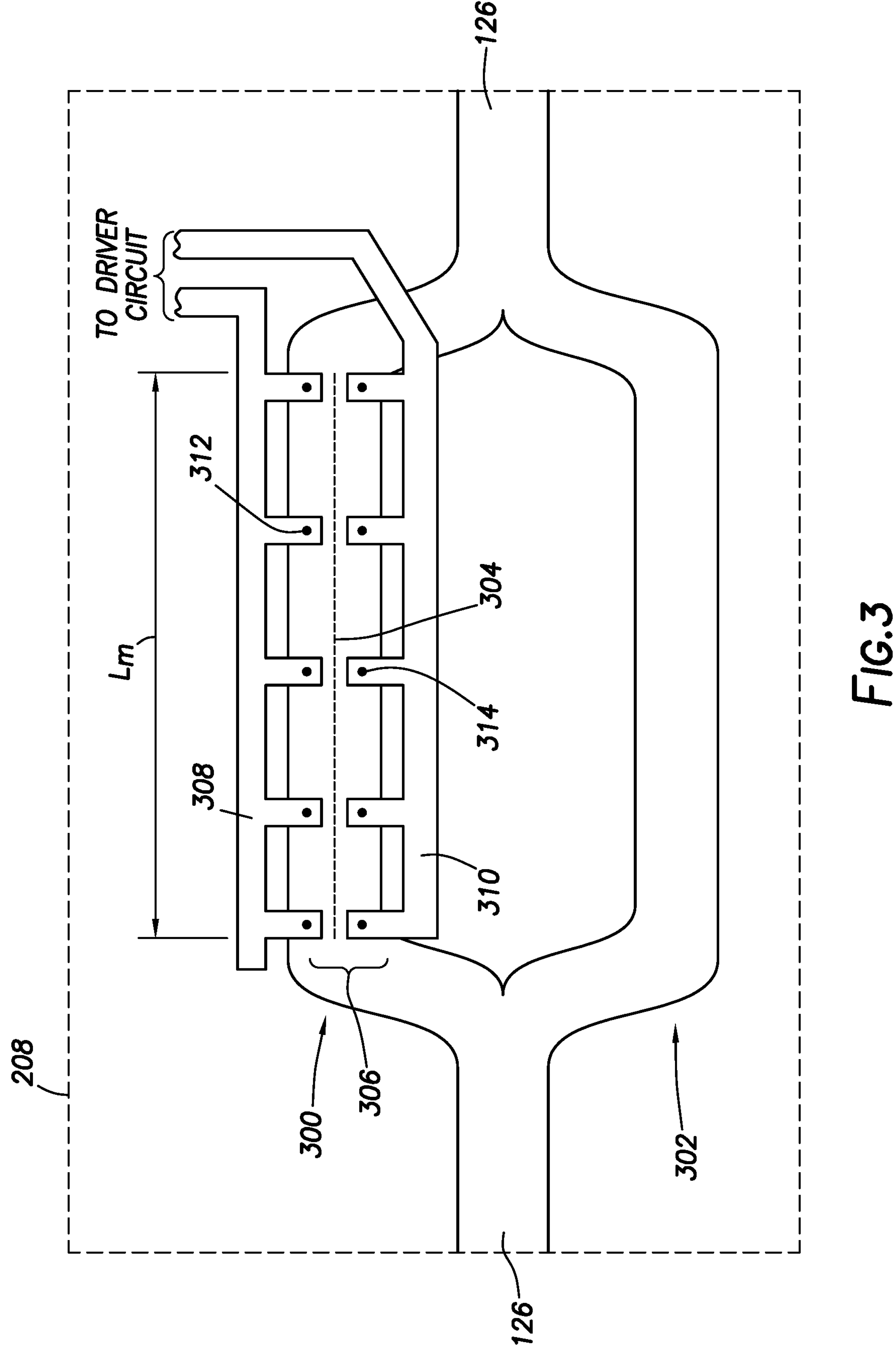
FIG. 3 shows an overhead view of a modulator in accordance at least some embodiments.

FIG. 3 shows an overhead view of a modulator 208 of the optoelectronic device 104 in accordance with example embodiments where the modulator is a Mach-Zehnder modulator. In particular, the modulator 208 of FIG. 3 comprises a first optical path 300 that has length Lm, and the modulator 208 further comprises a second optical path 302 distinct from the first optical path 300, the second optical path 302 also has length Lm. Thus, in the example systems the lengths of the first optical path 300 and the second optical path 302 are the same, and the precise locations at which the lengths are measured is irrelevant so long as consistent positions are used. As shown, the first and second optical paths 300 and 302 can be considered a portion of the primary waveguide 126. Each of the first and second optical paths are waveguides constructed of the same material as the primary waveguide 126, and thus each optical path 300 and 302 has silicon internal volume.

The optical path 300 comprises a semiconductor junction as shown by dashed line 304. The semiconductor junction 304 is created by differences in doping as between the silicon on one side of the junction (e.g., a P-type doping) and the silicon on the other side of the junction (e.g., N-type doping). The drawing does not show the extent of the doping on each side of the semiconductor junction 304 so as not to unduly complicate the figure, but the extent of the doping may be limited to be within the optical path 300 or beyond the optical path 300. Although the semiconductor junction is shown as a straight line centered within the optical path 300, using various masking techniques the semiconductor junction can take any suitable form (e.g., triangular saw tooth, square saw tooth, sinusoidal), and particularly for the non-linear semiconductor junctions need not reside fully within the optical path 300. The presence of the semiconductor junction 304 creates a depletion region 306 that spans at least a portion of the optical path 300.

Each side of the semiconductor junction is separately electrically coupled to the driver circuit 216 (FIG. 2). In the example system, the optical paths are covered with an insulation layer (not specifically shown), and created over the insulation layer are electrical leads 308 and 310. Electrical lead 308 is shown to electrically couple to one side of the semiconductor junction 304 by way of a plurality of electrical contacts 312 (only one contacted specifically numbered). Likewise, electrical lead 310 is shown to electrically couple to the opposite side of the semiconductor junction 304 by way of a plurality of electrical contacts 314 (only one contact specifically numbered). Any number of electrical contacts may be used, and any other suitable spacing as between the electrical contacts of the electrical leads 308 and 310 may be used (e.g., the contacts need not be at same longitudinal locations along the optical path).

As shown, the electrical leads 308 and 310 electrically couple to the driver circuit 216 (FIG. 2). By controlling the voltage across the semiconductor junction 304 (e.g., a PN junction), the width of the depletion region 306 may be expanded and contracted. The infrared light propagating through the optical path 300 interacting with the depletion regions causes phase delay of the infrared light, and then the infrared light is combined again with the infrared light that simultaneously propagated through the optical path 302, and during the combination constructive or destructive interference occurs. Although the example modulator 208 may have a range of modulation capability based on the size of the depletion region as controlled by the size of the depletion region 306, in accordance with example embodiments the modulator 208 of FIG. 3 and the driver circuit 216 (FIG. 2) have two distinct modes or states. In a first state the optical path 300 and depletion region 306 induces about a 180 degree phase shift in the infrared light that traverses the optical path 300 relative to infrared light that simultaneously traverses the optical path 302. In the first state, when light from the two optical paths combine there is substantially complete destructive interference. Further, the optical path 300 and depletion region 306 have a second state that induces 90 degrees or less of phase shift in the infrared light that traverses the optical path 300 relative to infrared light that simultaneously traverses the optical path 302. In one example second state, the phase shift induced in the optical path 300 relative to the optical path 302 is 10 degrees or less. In the second state, when light from the two optical paths combine there is constructive interference. Thus, the modulator 208 under command of the driver circuit 216 may be able to effectively create on-off pulses of infrared light as part of modulating the data based on the data from the sensor circuit 218.

Figure 4:
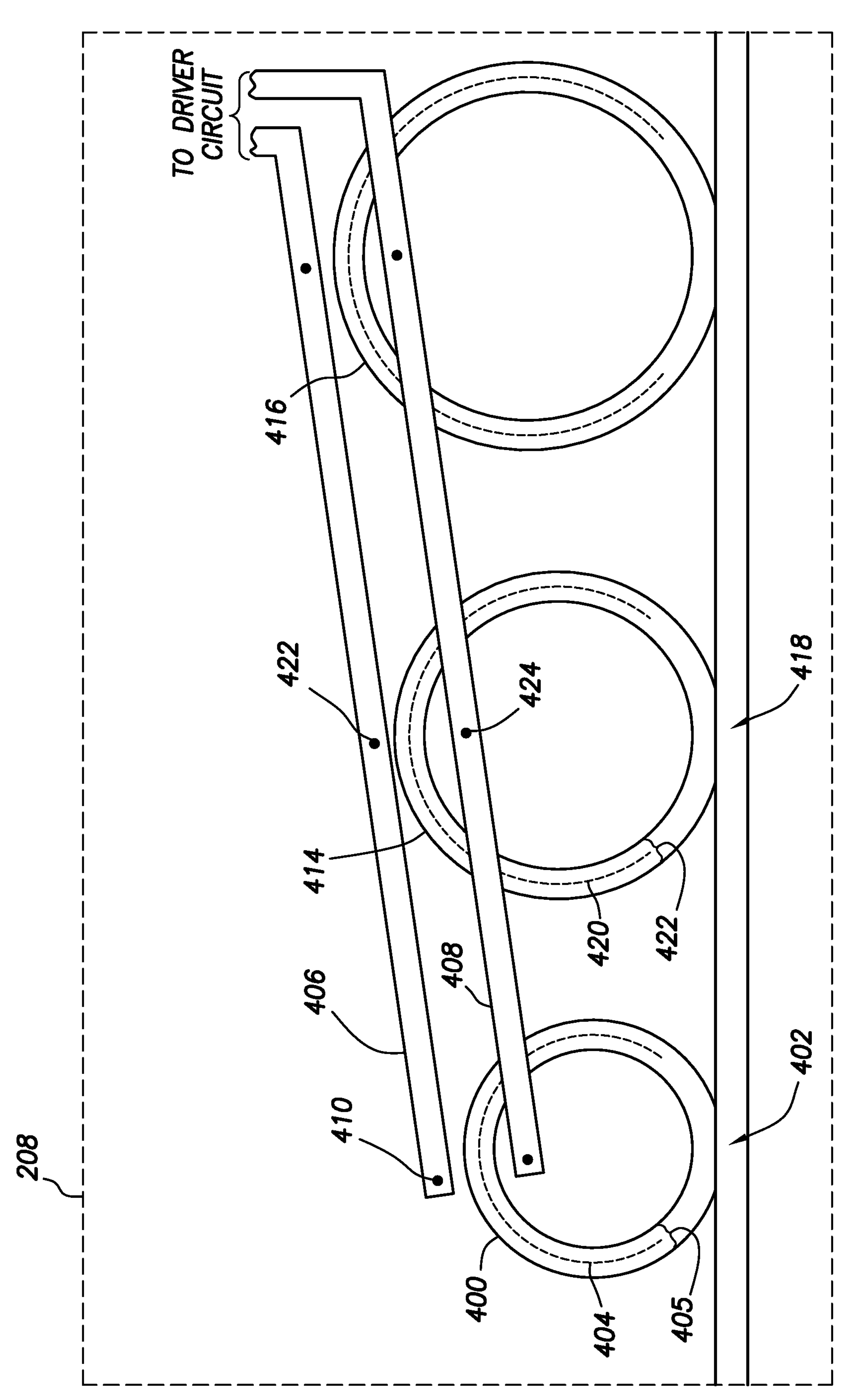
FIG. 4 shows an overhead view of a modulator in accordance with at least some embodiments.

FIG. 4 shows an overhead view of a modulator 208 of the optoelectronic device 104 in accordance with yet still further example embodiments where the modulator is an optical-ring modulator. In particular, the modulator 208 of FIG. 4 comprises a ring waveguide 400 that defines a closed path. The ring waveguide 400 is a waveguide constructed of the same material as the primary waveguide 126, and thus the ring waveguide 400 has silicon internal volume. The ring waveguide has a circular length, the length not specifically delineated in the drawing but may be measured along the center of the waveguide. The ring waveguide 400 has a portion 402 that is disposed proximate the primary waveguide 126, and in particular the ring waveguide 400 is evanescently coupled to the primary waveguide 126 along the portion 402. The ring waveguide 400 comprises a semiconductor junction 404 (shown as a dashed line). The semiconductor junction 404 is created by differences in doping as between the silicon on one side of the junction (e.g., a P-type doping) and the silicon on the other side of the junction (e.g., N-type doping). The extent of the doping is not shown in FIG. 4 so as not to unduly complicate the drawing. Although the semiconductor junction 404 is shown centered within ring waveguide 400, using various masking techniques the semiconductor junction 404 can take any suitable form (e.g., triangular saw tooth, square saw tooth, sinusoidal). The presence of the semiconductor junction 404 creates a depletion region 405 that spans a portion of the ring waveguide 400.

Each side of the semiconductor junction 404 is separately electrically coupled to the driver circuit 216 (FIG. 2). In the example system, ring waveguide 400 may be covered with an insulation layer (not specifically shown), and created over the insulation layer are electrical leads 406 and 408. Electrical lead 406 is shown to electrically couple to one side of the semiconductor junction 404 by way of an electrical contact 410. Likewise, electrical lead 408 is shown to electrically couple to the opposite side of the semiconductor junction 404 by way of electrical contact 412. Any number of electrical contacts may be used to couple to the respective sides of the semiconductor junction 404. As shown, the electrical leads 406 and 408 electrically couple to the driver circuit 216 (FIG. 2). By controlling the voltage across the semiconductor junction 404 (e.g., a PN junction), the width of the depletion region may be expanded and contracted. In operation, infrared light propagating through the primary waveguide 126 interacts with the ring waveguide 400. A portion of the optical energy of the infrared light is transferred into the ring waveguide 400 through the evanescent coupling, while the remaining optical energy continues along the primary waveguide 126. The infrared light propagating around the ring waveguide 400 interacts with the depletion region 405 and causes phase delay, and as the infrared light within the ring waveguide 400 again interacts with the infrared light propagating the primary waveguide 126, constructive or destructive interference occurs by way of the evanescent coupling at portion 402. Although the example modulator 208 may have a range of modulation capability based on the length of the ring waveguide 400 and size of the depletion region as controlled by the voltage applied across the electrical leads 406 and 408, in accordance with example embodiments the ring waveguide 400 of modulator 208 of FIG. 4 and the driver circuit 216 have two distinct modes or states. In a first state the ring waveguide 400 and depletion region 405 induce about a 180 degree phase shift in the infrared light that loops the ring waveguide 400. Further, the ring waveguide and depletion region 405 have a second state that induces 90 degrees or less of phase shift in the infrared light that loops the ring waveguide 400. In one example second state, the phase shift induced in the ring waveguide 400 is 10 degrees or less. Thus, the modulator 208 under command of the driver circuit 216 may be able to create on-off pulses of infrared light as part of modulating the data based on the data from the sensor circuit 218.

In the example modulator 208 of FIG. 4, ring waveguide 400 is illustrated as semi-circular, and where portion 402 is straight. That is, in the example system of FIG. 4 the portion 402 extends parallel to the primary waveguide 126 for a specific distance. In one example system the waveguide structures have thicknesses of 300 nanometers (nm), widths of 600 nm, a coupling gap or distance of 300 nm (i.e., distance between ring waveguide and primary waveguide), and the portion 402 is straight for about 15 microns. The longer evanescent coupling length provides greater time/length over which infrared light within the ring waveguide 400 and infrared light within the primary waveguide 126 to constructively or destructively interact. In other cases, however, the ring waveguide 400 may be circular.

In some cases, a single ring waveguide may be sufficient to modulate the infrared light within the primary waveguide 126. However, in yet still further cases the modulator 208 may comprise a plurality of ring waveguides. In the example system of FIG. 4, the modulator 208 comprises three ring waveguides, being ring waveguide 400, ring waveguide 414, and ring waveguide 416. In particular, the modulator 208 of FIG. 4 comprises a ring waveguide 414 that defines a closed path. The ring waveguide 414 is a waveguide constructed of the same material as the primary waveguide 126, and thus the ring waveguide 414 has silicon internal volume. The ring waveguide has a circular length, the length not specifically delineated in the drawing but may be measured along the center of the ring waveguide 414. The ring waveguide 414 has a portion 418 that is disposed proximate the primary waveguide 126, and in particular the ring waveguide 414 is evanescently coupled to the primary waveguide 126 along the portion 418. Like ring waveguide 400, the portion 418 may be straight to increase the coupling time/distance as between the waveguides. The ring waveguide 414 comprises a semiconductor junction 420 (shown as a dashed line). Although the semiconductor junction 420 is shown centered within ring waveguide 414, using various masking techniques the semiconductor junction 420 can take any suitable form (e.g., triangular saw tooth, square saw tooth, sinusoidal). The presence of the semiconductor junction 420 creates a depletion region 422 that spans a portion of the ring waveguide 414.

Each side of the semiconductor junction 420 is separately electrically coupled to the driver circuit 216 (FIG. 2) by way of electrical leads 406 and 408. That is, electrical lead 406 is shown to electrically couple to one side of the semiconductor junction 420 by way of an electrical contact 424. Likewise, electrical lead 408 is shown to electrically couple to the opposite side of the semiconductor junction 420 by way of electrical contact 424. As before, any number of electrical contacts may be used to couple to the respective sides of the semiconductor junction 420. By controlling the voltage across the semiconductor junction 420 (e.g., a PN junction), the width of the depletion region may be expanded and contracted. In operation, infrared light propagating through the primary waveguide 126 interacts with the ring waveguide 414. A portion of the optical energy of the infrared light is transferred into the ring waveguide 414 through the evanescent coupling, while the remaining optical energy continues along the primary waveguide 126. The interaction infrared light propagating around the ring waveguide 414 and interacting with the depletion region 422 causes phase delay of the infrared light within the ring waveguide, and as the infrared light within the ring waveguide 414 again interacts with the infrared light propagating the primary waveguide 126, constructive or destructive interference occurs by way of the evanescent coupling at portion 402. Although the example modulator 208 may have a range of modulation capability based on the length of the ring waveguides 400 and 414 and size of the respective depletion regions as controlled by the voltage applied across the electrical leads 406 and 408, in accordance with example embodiments the modulator 208 of FIG. 4 and the driver circuit 216 have two distinct modes or states in each ring waveguide 400 and 414, with the overall effect of the modulator 208 that the modulator creates on-off pulses of infrared light in the primary waveguide 126 (e.g., viewed or measured just before the optical coupler 130) as part of modulating the data based on the data from the sensor circuit 218.

Ring waveguide 416, when implemented, operates similarly to ring waveguides 400 and 414, and thus so as not to unduly complicate the discussion, the duplicative description of ring waveguide 416 is omitted. The path lengths of the ring waveguides 400, 414, and 416 are different, though the drawing of FIG. 4 is not necessarily to scale and thus the differences in path length may be exaggerated. Nevertheless, the length of ring waveguide 400 is shorter than the length of ring waveguide 414, and the length of ring waveguide 414 is shorter than the length of ring waveguide 416. The effect of having plurality of ring waveguides is explained in reference to FIG. 5.

Figure 5:
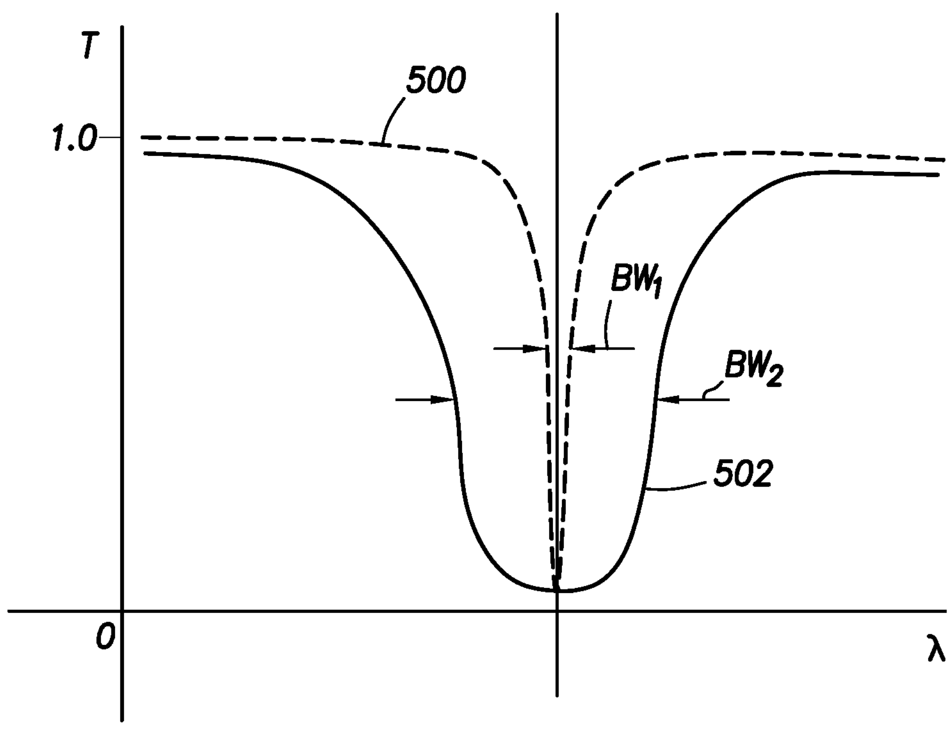
FIG. 5 shows a plot of transmittance through as a function of wavelength in accordance with at least some embodiments.

FIG. 5 shows a plot of transmittance through the modulator 208 as a function of wavelength of the infrared light both the case of a single ring waveguide, and multiple ring waveguides. In particular, the vertical axis of the figure is transmittance, and the horizontal axis is wavelength. In the second state of the modulator, and in the ideal case, the infrared light propagating along the primary waveguide 126 is substantially unaffected by the presence of the modulator, and thus the transmittance is substantially unity regardless of wavelength of the infrared light (the situation not shown in FIG. 5). However, when the driver circuit 216 modulates the size of the depletion region(s) within the example optical-ring modulator, destructive interference occurs, which lowers the transmittance of the modulator 208 as a whole. In the case of a single ring waveguide (e.g., ring waveguide 400), the bandwidth within which the destructive interference occurs may be relatively narrow, as illustrated by dashed line 500 and bandwidth $BW_1$. Although it is contemplated that the optical source 106 (FIG. 1) is a laser that produces a very narrow bandwidth of infrared light, frequency dispersion occurs not only in the propagation of the infrared light 112 through the air to reach the optoelectronic device 104, but frequency dispersion may also occur within the optoelectronic device 104 itself (e.g., propagating along the primary waveguide 126). Thus, destructive interference within the very narrow bandwidth $BW_1$ may "miss" other wavelengths, thus degrading overall modulator 208 performance. Having a plurality of ring waveguides with slightly different closed path lengths and/or slightly different phase delays enables a wider bandwidth within which destructive interference may occur, as shown by solid line 502 and bandwidth $BW_2$. Thus, increasing the number of ring waveguides within a modulator 208 implementing optical-ring modulators may increase overall performance of the modulator 208 and thus enable better performance of the optoelectronic device, such as the ability to read and decode the modulated infrared light 114 (FIG. 1) from greater distances.

The specification now turns to an explanation of a power circuit 214 (of FIG. 2) in accordance with at least some embodiments. The power provided by the power circuit 214 (along the number and types of clock signals and reference voltages) is controlled by the overall design of the optoelectronic device, and thus various components may be omitted or modified to fit the particular design situation. For example, an optoelectronic device implemented purely as a data tag (i.e., no sensor circuit 218) utilizes less power and may need fewer reference voltage signals than an optoelectronic device that has active sensors measuring physical parameters. Nevertheless, in at least some embodiments the optoelectronic device 104 is designed and constructed to operate in power ranges of microwatts and below even in the presence of sensor circuit 218.

Figure 6:
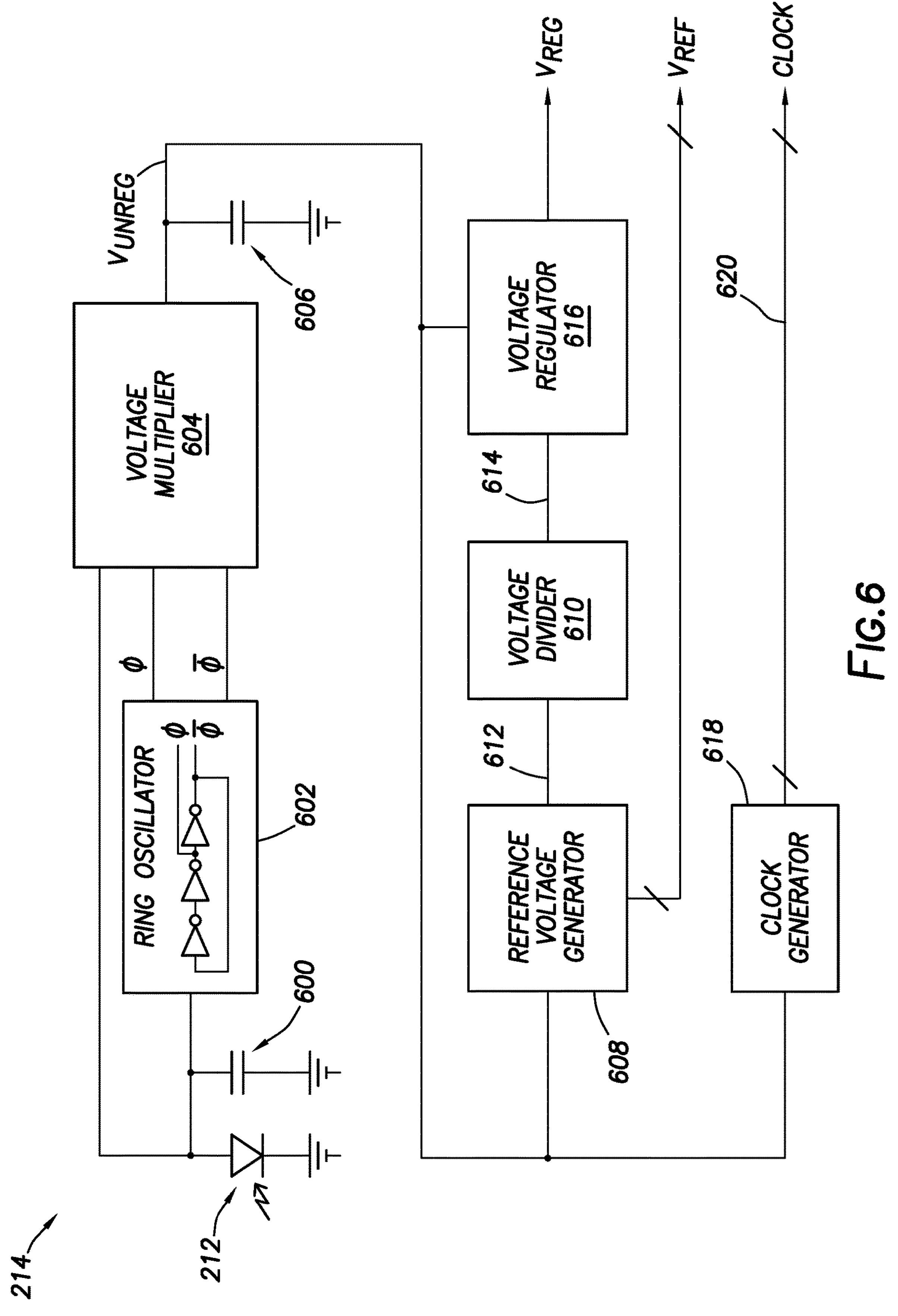
FIG. 6 shows a block diagram of a power circuit in accordance with at least some embodiments.

FIG. 6 shows a block diagram of a power circuit 214 in accordance with at least some embodiments. In particular, the example power circuit comprises photodetector 212 coupled in parallel with an input capacitor 600 to a ring oscillator circuit 602 (hereafter just ring oscillator 602). Ring oscillator 602 creates a pulse stream that is fed to downstream devices. An example logic diagram of a ring oscillator is provided within the box labeled ring oscillator, the example logic diagram in the form of three NOT gates connected in series with a feedback path. When sufficient power is provided from the photodetector 212 (e.g., about 0.7 V), the ring oscillator automatically begins oscillating and thus providing a pulse stream. The example ring oscillator 602 produces two output signals, with one pulse stream being a logical NOT of the other pulse stream (labeled ϕ and ϕ NOT in the figure). Depending on the downstream devices and needs, the logical NOT output may be omitted. By controlling the number of NOT gates connected in series and other parameters, the frequency of the pulse stream created may be designed (e.g., a few kilohertz to a few megahertz).

In the example system of FIG. 6, the raw voltage and current from the photodetector 212 (e.g., a photodiode), along with the pulse streams from the ring oscillator 602, are electrically coupled to a voltage multiplier circuit 604 (hereafter just voltage multiplier 604). The precise nature of the voltage multiplier 604 depends on the voltage levels and power requirements of the overall optoelectronic device 104. In some cases, the voltage multiplier may be a DC-to-DC converter, such as a Dickson Charge Pump; however, any suitable voltage multiplier circuit may be used. The output voltage of the voltage multiplier 604 is designated with the drawing as $V_{UNREG}$, indicating its status as a somewhat unregulated voltage that may change based on several factors, such as power draw by the remaining components and the amount of optical energy extracted by the photodetector 212. The $V_{UNREG}$ voltage is applied to a storage capacitor 606, which stores energy as, needed, and in an example case the voltage multiplier 604 outputs the $V_{UNREG}$ voltage at about 2.0 volts.

Still referring to FIG. 6, the $V_{UNREG}$ voltage in the example system is then applied to a reference voltage generator circuit 608 (hereafter just reference voltage generator 608). As the name implies, the reference voltage generator 608 takes $V_{UNREG}$ voltage and creates therefrom a stable reference voltage (e.g., about 1.2 volts) regardless of the swings of the $V_{UNREG}$ voltage above the reference voltage. The reference voltage created by the reference voltage generator 608, however, is not intended to provide significant power to downstream devices. The output signal of the reference voltage generator 608 in the example system is coupled to a voltage divider circuit 610 (hereafter just voltage divider 610). As the name implies, the voltage divider 610 takes as an input voltage the reference voltage 614 and produces as an output signal a second reference voltage 614 lower than the reference voltage 612. In some cases, the voltage divider 610 is implemented as a transistor-chain voltage divider, but any suitable circuit may be used. In some cases, the reference voltage 612 may be sufficient for downstream devices, and thus the voltage divider 610 may be omitted.

The next component in the example power circuit 214 is the voltage regulator 616. The voltage regulator 616 couples to the reference voltage 614 for use as a reference in the voltage control, and also couples to the $V_{UNREG}$ voltage from the storage capacitor 606 and/or voltage multiplier 604. The voltage regulator 616 provides a regulated power signal VREG to the other devices of the optoelectronic device 104 with a power level on the order of microwatts or less. In example systems, the voltage regulator 616 is implemented as a low-dropout regulator such that the regulation still occurs when the $V_{UNREG}$ voltage is very close to the regulated voltage. In example systems, the VREG voltage is about 1.2 volts.

Still referring to FIG. 6, in the conceptual groupings the power circuit 214 also provides various reference voltages and clock signals to the driver circuit 216 and the sensor circuit 218. To the extent such additional voltage references are needed, the reference voltage generator 608 may be designed and constructed to provide such reference voltages (as illustrated by $V_{REF}$), or additional reference voltage circuits may be designed and implemented. Likewise, to the extent additional clock signals are needed, the example power circuit 214 includes a clock generator 618 circuit designed and constructed to provide the additional clock signals (generally designated 620) at the desired frequencies and duty cycles. In other cases, the ring oscillator 602 may be designed and constructed to provide some or all the additional clock signals, and thus the clock generator 618 may be omitted.

In cases where the power requirements of the optoelectronic device 104 are low (e.g., no or low power sensor circuit), the voltage multiplier 604 may be omitted, and the photodetector 212 implemented as a plurality of photodiodes connected in series to produce the design $V_{UNREG}$ voltage. Before proceeding, it is noted that the optoelectronic device 104 is designated as "passive" in the sense that power to operate the device may be harvested from optical energy incident upon the device. However, in accordance with example embodiments "passive" only refers to source of energy used to operate the device, and shall not speak to any other feature or component of the optoelectronic device.

Figure 7:
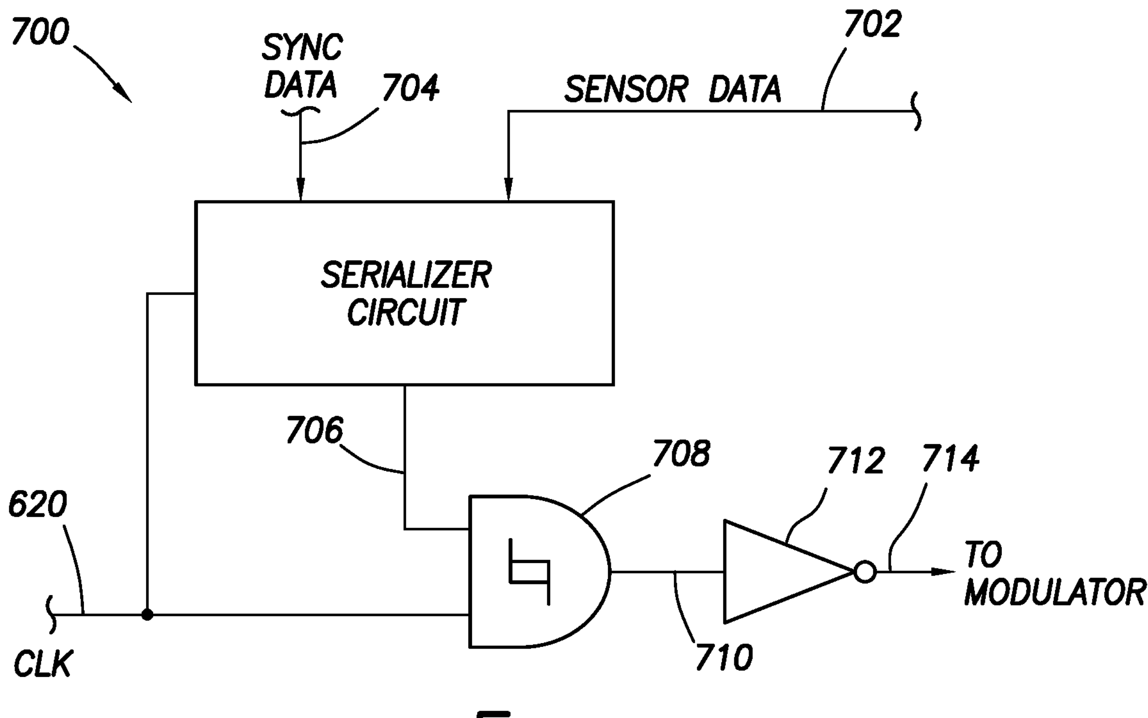
FIG. 7 shows an electrical block diagram of a driver circuit in accordance with example embodiments.

FIG. 7 shows an electrical block diagram of a driver circuit 216 in accordance with example embodiments. In particular, the example driver circuit 216 comprises a parallel-to-serial circuit 700 (hereafter just serializer circuit 700). The data created by the sensor circuit 218 (FIG. 2), the sensor data 702 in the figure, may be coupled to the driver circuit 216 in parallel form. In order to modulate the infrared light propagating within primary waveguide 126 (FIG. 1), the data is converted to a stream of pulses by way of the serializer circuit 700. In order for the optical reader 102 to demodulate the data received, the modulated infrared light may also include a series of synchronization pulses. In the example system, the synchronization data 704 is fed in parallel to the serializer circuit 700, and thus the synchronization pulses may be included as a prefix or a suffix to the sensor data 702 in the serialized version. In the example system the serialized output signal 706 and one of the clock signals 620 are coupled to the input ports of a logic AND gate 708. The output port 710 of the AND gate 708 comprises (over time) the serialized data. The output port 710 is coupled to the driver circuit, shown in FIG. 7 as a NOT gate, but any suitable inverting amplifier may be used. In example systems, there may be additional circuits between the logic AND gate 708 and the driver 712 to pulse shaping/sharpening, but such additional circuits are omitted so as not to unduly complicate the figure. The output signal 714 is electrically coupled to the modulator 208 (FIG. 2) to control the state of the modulator.

Figure 8:
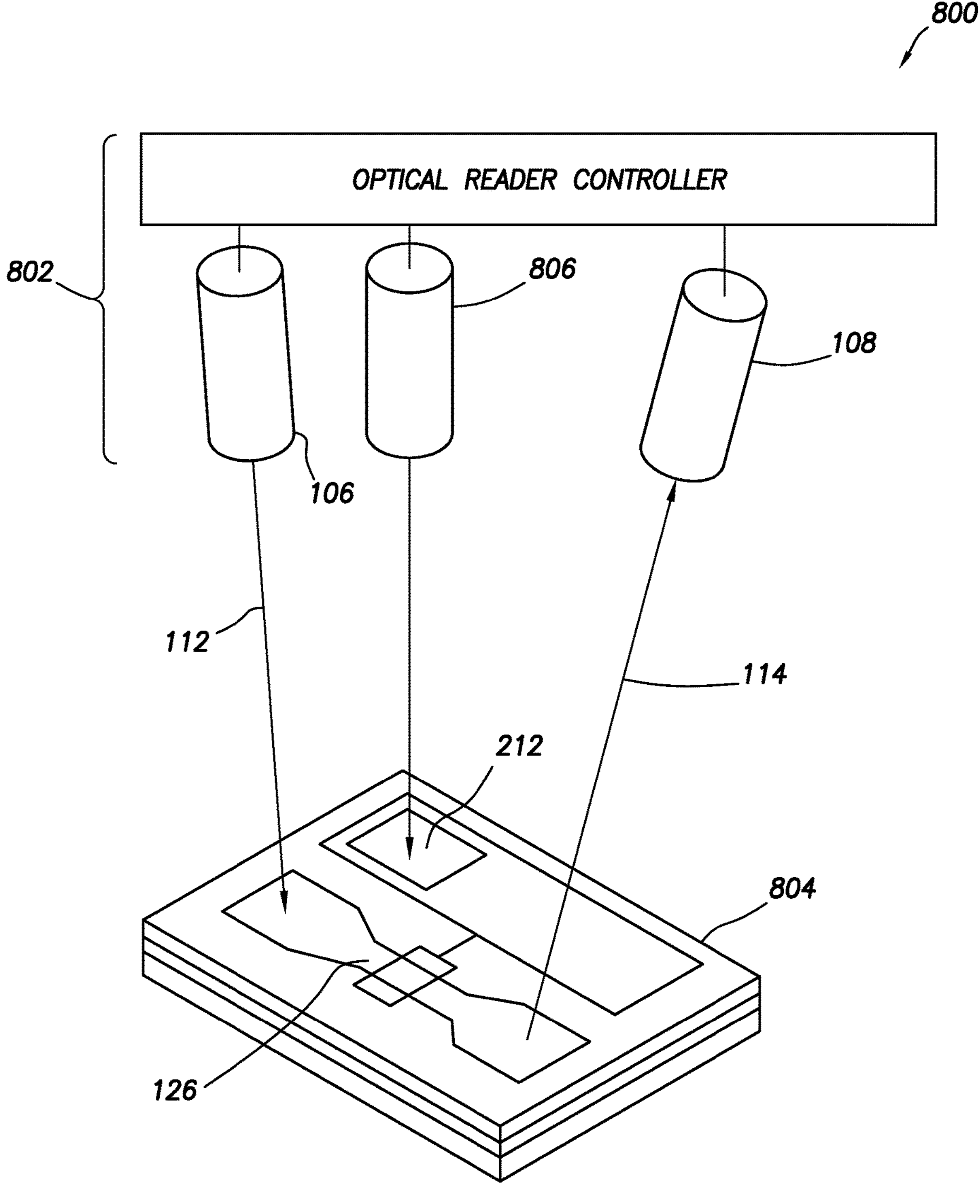
FIG. 8 shows a system in accordance with at least some embodiments.

The various embodiments discussed to this point have assumed the single optical source 106 (FIG. 1) providing the infrared light that is modulated and returned to the optical reader 102, with the optoelectronic device powered by ambient light. In other cases, however, it may be beneficial to use two optical sources to illuminate the optoelectronic device. FIG. 8 shows a system 800 in accordance with at least some embodiments. In particular, the system 800 comprises an optical reader 802 optically coupled to an optoelectronic device 804. As shown, the optical reader 802 may be remote from the optoelectronic device 804 (e.g., on the order of a few meters to a kilometer or more). The sizes of the optical reader 802 and the optoelectronic device 804 of FIG. 8 are not to scale.

The optical reader 802 comprises optical source 106, optical receiver 108, and optical reader controller 110, similar to the optical reader 102 (FIG. 1). Optical reader 802 additionally comprises a second optical source 806. In example systems, the optical source 106 produces light 112 at a first wavelength, and optical source 806 produces light at a second wavelength different than the first wavelength. In example systems, the infrared light 112 produced by optical source 106 is the infrared light that is optically coupled into the optoelectronic device 804, is modulated by the optoelectronic device 804, and is returned as modulated infrared light 114. In order to provide good optical coupling into the primary waveguide 126, the wavelength of infrared light produced by the optical source 106 is about 1.2 microns or greater. However, considering the photodetector 212, silicon absorbs infrared energy more efficiently at wavelengths of less than about 1 micron. Thus, in some situations it may be beneficial to illuminate the optoelectronic device 804 with two different wavelengths—the first wavelength to increase the coupling efficiency into the primary waveguide, and the second wavelength to increase the absorption by the photodetector 212 for purposes of energy harvesting. The second wavelength may be less than 1.3 microns, in some cases less than 1.2 microns, in other cases less than 1.0 microns, and in a particular case may be about 850 nanometers. In all other aspects, the example optoelectronic device 804 is the same as the optoelectronic device 104. In the example optoelectronic device 804, the photodetector 212 is exposed on the outer surface of the device, and may include a single photodiode, or multiple photodiodes connected in series and/or in parallel. The photodetector 212 may also be "behind" the optical coupler as discussed with respect to the optoelectronic device 104.

As for the reason for having dual illumination, for optoelectronic devices 104/804 with sensor circuits that utilize higher relative power (e.g., seismic measurements that require the sensor to be powered for a finite amount of time rather than an instantaneous measurement), the amount of optical energy that can be harvested from infrared light having wavelengths of 1.2 microns and above may be insufficient. Having the second illumination source with wavelengths below 1.0 microns increases the amount of optical energy that can be harvested, yet still utilizing an interrogation infrared light that efficiently couples into the optical components of the optoelectronic device.

Figure 9:
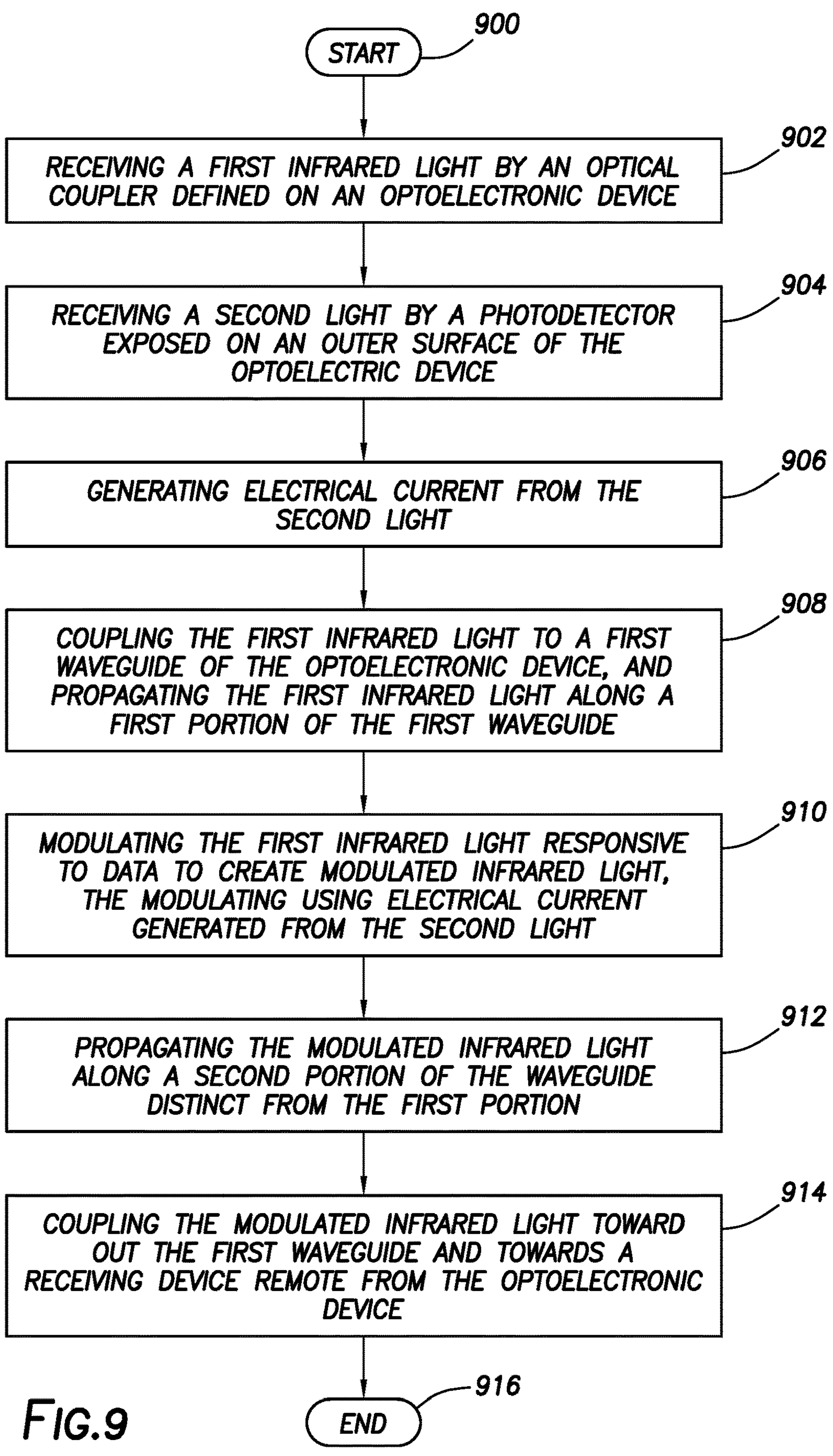
FIG. 9 shows a method in accordance with at least some embodiments.

FIG. 9 shows a method in accordance with at least some embodiments. In particular, the method starts (block 900) and includes: receiving a first infrared light by an optical coupler defined on an optoelectronic device (block 902); receiving a second light by a photodetector expose don an outer surface of the optoelectronic device (block 904); generating electrical current from second light (block 906); coupling the first infrared light to a first waveguide of the optoelectronic device, and propagating the first infrared light along a first portion of the first waveguide (block 908); modulating the first infrared light responsive to data to create modulated infrared light (block 910); propagating the modulated infrared light along a second portion of the waveguide distinct from the first portion (block 912); and coupling the modulated infrared light toward out of the first waveguide and towards a receiving device remote from the optoelectronic device (block 914). Thereafter, the method ends (block 916).

The above discussion regarding the optoelectronic devices is meant to be illustrative of the principles and various embodiments of the present invention. Numerous variations and modifications will become apparent to those skilled in the art once the above disclosure is fully appreciated. For example, while the various embodiments were described as passive devices that harvest optical energy, the devices could be combined with externally affixed batteries to make active devices that can still be read from distances of a kilometer or more. It is intended that the following claims be interpreted to embrace all such variations and modifications.

RFID Device Localization

Related art radio frequency identification (RFID) tag networks for localization, such as reservoir mapping, operate based on the concept that RFID tags communicate with each other through wireless links and calculate respective location through propagation time-delay calculations. However, time-delay based location determination is not practical for several reasons, such as: the RFID tags need to use a high-power transmitter to send signals in a lossy medium; and the time delay of electromagnetic signal transmission from one RFID tag to another depends on the permittivity of the reservoir. As the permittivity can affect the propagation speed of the electromagnetic waves in the reservoir and the reservoir is not a homogenous medium (e.g. water has a much higher electrical permittivity than oil and rock), the accuracy of the localization measurement is significantly reduced. In these methods, RFID tags also need to identify the orientation of each other, which adds further complexity. In other related-art RFID tag networks for localization, operation is based on the theory that sensors can communicate with each other through sound waves (e.g., seismic, microseismic, p-waves, and s-waves) and calculate respective locations through time-delay calculation. However, the sound-wave based method has a similar problem as above since a reservoir is not a homogenous medium for sound waves.

Various embodiments described herein are directed to methods and related systems of mapping target volumes (e.g., the extent of hydraulic fracture of a hydrocarbon-bearing formation) by having each radio frequency identification (RFID) device read and store information from which the location of the RFID device can be directly determined, and without the need for the RFID device to communicate with other RFID devices disposed within the target volume. More specifically, example embodiments broadcast into the target volume source signals originating from known locations (e.g., known locations on the surface of the Earth, or known locations in a borehole disposed in or near the target volume). The inventors have found that under certain conditions the dependence of signal strength of magnetic signals as a function of distance from the source (for constant source strength) is largely independent of the environment through which electromagnetic signals propagate, such that amplitude of the detected magnetic signals is dictated predominantly by distance from the source. The specification first turns to an example environment to orient the reader.

Figure 10:
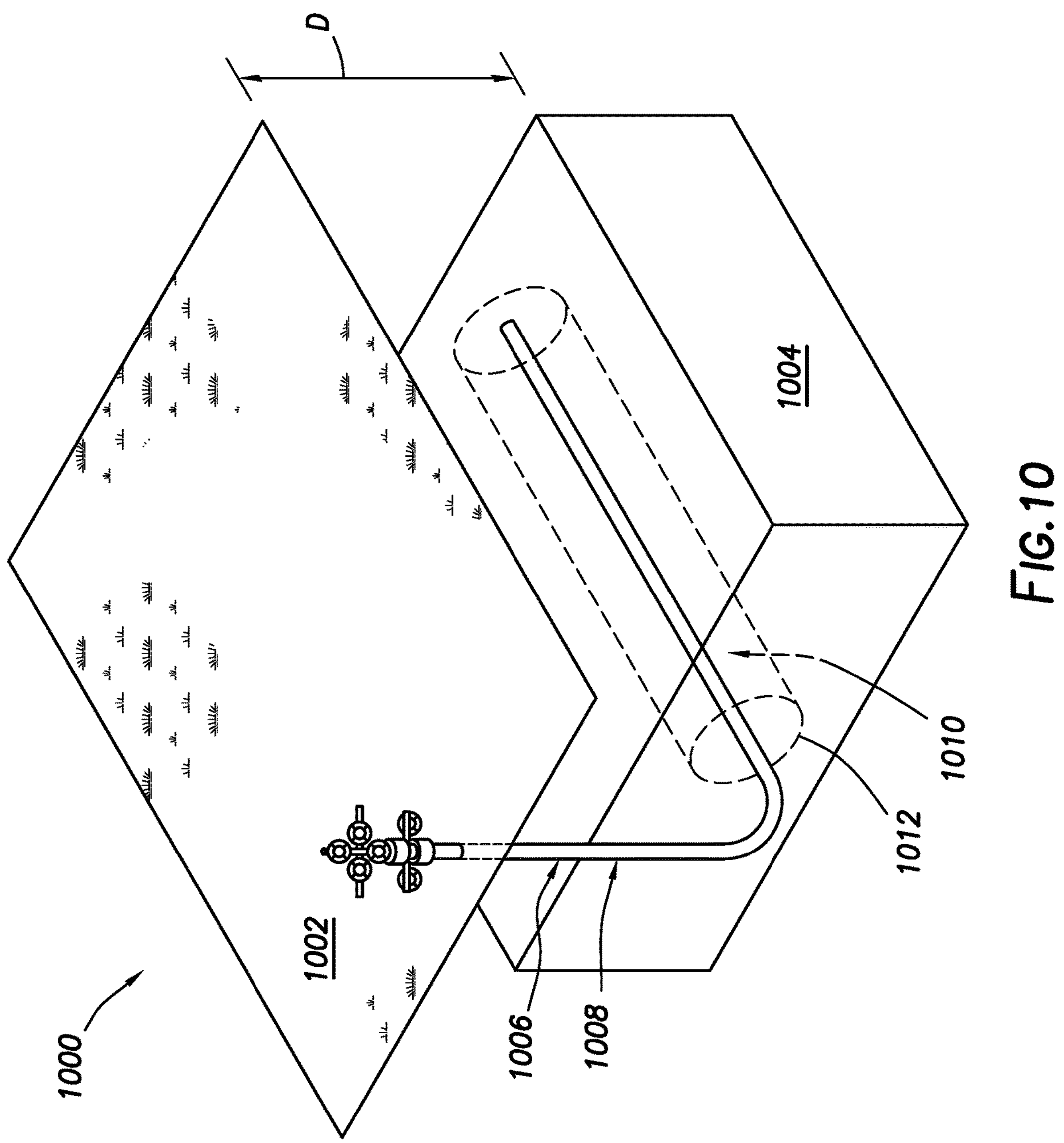
FIG. 10 is a perspective, partial cut-away view, of a hydrocarbon well in accordance with at least some embodiments.

FIG. 10 is a perspective, partial cut-away view, of a hydrocarbon well in accordance with example embodiments. In particular, visible in the example system 1000 of FIG. 10 is the surface 1002 of the Earth. Below the surface 1002 is a hydrocarbon-bearing formation 1004 (hereafter just underground formation or formation 1004). The depth D between the surface 1002 and the formation 1004 varies from location-to-location, but in many cases will be between 2000 and 20000 feet. Between the surface 1002 and the hydrocarbon-bearing formation 1004 resides several thousand feet of overburden (the overburden not specially shown so as not to unduly complicate the figure), with the overburden likely including a range of rock types and saturation materials (e.g., fresh water, brackish water, salt water, other oil and gas formations). It follows that between the surface 1002 and the formation 1004, and within the formation 1004, there is a range of materials with varying dielectric constant. For example, water may have dielectric constant of between 40 and 88 depending on temperature, and oil may have a dielectric constant of 2.1.

The example system further comprises a wellbore or borehole 1006 that extends from the surface 1002 into the formation 1004. The example borehole 1006 has a vertical portion 1008 that curves into a horizontal portion 1010. The horizontal portion 1010 is in many cases directionally drilled so as to follow the contours of the formation 1004 (e.g., the contours of a shale formation, though no contours are specifically shown). In situations where the formation 1004 is a shale formation, in order to economically extract hydrocarbons the formation 1004 may be hydraulically fractured using specially designed fluids with proppant material entrained therein. Fracturing creates a fracture zone 1012 around the borehole 1006 in the formation 1004, with the outer boundaries of the fracture zone 1012 defined at the farthest radial extent of the fractures from the borehole 1006. Many times in shale formations boreholes are created side-by-side within the formation. In such situations it may be beneficial to know with better certainty the extent of the fracture zone 1012. Knowing the extent of the fracture zone 1012 may be beneficial: for gauging hydraulic fracture actual performance; for placement of subsequent boreholes to improve hydrocarbon extraction efficiency; and to ensure that the hydraulic fracture from within one borehole does not break over to the fracture zone of a second borehole.

Figure 11:
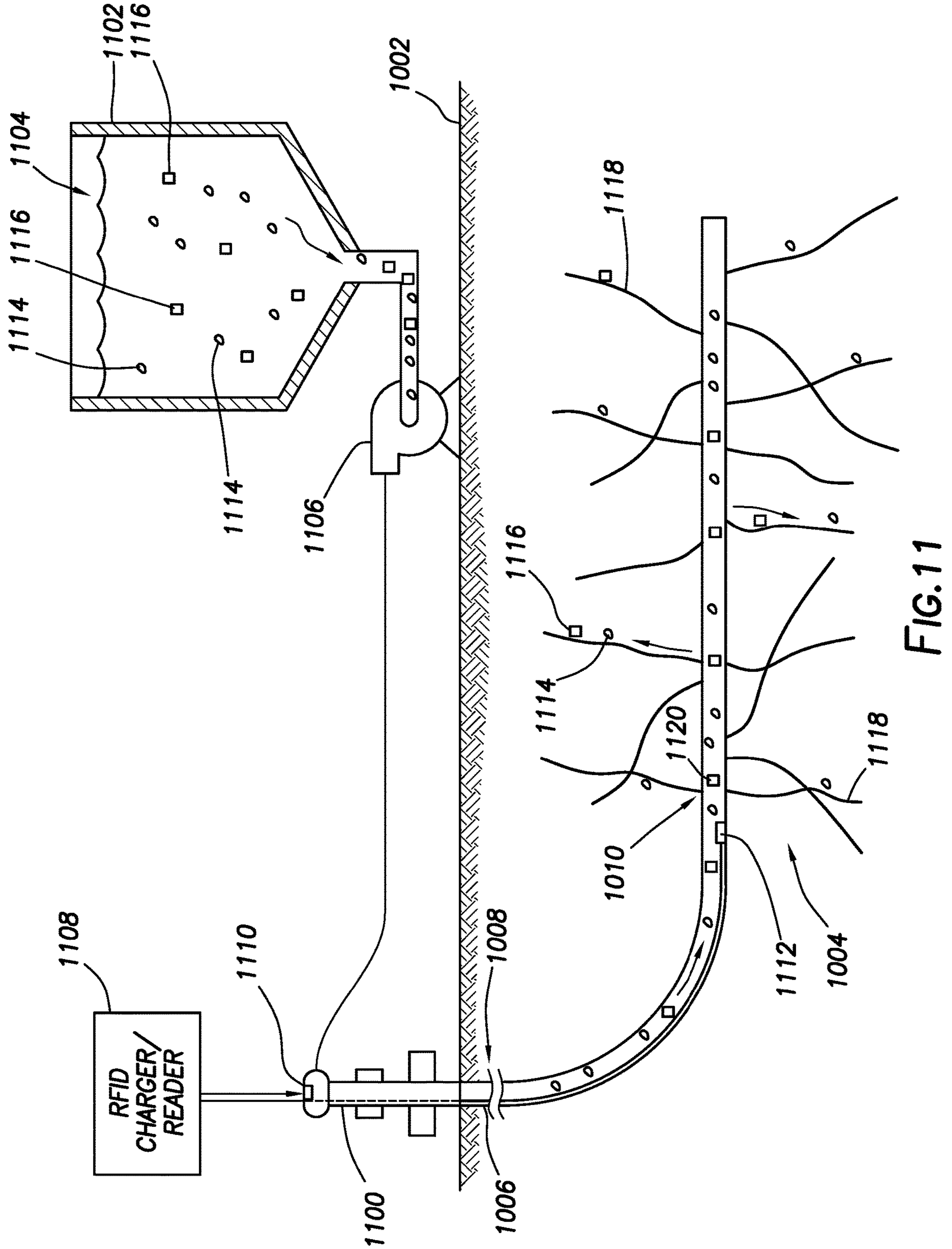
FIG. 11 shows a simplified, partial cross-sectional, view of a hydraulic fracturing operation in accordance at least some embodiments.

FIG. 11 shows a simplified, partial cross-sectional, view of a hydraulic fracturing operation in accordance with example embodiments. In particular, visible in FIG. 11 is the surface 1002 of Earth at which a wellhead 1100 is located. The wellhead 1100 is fluidly coupled to the borehole 1006, including the vertical portion 1008 and the horizontal portion 1010 that extends into the formation 1004 of interest. At the surface 1002 resides a holding tank 1102 (shown in cross section) with hydraulic fracturing fluid 1104 contained therein. The holding tank 1102 is fluidly coupled to an inlet port of a pump 1106, and the outlet port of the pump 1106 is fluidly coupled to the wellhead 1100. While pump 1106 is shown as a centrifugal pump, in many cases the pump used for hydraulic fracturing is a positive displacement pump to reach outlet pressures used to hydraulically fracture the formation 1004. The example system of FIG. 11 further comprises an RFID charger/reader 1108. The example RFID charger/reader 1108 may have a charging antenna 1110 in operational relationship to the fluid inlet port at the wellhead 1100. In other cases, the RFID charger/reader 1108 may have a charging antenna 1112 disposed within the borehole 1006 proximate the perforations in the casing (the perforations and casing not specifically shown).

The fracturing fluid 1104 in accordance with example embodiments includes not only proppant materials 1114, but also a plurality of RFID devices 1116 entrained within the fluid. The size of the proppant material 1114 and RFID devices 1116 is exaggerated in the figures for purposes of discussion. In many cases, the proppant material 1114 may have a largest dimension ranging from about 1000 microns to a few millimeters. Moreover, the RFID devices 1116 in accordance with example embodiments have a largest dimension of about 400 microns or less. There may be many thousands or hundreds of thousands of RFID devices 1116 entrained in the fracturing fluid 1104. As will be discussed more below, in example cases each RFID device 1116 is an individual device or chip monolithically constructed, and thus the cost of each RFID device 1116 may be on the order of few cents or less when produced bulk.

During a fracturing operation in accordance with example embodiments, the fracturing fluid 1104 along with the entrained proppant material 1114 and RFID devices 1116 are pumped through the wellhead 1100, down through borehole 1006, through perforations in the casing (neither the casing nor the perforations specifically shown), and out into the target volume in the form of formation 1004. The pressure at which the fracturing fluid 1104 is pumped into the formation causes the formation 1004 to fracture, and thus fracturing opens channels 1118 (only a few of the channels specially numbered) within the formation 1004. In general, the channels are large enough to enable the proppant material 1114 and RFID devices 1116 to travel out into the formation 1004.

In accordance with example embodiments, the RFID devices 1116 are used to help determine the extent of the fracture zone 1012 (FIG. 10) in a formation created by hydraulic fracturing, possibly along with determining further physical parameters surrounding the RFID devices 1116. In order to achieve the size of the RFID devices 1116 small enough to travel with the proppant material 1114 through the channels 1118 into the formation 1004, in some cases the RFID devices 1116 do not include separately mounted batteries or capacitors; rather, the RFID devices in the example systems are monolithically constructed with onboard capacitance and other devices (e.g., antennas) that harvest energy electromagnetic signal incident upon the RFID devices 1116. Thus, in accordance with example embodiments the RFID devices 1116 may be initially charged while being pumped into the formation 1004. For example, the RFID charger/reader 1108 may transmit electromagnetic energy to the RFID devices 1116 by way of the charging antenna 1110 associated with the wellhead 1100. As yet another example, the RFID charger/reader 1108 may transmit electromagnetic energy to the RFID devices 1116 by way of the charging antenna 1112 disposed in the borehole near or at the locations where the RFID devices transition out of the casing and into the formation.

Once charged, the RFID devices collect data for as long as the stored energy allows. The data collected includes receiving and recording location signals (discussed in greater detail below), timing signals, and in some cases measuring properties of the fracturing fluid and/or formation contemporaneously with the receiving and recording the location signals. Consider, as representative of all the RFID devices 1116, RFID device 1120 in the borehole 1006 that (in the static state of FIG. 11) has just passed the charging antenna 1112. As the RFID device 1120 continues along with the fracturing fluid, the RFID device 1120 receives and periodically records location signals from which the location of the RFID device 1120 can be determined. Thus, the RFID device 1120 (as with all the RFID devices 1116) records a series of values from which the location of the RFID device 1120 over time may be determined (reading the RFID devices 1116 is discussed more below). In some cases, the RFID device 1120 may also record values indicative of time, so that the location information can be correlated to time. The information in the form of the locations of the RFID device 1120 alone is valuable, not only in plotting the course or track of each specific RFID device 1120, but also in determining how far from the borehole 1006 each RFID device travels (i.e., the extent of the fracture zone 1012 (FIG. 10)).

Moreover, in some example systems the RFID devices 1116 also include one or more sensors configured to read a physical parameter proximate to the RFID device contemporaneously with recording the location signals. For example, the RFID devices may have sensors that can sense: temperature (e.g., temperature of the fracturing fluid in which the RFID device is entrained, and/or the temperature of the formation); pressure; pH; electrical conductivity; DC or AC magnetic field; DC or AC electric field; electrical permittivity; magnetic permeability; nuclear magnetic resonance (NMR) spectrum; electron spin resonance (ESR) spectrum; florescence response; porosity; and/or permeability. The physical parameter in combination with the location information may provide value information regarding the formation. For example, the pressure information in combination with the location information may provide insight into the flowability of the formation along the channel within which the RFID device resides. Once pumping of the fracturing fluid into the formation 1004 has completed, either immediately thereafter, or at some later time, the fracturing fluids are allowed to flow back to the surface (along with the initial production of oil and/gas). In accordance with example embodiment, the RFID devices 1116 are read either during the return trip to the surface or after the returning to the surface.

Figure 12:
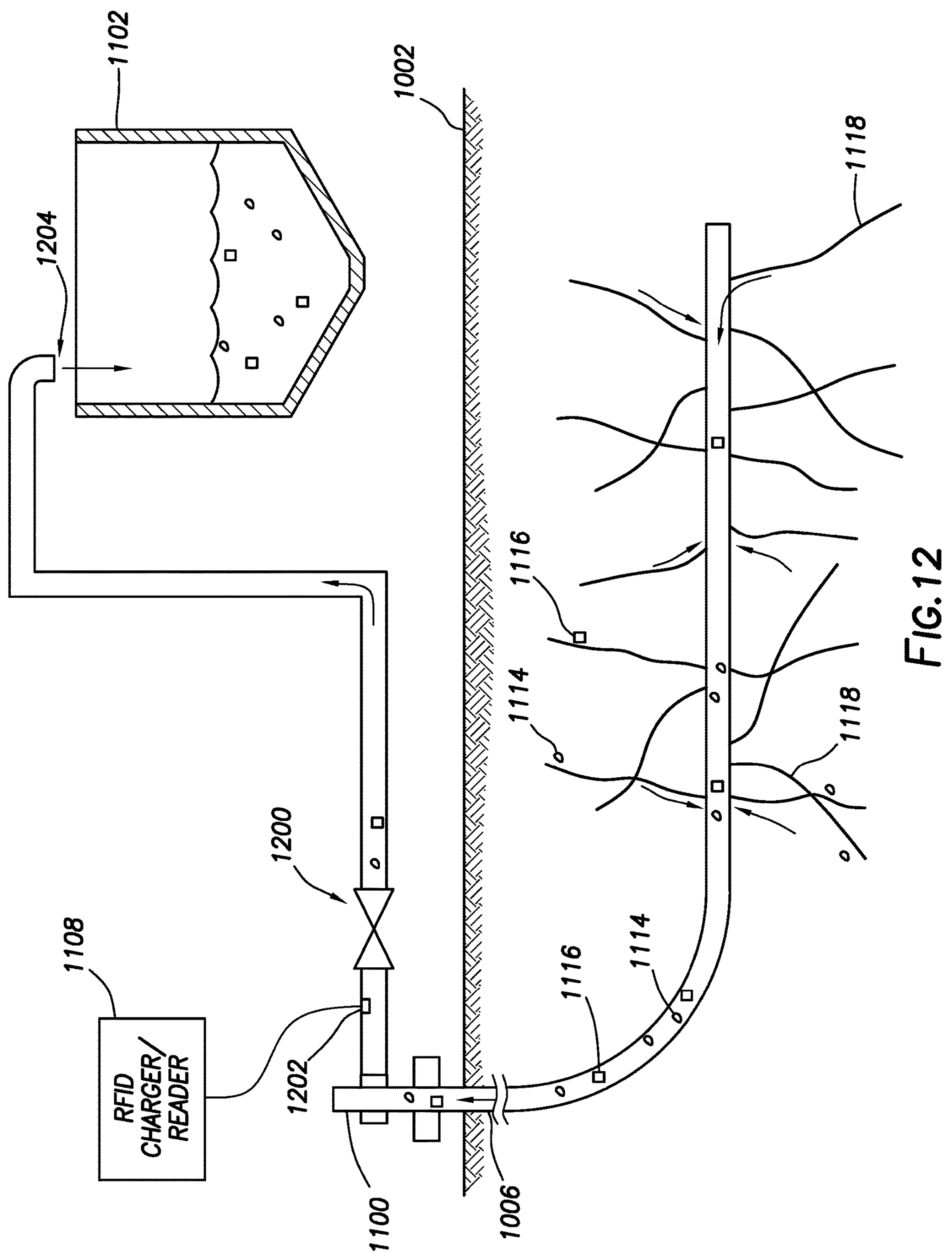
FIG. 12 shows a simplified, partial cross-sectional view of a flow back operation after a hydraulic fracturing in accordance with at least some embodiments.

FIG. 12 shows a simplified, partial cross-sectional view of a flow back operation after a hydraulic fracturing, and in accordance with example embodiments. In particular, the borehole 1006 may be coupled to holding tank 1102 by various piping coupled to the wellhead 1100. A valve 1200 (and various other pieces of equipment not specifically shown) is coupled between the wellhead 1100 and the holding tank 1102, the valve 1200 to help control the flow back of fluids. In example systems, the RFID charger/reader 1108 is electrically coupled to a reading antenna 1202 (which may be the same as the charging antenna 1110 (FIG. 11)). The example reading antenna 1202 is shown to reside at the surface 1002 in the piping between the wellhead 1100 and the valve 1200; however, the reading antenna 1202 may be placed at any suitable location, such as downstream of the valve 1200, or in relation to the discharge 1204 of the piping into the holding tank 1102. Once valve 1200 is opened, the fracturing fluid within the formation flows back toward the surface 1002 as shown by various arrows embedded within the drawing. Some of the proppant material 1114 and RFID devices 1116 may become forever lodged in the formation 1004, and in fact it is expected that the proppant material 1114 will become lodged because of its size, which helps hold the channels 1118 open. However, many of the RFID devices 1116 will be carried back to the surface with the returning fracturing fluid. As the RFID devices 1116 pass the reading antenna 1202, the RFID charger/reader 1108 again powers the devices, and the RFID devices 1116 transmit their stored data to the RFID charger/reader 1108. It is from the data provided by the RFID devices 1116 that the various parameters of interest regarding the formation may be directly or indirectly determined. The specification now turns to a more detailed description of the location signals received and stored by the RFID devices. The measured parameters by the RFID devices may be stored in an integrated non-volatile memory. This ensures that if the RFID devices run out of power, the measured parameters will not be affected, as they are stored in a non-volatile memory. A non-volatile memory is a memory that keeps information even if the power is lost. This information can be retrieved in the surface. Non-limiting examples of non-volatile memory include flash, spin devices, ferromagnetic gates, magnetic memory, high-k dielectric materials, and the like.

Figure 13:
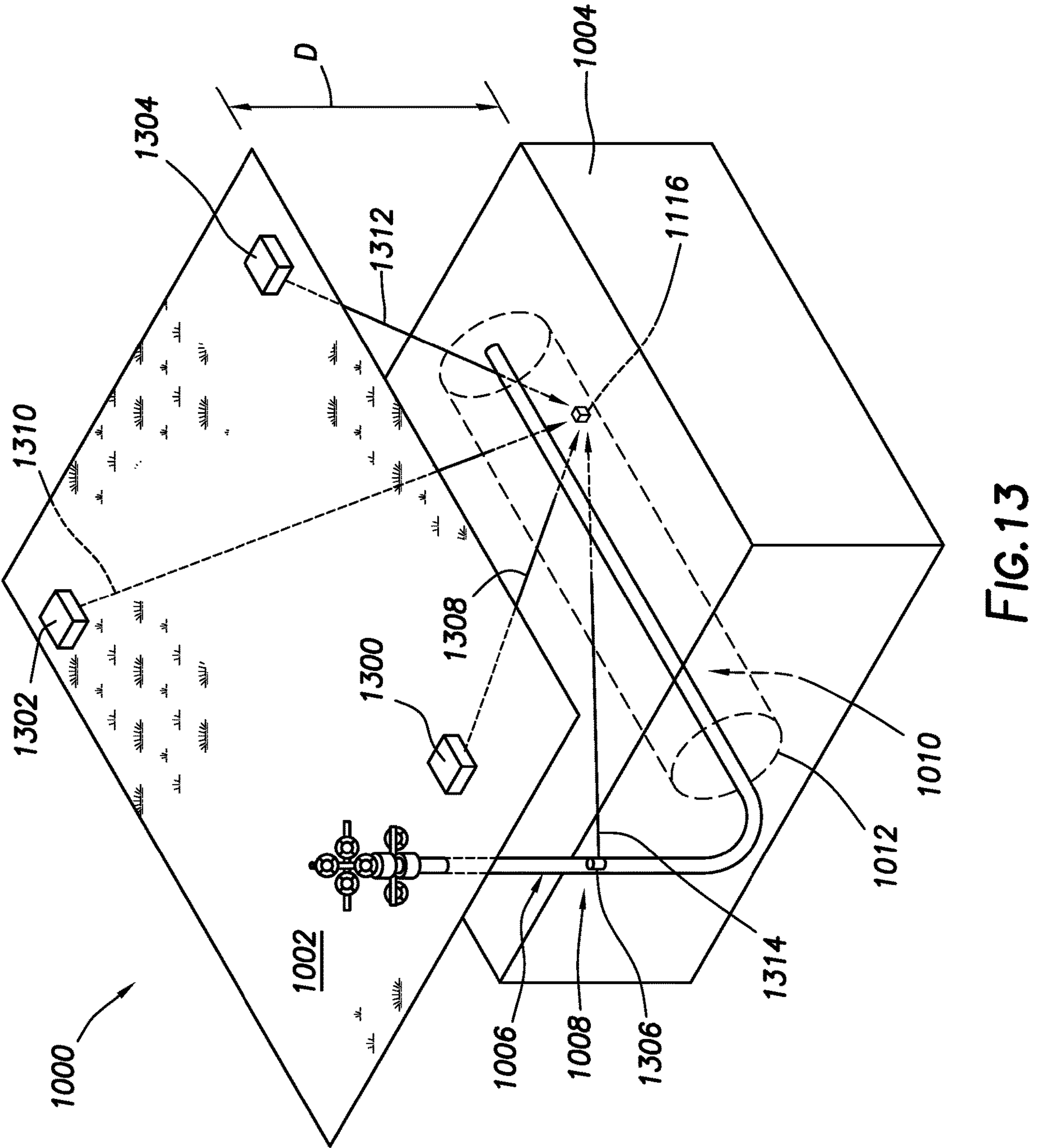
FIG. 13 is a perspective, partial cut-away view of the hydrocarbon well similar to FIG. 10, and in accordance with at least some embodiments.

FIG. 13 is a perspective, partial cut-away view of the hydrocarbon well similar to FIG. 10. In particular, FIG. 13 shows a situation where an RFID device 1116 is within the formation 1004 during the hydraulic fracturing process; however, the surface equipment associated with the fracturing operation is not shown so as not to unduly complicate the figure. Moreover, only a single RFID device 1116 is shown in FIG. 13, again so as not to unduly complicate the figure. In accordance with example embodiments, as the RFID device 1116 (along with many others not shown) is being pumped into the formation, locations signals are propagated into the formation from a plurality of known locations. The example system shows four electromagnetic (EM) sources 1300, 1302, 1304, and 1306. Each EM source is placed at a spaced-apart and known location. Example EM sources 1300, 1302 and 1304 are placed at known locations on the surface 1002 of the Earth. The locations may be in relation to any suitable reference datum, such as global positioning system (GPS)-based location determinations. The example system further includes an EM source 1306 disposed within the borehole 1006 to exemplify that EM sources may be placed at any known location, not necessarily just surface locations. While FIG. 13 shows four EM sources, three more EM sources may be used to provide suitable location determinations for the RFID devices, with greater location accuracy achieved when greater numbers of EM sources are used.

Referring initially to EM source 1300. EM source 1300 generates an electromagnetic signal or source signal 1308 at a particular frequency. The source signal 1308 thus propagates from outside the formation 1004 (i.e., outside the target volume) to inside the formation 1004 to be incident upon the RFID device 1116. Propagating electromagnetic energy moves in expanding wave fronts, but the source signal 1308 is shown as a line to simplify the drawing; however, it will be understood that source signal 1308 expands out and may be incident upon some or all the RFID devices 1116 within the formation 1004.

EM sources 1302, 1304, and 1306 work similarly to EM source 1300, with the exception that in example embodiments frequencies of the source signals differ from EM source to EM source. Thus, EM source 1302 generates a source signal 1310 which propagates into the formation and is incident upon the RFID device 1116. EM source 1304 generates a source signal 1312 which propagates into the formation and is incident upon the RFID device 1116. EM source 1306 generates a source signal 1314 which propagates into the formation and is incident upon the RFID device 1116.

Figure 14:
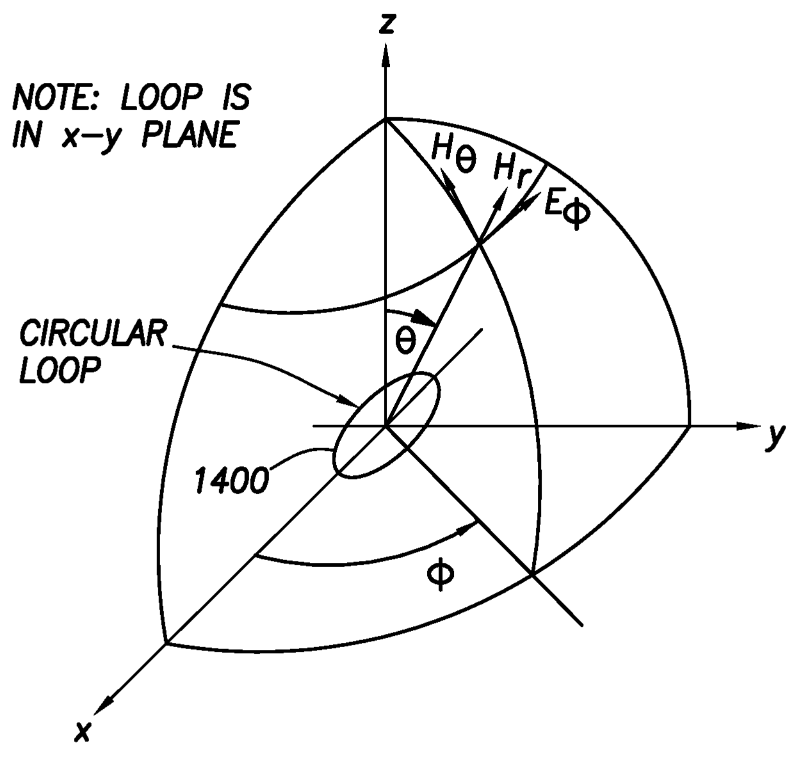
FIG. 14 shows circular loop of wire 1400 within an orthogonal space in accordance with at least some embodiments.

As discussed above, however, the localization of RFID devices implemented in the various embodiments is based on amplitude of the various source signals as recorded by the RFID devices. However, use of amplitude-based localization is non-intuitive. That is, the overburden layers above a hydrocarbon formation and the hydrocarbon formation itself have heterogeneous dielectric constant which implies the amplitude of an electromagnetic signal measured at any particular point away from the source is most heavily dictated by dielectric constant of the overburden and formation. However, the inventors have discovered that in certain conditions the amplitude decay of low-frequency magnetic fields (e.g., one MHz and below), even in volumes of heterogeneous dielectric constant, overwhelmingly depends on the distance and orientation and not the specific makeup of the intervening medium. In order to discuss the conditions, FIG. 14 shows circular loop of wire 1400 within an orthogonal space and with a location within the space designated in spherical coordinates (i.e., points in space designated as radius r, angle $\theta$, and angle $\phi$). In particular, FIG. 14 shows the magnetic field H and electrical field E for an arbitrary location relative to the loop of wire 1400. The electric and magnetic fields at any location in the space as caused by the loop of wire carrying electrical current (i.e., magnetic dipole) can be calculated from the following equations:

$$E_\phi = \frac{\eta}{4\pi}\beta^3\left(\frac{1}{\beta r} - \frac{j}{(\beta r)^2}\right)\sin\theta e^{-j\beta r}M_Z \quad (1)$$

$$H_r = \frac{\beta^3}{2\pi}\left(\frac{j}{(\beta r)^2} + \frac{1}{(\beta r)^3}\right)\cos\theta e^{-j\beta r}M_Z \quad (2)$$

$$H_\theta = -\frac{\beta^3}{4\pi}\left(\frac{1}{\beta r} - \frac{j}{(\beta r)^2} - \frac{1}{(\beta r)^3}\right)\sin\theta e^{-j\beta r}M_Z \quad (3)$$

$$E_r = H_\phi = E_\theta = 0 \quad (4)$$

$$M_z = AI \quad (5)$$

where $E_\phi$ is electric field component in the $\phi$ direction, $\eta$ is the intrinsic wave impedance of the medium (e.g., 377 ohm for air, lower in a hydrocarbon reservoir), $\beta$ is a propagation constant equal to $(2\pi/\lambda)$, $\lambda$ is wavelength, $\beta r$ is the propagation constant multiplied by the spherical radius of the location of interest, $H_r$ is the magnetic field along the radius r, $H_\theta$ is the portion of the magnetic field in the $\theta$ direction, A is the area of the loop of wire, I is the current flowing within the loop of wire, and $M_Z$ is the magnitude of the magnetic dipole created by the loop of wire.

When the frequency is small (i.e., the wavelength is $\lambda$ long), $\beta r$ is much less than one, and thus it is easily shown that:

$$E_\phi \sim 0 \quad (6)$$

$$E_\phi = \frac{-\eta j\beta}{4nr^2}\sin\theta M_Z \sim 0 \quad (7)$$

$$H_r = \frac{1}{2\pi r^3}\cos\theta M_Z \quad (8)$$

$$H_\theta = \frac{1}{4\pi r^3}\sin\theta M_Z \quad (9)$$

where the various parameters are as discussed above.

As shown in Equations (1)-(9), the dependency of the magnetic field to wavelength disappears (i.e., the dependence on $\beta$ and $\beta r$ become negligible) at the frequencies under consideration. In air, for a distance of r=lkm, a frequency of 5 KHz ($\lambda$=60 kilometers) results in:

$$\beta r = 2\pi/60 << 1.0 \quad (10)$$

In a medium with electrical permittivity of 4, a frequency of 2.5 KHz ($\lambda$=60 kilometers) results again in the relationship of Equation 10.

Figure 15:
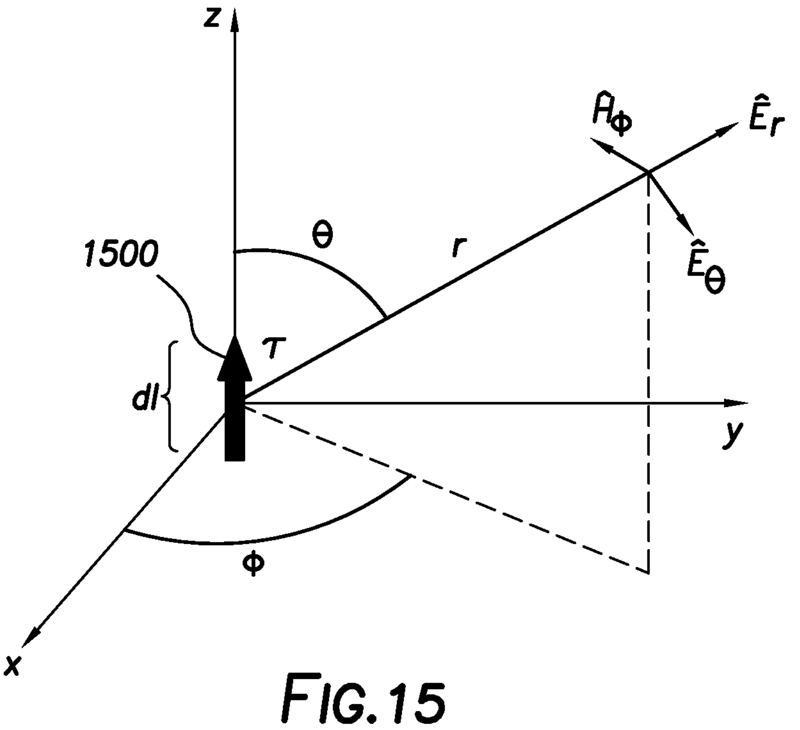
FIG. 15 shows an electric dipole 1500 within an orthogonal space with locations in accordance with at least some embodiments.

FIG. 15 shows an electric dipole 1500 within an orthogonal space with locations again designated in spherical coordinates. In particular, FIG. 15 shows the electric field E and magnetic field H for an arbitrary location relative to the electric dipole 1500 at the origin. The electric and magnetic fields caused by the dipole 1500 can be calculated from the following equations:

$$E_r = \frac{\eta}{2\pi}\beta^2\left(\frac{1}{(\beta r)^2} - \frac{j}{(\beta r)^2}\right)\cos\theta e^{-j\beta r}I_Z L \quad (11)$$

-continued $$H_\phi = \frac{j\beta^2}{4\pi}\left(\frac{1}{\beta r} - \frac{j}{(\beta r)^2}\right)\sin\theta e^{-j\beta r}I_Z L \quad (12)$$

$$E_\theta = \frac{\eta}{4\pi}j\beta^2\left(\frac{1}{\beta r} - \frac{j}{(\beta r)^2} - \frac{1}{(\beta r)^3}\right)\sin\theta e^{-j\beta r}I_Z L \quad (13)$$

$$H_r = E_\phi = H_\theta = 0 \quad (14)$$

where Er is electric field component in the radial direction, Iz is the current in the electric dipole, and L is the length of the dipole, with the remaining parameters as defined above.

When the frequency is small (i.e., the wavelength is $\lambda$ long), $\beta r$ is much less than one, and thus it is easily shown $$E_r \sim \frac{-\eta}{2\pi}\left(\frac{j}{\beta r^3}\right)\cos\theta I_Z L \quad (15)$$

$$H_\phi = \frac{1}{4\pi r^2}\sin\theta I_Z L \quad (16)$$

$$E_\theta = \frac{\eta}{4\pi}j\left(-\frac{1}{\beta r^3}\right)\sin\theta I_Z L \quad (17)$$

$$E_r = E_\phi = E_\theta = 0 \quad (18)$$

Again as shown in Equations (11)-(18), the dependency of the magnetic field to wavelength disappears (i.e., the dependence on $\beta$ and $\beta r$ become negligible) at the frequencies under consideration. Thus, the inventors of the present specification have found that one can determine the location of the RFID devices 1116 by sensing magnetic field created by electromagnetic source signals.

It follows from the discussion above that each EM source 1300-1304 produces a source signal that is electromagnetic and has a relatively low frequency. In some cases, the frequency of each of the source signals is less than 1000 MHz, in some cases less than 1 MHz, in other cases less than 500 kHz, and in yet still other cases 100 kHz or less. The source signals themselves may take any suitable form. For example, each EM source 1300-1306 may implement a magnetic dipole. For example, each EM source may include a loop of wire carrying electrical current. The loop of wire that makes up the EM source may have a radius that ranges from a few centimeters to a few meters, with the loop of wire "located" at the center of the loop. Likewise, the loop of wire that makes up the EM source may carry any of a variety of AC electric currents (at the selected frequency). For example, the loop of wire may carry AC currents having root mean square (RMS) currents between and including 1 amp and 100 amps. The loop of wire may be a single loop, or the loop of wire may comprise several loops (e.g., two loops, 10 loops, 100 loops). The precise design of the EM sources 1300-1304 depends on various parameters, such as the sensitivity to magnetic fields of the RFID devices and the distance between the EM source 1300-1304 locations and the formation within which the RFID devices 1116 are located. It is to be understood that the EM sources 1300-1304 are not limited to just creation of magnetic dipoles, as any electromagnetic signal includes a magnetic component.

EM source 1306 disposed within the borehole may implement a different physical structure because the size of the borehole space constrains EM source 1306. That is, the EM source 1306 may likewise have a loop of wire, but of much smaller diameter. For example, the loop of wire in the EM source 1306 may be several thousand turns of relatively thin wire, possibly wrapped around a core of magnetic material, and carrying a one amp of electric current or less. The specification now turns to the description of an RFID device in accordance with example embodiments.

Figure 16:
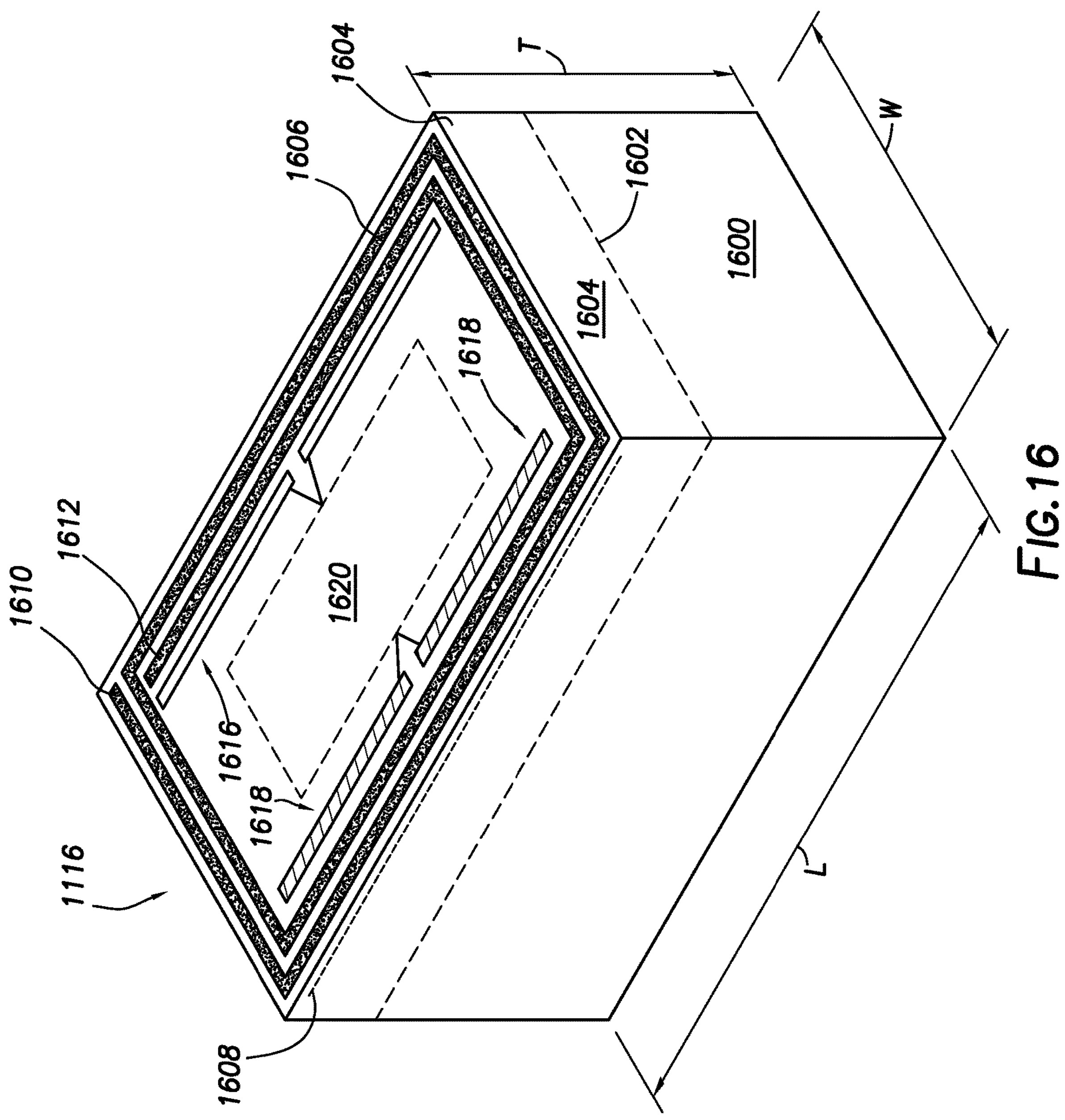
FIG. 16 shows a block diagram of an RFID device in accordance with at least some embodiments.

FIG. 16 shows a perspective view of an RFID device in accordance with at least some embodiments. In particular, the example RFID device 1116 comprises a substrate 1600. In many cases the substrate 1600 is made of silicon, but other substrates are also possible. Constructed upon the substrate 1600 are the various circuits, and antennas, and loops of wire. Dashed line 1602 separates the substrate 1600 from the active area 1604 into which the various components are created; however, in some cases the components of the active area 1604 are built directly on the substrate 1600 and thus no delineation (other than perhaps depth) may be present. In other cases, there may be an insulation layer between the substrate 1600 and the active area 1604 (e.g., a silicon-on-insulator construction). The RFID device has a thickness T, a width W, and length L. The relative thicknesses of the layers are not shown to scale in the figure. Nevertheless, in example systems the substrate 1600 may have a thickness of about 300 microns, and the active area 1604 may have a thickness of about 10 to 100 microns depending on specific design criteria for the device. Thus, the RFID device 1116 may have a thickness T of 400 microns or less (measured perpendicular to the substrate 1600). In some cases, the RFID device 1116 may have a thickness T of about 300 microns or less. Further in example systems, the optoelectronic device may have a length L of 400 microns or less, and a width W of 400 microns or less, as L and W are depicted in FIG. 1 (i.e., measured in a plane parallel to the substrate 1600). In yet still further embodiments, the largest external dimension of the RFID device 1116 (i.e., the longest of any one of T, L, and W in FIG. 16) is 400 microns or less.

Visible on the upper surface of the example RFID device 1116 are several components. In particular, shown on the upper surface is a loop of wire or inductor 1606. The inductor 1606 comprises a first plurality of loops of strips of metallic material. While the portion of the inductor 1606 visible shows two loops, any number of loops of strips of metallic material may be constructed at a uniform depth in the RFID device 1116. In some example devices, at a second depth different than the depth visible on the surface of the RFID device, a second layer or level of loops of strips of metallic material may be present. Such additional layers of loops of strips of metallic material would only be partially visible, even if the various overlying layers were transparent, and thus the additional loops of strips of metallic material are illustrated by dashed line 1608 (positioned to show the additional loops of strips of metallic material may reside directly beneath those visible). The various loops of metallic material are electrically connected through various techniques, resulting in the inductor defining a first lead 1610 and a second lead 1612.

Still referring to FIG. 16, the example RFID device 1116 further comprises a power antenna 1616 on the substrate, the power antenna 1616 in the form of a half-wave dipole antenna. In example systems, the power antenna 1616 has a resonant frequency above 1 MHz, and in some cases the power antenna 1616 has a resonant frequency of 2.45 Gigahertz. As the name implies, the power antenna 1616 is used by the RFID device 1116 to harvest or extract electromagnetic energy to power the RFID device 1116, and in some cases the same electromagnetic signals that power the RFID device can carry coded signals to trigger the RFID device 1116 to transmit encoded data back to the reader. For example, when the RFID device 1116 is being pumped downhole, the RFID charger/reader 1108 (FIG. 11) may broadcast electromagnetic energy having a frequency above 1 MHz but with no encoded data. The RFID device 1116, in turn, receives the electromagnetic energy by way of power antenna 1616 and stores the energy for later use, but does not trigger transmission of the recorded data because the absence of encoded data (or at least not the encoded data that triggers a data transfer). By contrast, as the RFID device 1116 is flowing back to the surface after a hydraulic fracturing operation, the RFID charger/reader 1108 may broadcast electromagnetic energy including encoded data that triggers data transfer.

The example RFID device 1116 further comprises a transmission antenna 1618 on the substrate, the transmission antenna 1618 also in the form of a half-wave dipole antenna. In example systems, the transmission antenna 1616 has a resonant frequency above 1 MHz, and in some cases the power antenna 1616 has a resonant frequency of about 1 Gigahertz. As the name implies, the transmission antenna 1618 is used by the RFID device 1116 to transmit data stored in the RFID device 1116 back to the RFID charger/reader 1108, the data including values indicative of amplitude of magnetic signals received by the inductor 1606. The frequency of transmission by the transmission antenna 1618 is illustrative lower than the frequency at which the RFID device 1116 harvests or extracts energy to make detection by the RFID charger/reader 1108 easier. In further example systems, the frequency at which the transmission antenna 1618 operates may be the same as or higher than the frequency at which the power antenna 1616 extracts energy.

Finally, FIG. 16 shows, by components 1620, generically that the RFID device 1116 contains various other electrical components (discussed in greater detail below). Again it is noted that the drawing of FIG. 16 is not to scale. Moreover, the relative placement of the portion of the inductor 1606 visible in the figure, along the antennas 1616 and 1618, and other components 1620 are merely an example, and should be read to limit the physical layout to what is shown.

Figure 17:
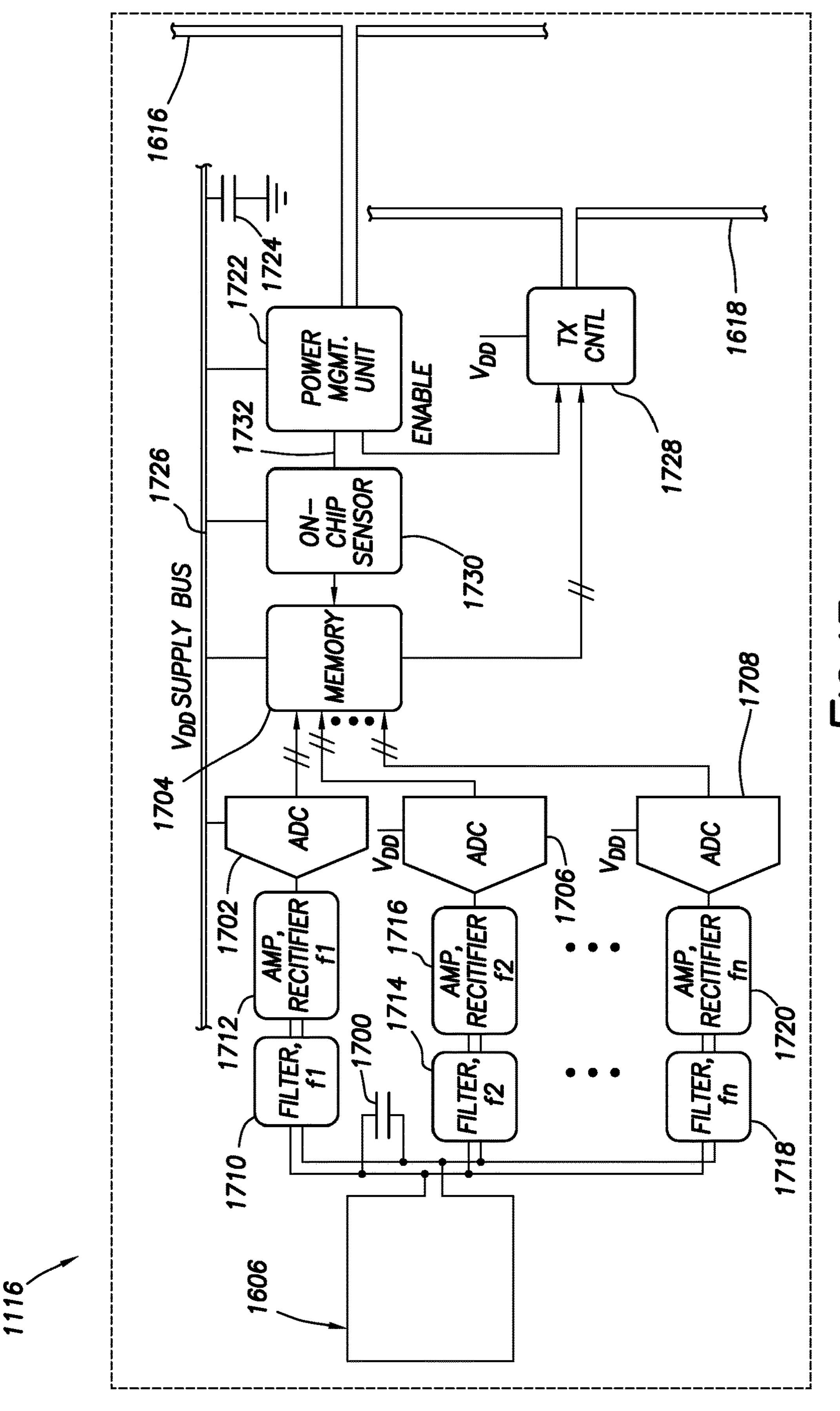
FIG. 17 shows, in block diagram form, various electrical components of an RFID device in accordance with at least some embodiments.

FIG. 17 shows, in block diagram form, various electrical components of an RFID device 1116 in accordance with at least some embodiments. In particular, all the components that are discussed with respect to FIG. 17 are created on and thus defined on the substrate 1600 (FIG. 16). The RFID device 1116 comprises the inductor 1606 as discussed above. A capacitor 1700 is electrically coupled to the inductor 1606, and the capacitance of the capacitor 1700 considered with the inductance of the inductor 1606 have a resonant frequency below 1 MHz, and in some cases below 500 kHz. The inductor 1606 and capacitor 1700 are electrically coupled to an analog-to-digital (AD) converter 1702 (labeled ADC 1702 in the figure). As the name implies, the AD converter 1702 reads analog signals, and creates therefrom a series of digital values (e.g., digital values with six bit resolution). The AD converter 1702 is electrically coupled to memory 1704. The memory 1704 is configured to store digital data, and the memory is nonvolatile in the sense that data values written therein remain even after all the stored energy of the RFID device 1116 (the stored energy portions discussed more below) has been depleted. In accordance with example embodiments, the AD converter 1702 is configured to read values indicative of amplitude of electromagnetic signal read by the inductor 1606, and the RFID device 1116 is configured to store the values in the memory 1704 for later reading.

The example RFID device 1116 further comprises additional AD converters 1706 and 1708. Each AD converter

1706 and 1708 is coupled on its analog side to the inductor 1606, and each AD converter 1706 and 1708 is coupled on its digital side to the memory 1704. Much like AD converter 1702, the AD converters 1706 and 1708 are configured to read values indicative of amplitude of an electromagnetic signal detected by the inductor 1606, and configured to store the values in the memory 1704 for later reading. While FIG. 17 shows three AD converters 1702, 1706, and 1708, three or more AD converters may be used (e.g., corresponding to the number of EM sources utilized).

As discussed above, example systems including a plurality of EM sources 1300-1306 producing a plurality of source signals, each source signal having a different frequency. The inductor 1606 thus receives a combined signal being the superposition of all the source signals. In order to differentiate the various source signals, in some embodiments the source signals received by the inductor 1606 are filtered in the time domain. Thus, in accordance with example embodiments, the RFID device 1116 further comprises an analog filter 1710 coupled between the inductor 1606 and the AD converter 1702. The analog filter 1710 is a bandpass filter having a center frequency "f1" designed to match the frequency of one of the example EM sources 1300-1306. In some cases, the RFID device 1116 further comprises an amplifier 1712 electrically coupled between the analog filter 1710 and the AD converter 1702. As the name implies, the amplifier 1712 may amplify the signals received by the inductor 1606 (and filtered by the analog filter 1710). Moreover, in cases such as shown in FIG. 17 where the filtering is performed in the analog domain, the amplifier 1712 may also half- or full-wave rectify the received signal such that the AD converter 1702 converts peak values to digital form for storage in the memory 1704. Similarly for AD converter 1706, the example system implements an analog filter 1714 coupled between the inductor 1606 and the AD converter 1706. The analog filter 1714 is a bandpass filter having a center frequency "f2" designed to match the frequency of one of the example EM sources 1300-1306. Moreover, the example RFID device 1116 further comprises an amplifier 1716 electrically coupled between the analog filter 1714 and the AD converter 1706 for amplifying and possibly rectifying the received signals. And similarly for AD converter 1708, the example system implements an analog filter 1718 coupled between the inductor 1606 and the AD converter 1708. The analog filter 1718 is a bandpass filter having a center frequency "fn" designed to match the frequency of one of the example EM sources 1300-1306. Moreover, the example RFID device 1116 further comprises an amplifier 1720 electrically coupled between the filter 1718 and the AD converter 1706 for amplifying and possibly rectifying the received signals. The amplifiers 1712, 1716, and 1720 may be omitted depending on the signal strength of the received signals. Moreover, AD converters 1702, 1706, and 1708 may convert the full-wave source signals received, and thus the rectifier functionality may likewise be omitted in some cases.

Still referring to FIG. 17, the example RFID device 1116 further comprises the power antenna 1616. The power antenna 1616 is electrically coupled to a power management unit 1722. The power management unit 1722 receives the electromagnetic energy received by the power antenna 1616, harvests the energy, and stores the energy to storage capacitor 1724 coupled to the power management unit 1722 by way of the $V_{DD}$ supply bus 1726. The power management unit 1722 also decodes any encoded data "riding" the electromagnetic data, and in the presence of the predetermined encoded data (i.e., an interrogating signal) the power management unit 1722 also triggers various other components to broadcast data.

The example RFID device 1116 further comprises the transmission antenna 1618. The transmission antenna 1618 is electrically coupled to a transmission controller 1728 (labeled "TX CNT'L" in the figure). The transmission controller 1728, in turn is electrically coupled to the $V_{DD}$ supply bus 1726, the memory 1704, and the enable signal of the power management unit 1722. The transmission controller 1728, when enabled by the power management unit 1722, reads the data from the memory 1704, and broadcasts the data to the RFID charger/reader 1108 (FIG. 11) by way of the transmission antenna 1618. As discussed above, the transmission controller 1728 and transmission antenna 1618 in example systems, are designed and constructed to transmit at frequency different than the frequency at which the power antenna 1616 harvests energy. For example, in some cases the power antenna 1616 harvests energy at about 2.45 GHz, while the transmission antenna 1618 (as driven by the transmission controller 1728) broadcasts about 1.2 GHz. Other charging frequencies and broadcast frequencies may be used, but in most cases the charging and broadcast frequencies are 1 MHz and above.

Finally with respect to FIG. 17, the example RFID device 1116 also comprises an optional on-chip sensor 1730. The on-chip sensor 1730 electrically couples to the $V_{DD}$ supply bus 1726 and draws power therefrom. Depending on the nature of the on-chip sensor 1730, additional supply and/or reference voltages may be needed, and in such cases the power management unit 1722 may supply those voltages as shown by connection 1732. The on-chip sensor 1730 also electrically couples to the memory 1704. Thus, when present and when powered, the on-chip sensor reads a physical parameter proximate to the RFID device 1116, and provides the data to the memory 1704 for storage and later broadcast by the transmission controller 1728 and transmission antenna 1618. The various physical parameters that the on-chip sensor 1730 may be constructed to read are discussed above.

Figure 18:
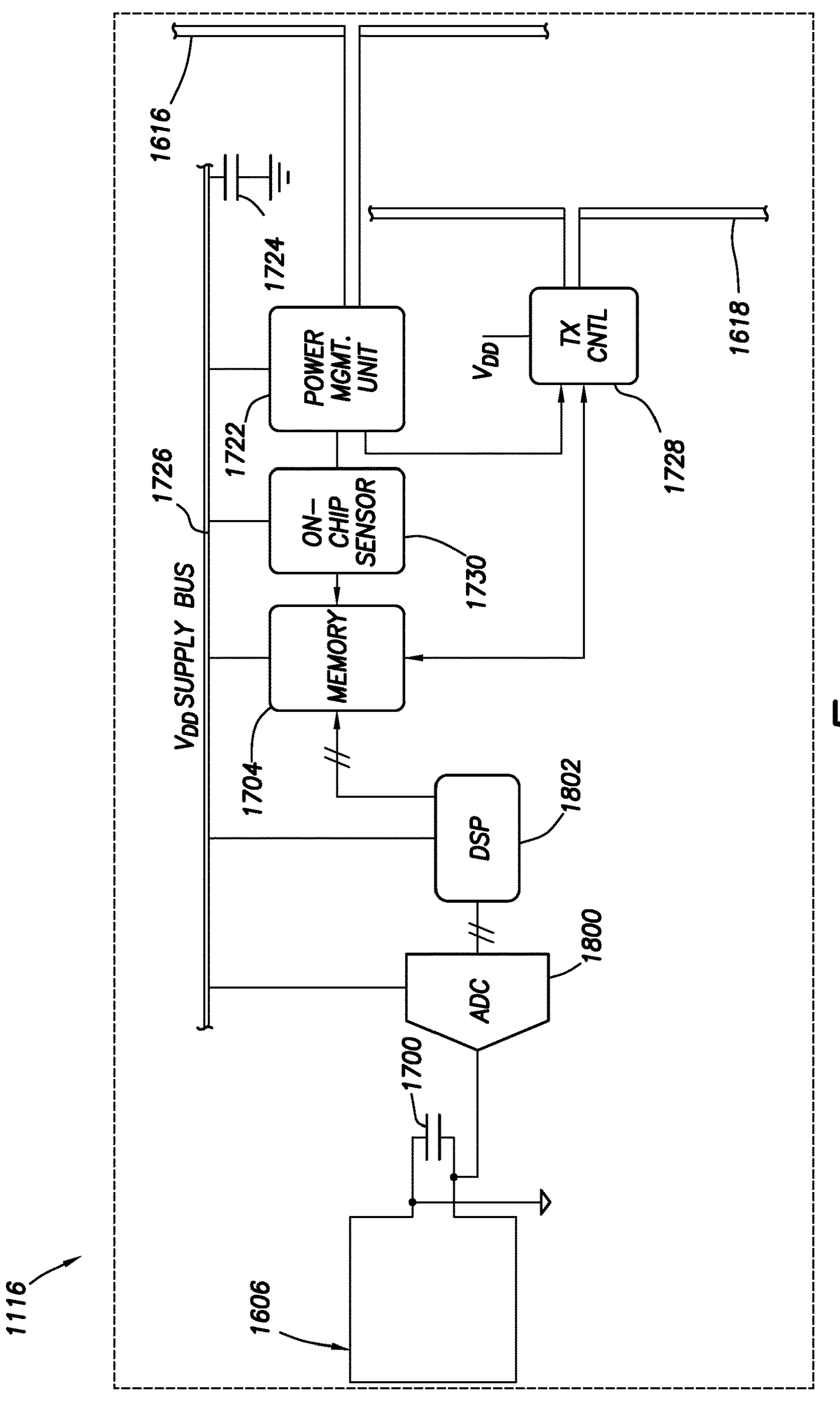
FIG. 18 shows, in block diagram form, various electrical components of an RFID device in accordance with at least some embodiments.

FIG. 18 shows, in block diagram form, various electrical components of an RFID device 1116 in accordance with further example embodiments. In particular, the example RFID device 1116 of FIG. 18 has many similar components to the device of FIG. 17, and the shared components will not be described again in detail. Unlike FIG. 17, the example RFID device 1116 of FIG. 18 has a single AD converter 1800. The AD converter 1800 is coupled on its analog side to the inductor 1606, and the AD converter 1800 is coupled to the memory 1704 by way of a digital signal processor 1802 (labeled DSP in the figure). The AD converter 1800 may be of similar construction and operation as any of the previously discussed AD converters. In the example system of FIG. 18, rather than performing the filtering of the source signals with respect to frequency in the analog domain, the filtering is performed in the digital domain. That is, the AD converter 1800 converts the combined signal received by the inductor 1606 from the analog domain to the digital domain, and supplies the digital values to the digital signal processor 1802. The digital signal processor 1802, in turn, digitally filters the combined signal to create a plurality of values indicative of amplitude, one for each source signal received. The values indicative of amplitude are then stored in the memory 1704, and when an interrogating signal is received the values indicative of amplitude are supplied to the RFID charger/reader 1108 (FIG. 11) by way of the transmission controller 1728 and transmission antenna 1618.

In yet still other cases, the digital signal processor 1802 may be omitted, and the AD converter 1800 and the memory 1704 may store raw values of the combined signal received by the inductor 1606. In such situations, the raw values are supplied to the RFID charger/reader 1108 (FIG. 11) by way of the transmission controller 1728 and transmission antenna 1618, and the various signals separated and locations determined by the RFID charger/reader 1108 or other downstream devices.

Regardless the specifics of filtering the individual source signals, at the surface the data regarding amplitude of the source signals at the location of the RFID device 1116 is read. Each value indicative of amplitude implies a distance from the EM source that created the source signal. From the value indicative of amplitude a mathematical spherical surface that defines the possible locations of the RFID device 1116 can be calculated. It is the underground intersection of the mathematical surfaces that defines the location of the RFID device 1116 when each set of data is stored to the memory. Moreover, each RFID device may store a plurality of values indicative of the amplitude of the source signals along with an indication of time each plurality of values was read (e.g., the time signal encoded in one of the source signals), and from the plurality of values the movement of the RFID device over time may be determined.

Figure 19:
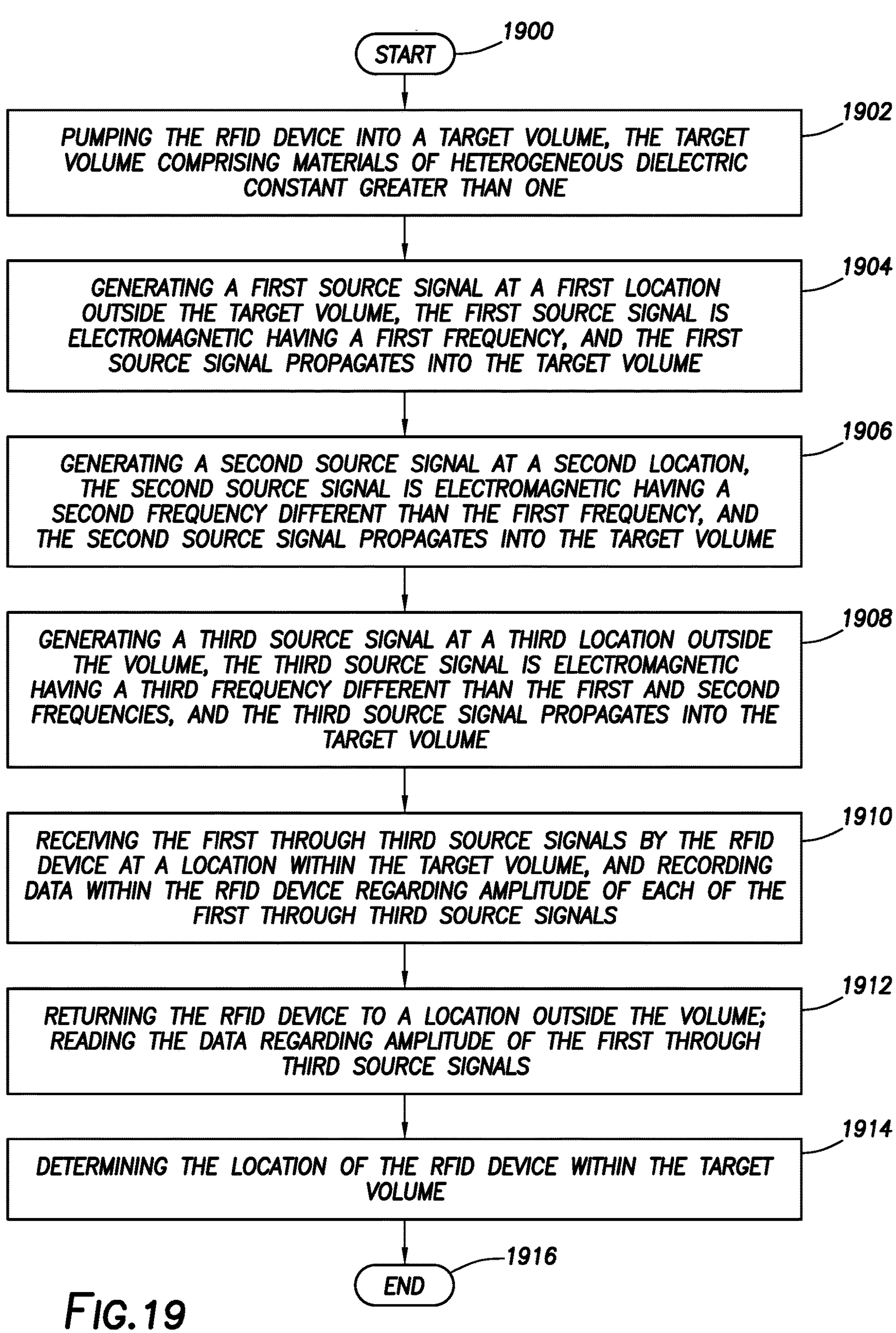
FIG. 19 shows a method in accordance with at least some embodiments.

FIG. 19 shows a method in accordance with at least some embodiments. In particular, the method starts (block 1900) and comprises: pumping the RFID device into a target volume, the target volume comprising materials of heterogeneous dielectric constant greater than one (block 1902); generating a first source signal at a first location outside the target volume, the first source signal is electromagnetic having a first frequency, and the first source signal propagates into the target volume (block 1904); generating a second source signal at a second location, the second source signal is electromagnetic having a second frequency different than the first frequency, and the second source signal propagates into the target volume (block 1906); generating a third source signal at a third location outside the volume, the third source signal is electromagnetic having a third frequency different than the first and second frequencies, and the third source signal propagates into the target volume (block 1908); receiving the first through third source signals by the RFID device at a location within the target volume, and recording data within the RFID device regarding amplitude of each of the first through third source signals (block 1910); and returning the RFID device to a location outside the volume; reading the data regarding amplitude of the first through third source signals (block 1912); and determining the location of the RFID device within the target volume (block 1914). Thereafter, the method ends (block 1916).

The above discussion regarding localization of the RFID devices is meant to be illustrative of the principles and various embodiments. Numerous variations and modifications will become apparent to those skilled in the art once the above disclosure is fully appreciated. For example, while the various embodiments were described as passive devices that harvest electromagnetic energy, the devices could be combined with externally affixed batteries to make active devices that can still be read from distances of a kilometer or more. Moreover, while the example target volume was a hydrocarbon bearing formation, the various embodiments may be used in any suitable environment with the heterogeneous dielectric constant, such as the human body. It is intended that the following claims be interpreted to embrace all such variations and modifications.

Electric Field Charging of RFID Chips

Complementary metal oxide semiconductor (CMOS)-based sensors have been utilized for various applications. However, one limiting factor of sub-millimeters CMOS sensors is the need for a battery, as most sensors rely on a battery to supply power consumption. When battery-powered sensors are deployed in harsh environments with high temperatures, power consumption increases due to the increased leakage current of the electronic junctions at high temperatures. Unfortunately, the battery technology has a long way to go before it can be miniaturized to sub-millimeter dimensions, cost few cents, and operate in temperatures approaching 250° Celcius.

At least some of the various embodiments are directed CMOS sensors in the form of radio frequency identification (RFID) chips or devices that harvest energy wirelessly. More particularly, at least some embodiments are directed to RFID chips that harvest energy responsive to time-varying electric fields (e.g., capacitive coupling) or time varying electrical current flow in proximity of the RFID chip. Example RFID chips for use in non-conductive environments extract or harvest energy from time-varying electric fields permeating the non-conductive environment (e.g., an underground hydrocarbon formation). Using the energy harvested the RFID chip can measure physical parameters in the vicinity of the RFID chip (e.g., temperature), and send the indications of the measured parameters electromagnetically to a reader device either directly or through a communication chain by way of other RFID chips in the vicinity. Further still, example RFID chips for use in conductive environments extract or harvest energy from time-varying electrical currents permeating the conductive environment (e.g., geothermal well, human body). Using the energy harvested from the electrical currents, the RFID chip measures physical parameters in the vicinity of the RFID chip (e.g., temperature, pressure), and send the indications of those parameters by way of the conductive environment.

Figure 20:
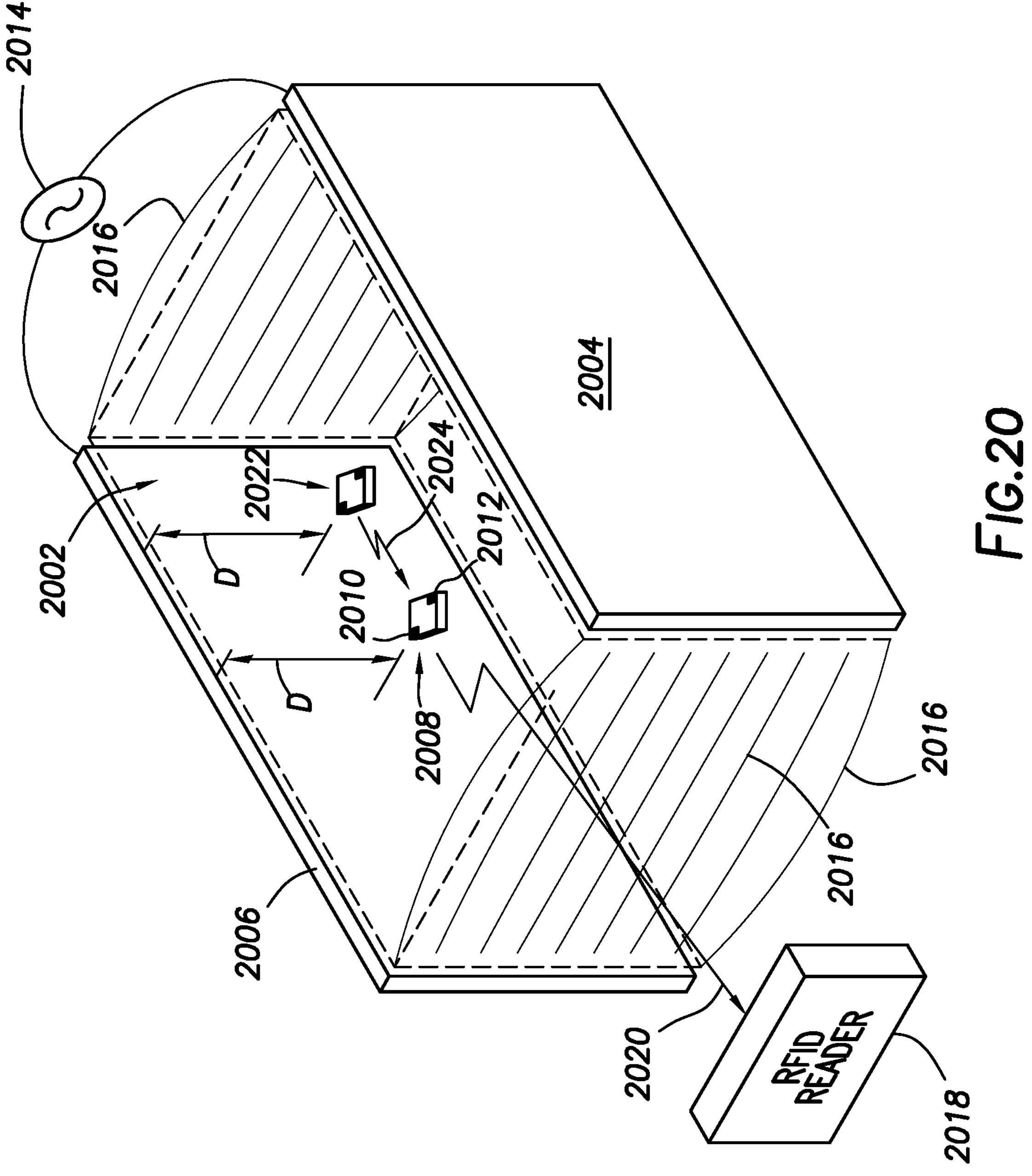
FIG. 20 shows a perspective view of an example environment in accordance with at least some embodiments.

FIG. 20 shows a perspective view of an example environment in accordance with at least some embodiments. In particular, the example system 2000 comprises a sample volume 2002 in the example form of a rectangular cuboid (shown by dashed lines), and the sample volume 2002 of FIG. 20 is a non-conductive environment. For purposes of explanation, the sample volume 2002 is disposed between a first plate 2004 of metallic material and a second plate 2006 of metallic material. Disposed within the sample volume 2002 is an RFID chip 2008 (example structures discussed more below), the RFID chip 2008 comprising a first electrode 2010 of metallic material and a second electrode 2012 of metallic material. As shown, the first and second electrodes 2010 and 2012 are spaced apart from each other on the RFID chip 2008.

RFID chip 2008 (and others like it) may be small enough to travel through the channels in underground formations, such as geothermal well and hydrocarbon formations. Thus, in example embodiments the RFID chip 2008 does not include separately mounted batteries or capacitors as these externally attached devices increase the size and cost of the RFID chip 2008; rather, the RFID chip 2008 is monolithically constructed with onboard capacitance and other devices (e.g., electrodes, antennas) that harvest energy. In the situation of FIG. 20 where the sample volume 2002 is a non-conductive environment, the example RFID device 2008 harvests or extracts energy responsive to an electric field permeating the sample volume 2002. In particular, a time-varying electric field is applied across the sample volume 2002 by applying a time-varying voltage (e.g., sine wave) to the first and second plates 2004 and 2006 by way of voltage source 2014. The time-varying voltage provided by voltage source 2014 thus creates a time-varying electric field between the plates 2004 and 2006 within the sample volume 2002, the electric field illustrated in the static picture of FIG. 20 as electric field lines 2016. The electric field lines are shown only at the ends of the cuboid so as not to unduly complicate the figure, but the electric field would exist at substantially all locations within the sample volume 2002, as well as outside the boundary of the plates 2004 and 2006 based on field fringe effects. The frequency of the voltage applied by the voltage source 2014 depends on the situation, such as the amount of electric field that can be applied across the sample volume 2002 and the energy harvesting efficiency of the RFID chip 2008, but in some cases may range from less than 1 (Hertz) to about 100 Megahertz, and in some cases about 1 kilohertz.

Still referring to FIG. 20, the electric field strength created within the sample volume 2002 also depends on the situation. In some example systems, the voltage applied across the plates 2004 and 2006 creates electric field strength within the sample volume about 1 volt per millimeter (V/mm). In terms of extracting energy from the electric field by the RFID chip 2008, the electric field strength and frequency may be related. That is, if the situation regarding the sample volume 2002 enables application of higher electric field strength, then lower frequency may be used. Conversely, if the situation regarding the sample volume 2002 limits electric field strengths (e.g., size of the sample volume), then higher frequencies may be used to enable sufficient energy extraction from the electric field. More specifically then, energy harvested or extracted from the surrounding electric field by the RFID chip 2008 is proportional to ($f \times E^2$) where f is the frequency of the electric field and E is the magnitude of the electric field. For example, all other things being equal, if the peak voltage applied across a sample volume 2002 is reduced from 100 kilovolts (kV) to 25 kV (e.g., to achieve the 1 V/mm), and the frequency is increased from 1 kHz to 16 kHz, then the RFID chip 2008 should be able to harvest about the same amount of energy.

Although the inventors do not wish to be tied to any particular theory of operation, one possible physical explanation for the ability to extract energy from the electric field is the idea of capacitive coupling of the first and second electrodes 2010 and 2012 to the first and second plates 2004 and 2006. That is, when the electric field is oriented in a first direction, the electric field tends to force free electrons of the metallic material to gather or bunch on one electrode (e.g., the first electrode 2010). As the free electrons migrate to the first electrode 2010, the movement creates voltage within the RFID chip 2008, and the electron flow and voltage represent energy that can be harvested to operate the RFID chip 2008. Once the electric field applied to the sample volume 2002 passes its peak and reverses orientation, the electrons that gathered or bunched on first electrode 2010 then migrate under the force of the electric field to the second electrode 2012, and again the movement creates voltage and current within the RFID chip 2008 that can be harvested to operate the RFID chip 2008. Thus, no electrical current needs to flow from the RFID chip 2008 to the plates 2004 and 2006 for the RFID chip 2008 to be powered thereby—the plates are capacitively coupled through the non-conductive environment of the sample volume 2002. Other equivalent theories of operation are possible.

The example RFID chip 2008 further comprises a sensor (discussed more below) that senses a physical parameter associated with the sample volume 2002, with the sensor utilizing extracted energy. The sensor may be designed and constructed to sense any suitable physical parameter proximate to the RFID chip 2008, such as: temperature; pressure; pH; electrical conductivity; electrical permittivity; magnetic permeability; nuclear magnetic resonance (NMR) spectrum; electron spin resonance (ESR) spectrum; florescence response; porosity; and/or permeability.

Regardless of the type of sensor implemented, in example embodiments the RFID chip 2008 is designed and constructed to broadcast values indicative of the physical parameter. In some cases, the RFID chip 2008 may broadcast responsive to an interrogating signal sent from an RFID reader 2018, the broadcast shown in FIG. 20 by way of an electromagnetic signal 2020. In other cases the RFID chip 2008 may broadcast values indicative of the parameter periodically, without being specifically interrogated (discussed more below). In example systems, the RFID chip 2008 broadcasts the values indicative of the parameter by way of a transmission antenna (discussed more below) at a frequency greater than 1 Gigahertz (GHz), in some cases at about 2.45 GHz, and in other cases at about 1.2 GHz.

Still referring to FIG. 20, the sample volume 2002 may have many RFID chips disposed therein, and for purposes of explanation consider that the sample volume 2002 has a second RFID chip 2022 that is the same or similar in design and construction to RFID chip 2008. Like RFID chip 2008, the RFID chip 2022 may likewise extract energy from the electric field applied to the sample volume 2002, and may measure one or more physical parameters in proximity of the RFID chip 2022. However, consider that the makeup of the sample volume 2002, while non-conductive in this example, nevertheless limits the distance that the RFID chips 2008 and 2022 can transmit or broadcast values indicative of the parameter. Thus, the RFID chip 2022 may be unable to directly communicate with the RFID reader 2018, but RFID chip 2008 (or other RFID chips disposed closer to the RFID reader 2018) is able to directly communicate with the RFID reader 2018. In accordance with example systems, the RFID chips are designed and constructed to relay information from RFID chip-to-RFID chip to communicate data from deep within the sample volume 2002 to the RFID reader 2018. Consider, as an example, that RFID chip 2022 senses a physical parameter of the sample volume using its sensor, and then broadcasts values indicative of the parameter (e.g., the broadcast at 1 GHz or above). Though the electromagnetic signal from RFID chip 2022 may not be able to reach the RFID reader 2018, example RFID chip 2008 may be close enough to receive the broadcast, as shown by electromagnetic signal 2024. In accordance with example embodiments, the RFID chip 2008 receives the values indicative of the parameters sensed by the RFID chip 2022 (and likely also receives a value identifying the RFID chip 2022 and/or its location), and re-broadcasts the values indicative of the parameter (and other identifying/location information) using the transmission antenna. The next RFID chip disposed within the sample volume receives the values indicative of the parameters, and re-broadcasts, and so on until the data reaches the RFID reader 2018.

Figure 21:
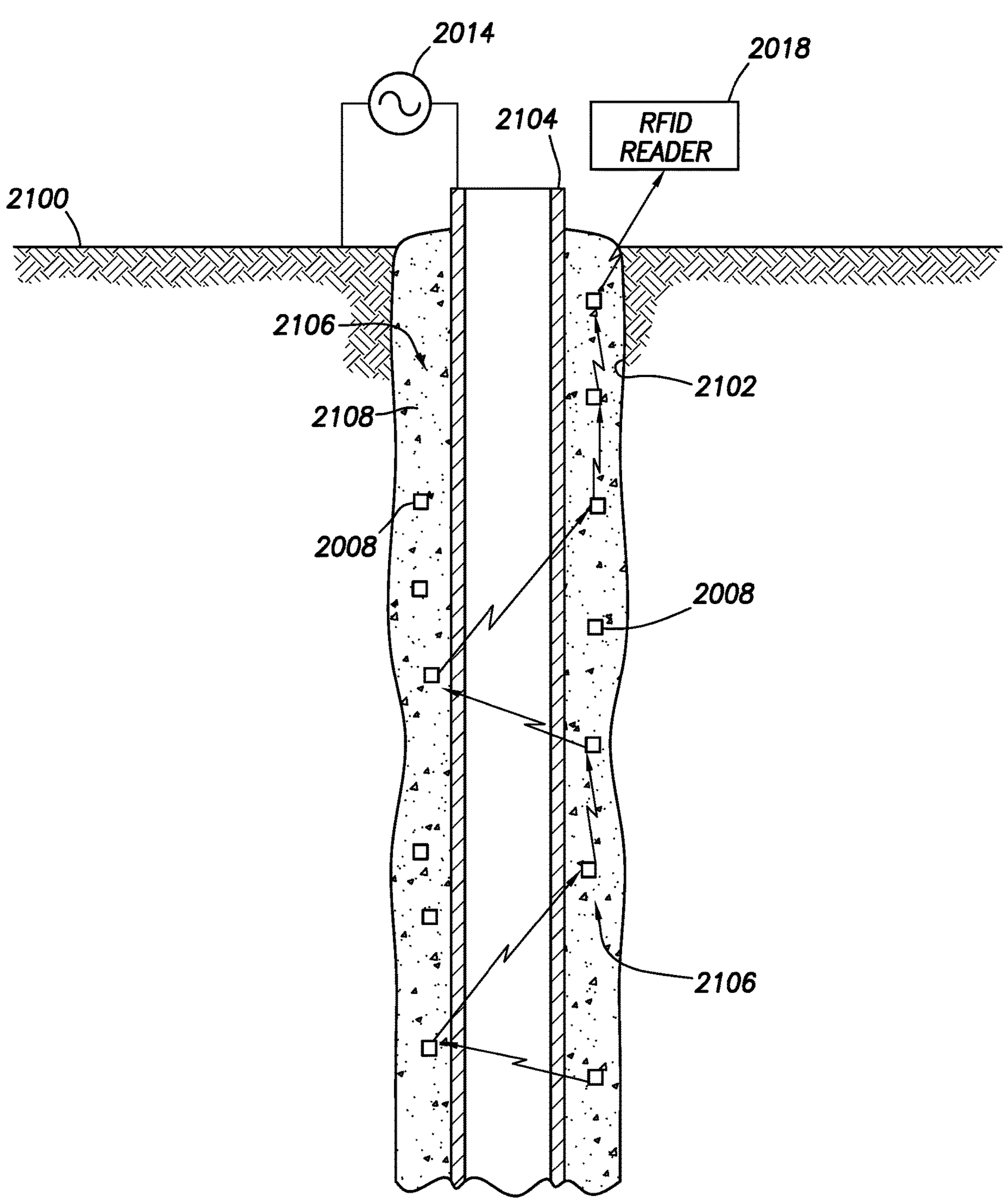
FIG. 21 shows a cross-sectional view of a borehole and cemented in accordance with at least some embodiments.

FIG. 20 discusses a sample volume 2002 (and extracting energy from an applied electric field) in a generic system for purposes of explanation. FIG. 21 shows a cross-sectional view of a borehole and cemented casing to describe a more specific example embodiment. In particular, visible in FIG. 21 is the surface 2100 of the Earth. A borehole 2102 has been drilled, and disposed within the borehole is casing 2104 of metallic material. An annulus 2106 is defined between the outside surface of the casing 2104 and the borehole 2102, and the annulus is filled with cement 2108. A cementing operation involves pumping the cement through the center of the casing 2104, and then forcing the cement 2108 from out the bottom of the casing and up through the annulus 2106. In accordance with example embodiments a plurality of RFID chips as described above (and below) are entrained within the cement 2108 such that the RFID chips are periodically spaced throughout the cement 2108. Although cement may initially be conductive (e.g., wet cement may have a conductivity of about 2.0 S/m), as the cement cures the conductivity drops (e.g., after several hours to less than 1.0 S/m, sometimes 0.5 S/m). Thus, the cement is a sample volume, and at some point in the curing processing the cement may be considered a non-conductive environment as defined above. In the example situation of FIG. 21, the RFID chips 2008 (not all the RFID chips are specifically numbered, but are generally shown as squares) may extract energy responsive to an electric field within the cement. That is, in the example system a voltage is applied between the casing 2104 and the borehole 2102 wall (i.e., ground) by voltage source 2014. The voltage source 2014 thus creates a time-varying electric field in the cement, and in accordance with various embodiments the RFID chips 2008 extract energy from the electric field. Given that the casing is relatively close to the borehole (e.g., within a few inches), the electric field that can be created in the cement may be relatively high, and thus as discuses above the frequency of the time-varying electrical field may be relatively low (e.g., 1 Hz or less). Each RFID chip 2008 may read a parameter of the cement proximate to the RFID chip 2008 (e.g., temperature). The parameters read may give indications as how well the cement is distributed and how well the cement has bonded to the casing and borehole.

Still referring to FIG. 21, RFID chips close to the surface may be able to broadcast values indicative of the parameters directly to the RFID reader 2018 disposed at the surface; however, RFID chips at greater depths within the borehole (here depth measured from the surface 2100) may be unable to directly communicate with the RFID reader 2018. Thus, as discussed generically with the respect to FIG. 20, in the example systems the RFID chips not only broadcast their respective sets of data, but also receive and re-broadcast values from RFID chips deeper in the borehole, all powered by the time varying electric field within the cement as created by the voltage source 2014. Any suitable communication protocol may be used to control the flow of data values up the annulus toward the surface. For example, the location of each RFID chip is directly related to the point in time when the RFID chip entered the casing 2104 as part of the cementing operation, with the first portion of cement that enters the casing ultimately being the cement closest to the surface 2100 in the annulus 2106, and the last portion of cement that enters the casing 2104 being the cement deepest in the borehole 2102. Thus, as the cement and entrained RFID chips are being pumped into the casing, the RFID chips may be programmed by the RFID reader 2018 with identification values that identify the expected ultimate depth in the borehole. The RFID chips may also each have their own unique identifier. With the combination of the depth identifier and the unique identifier, data can be associated with the particular depth. Moreover, the RFID chips can be programmed to recognize signals that emanate from deeper within the borehole (e.g., from the next depth level), and only re-broadcast data received from RFID chips deeper in the borehole.

Figure 22:
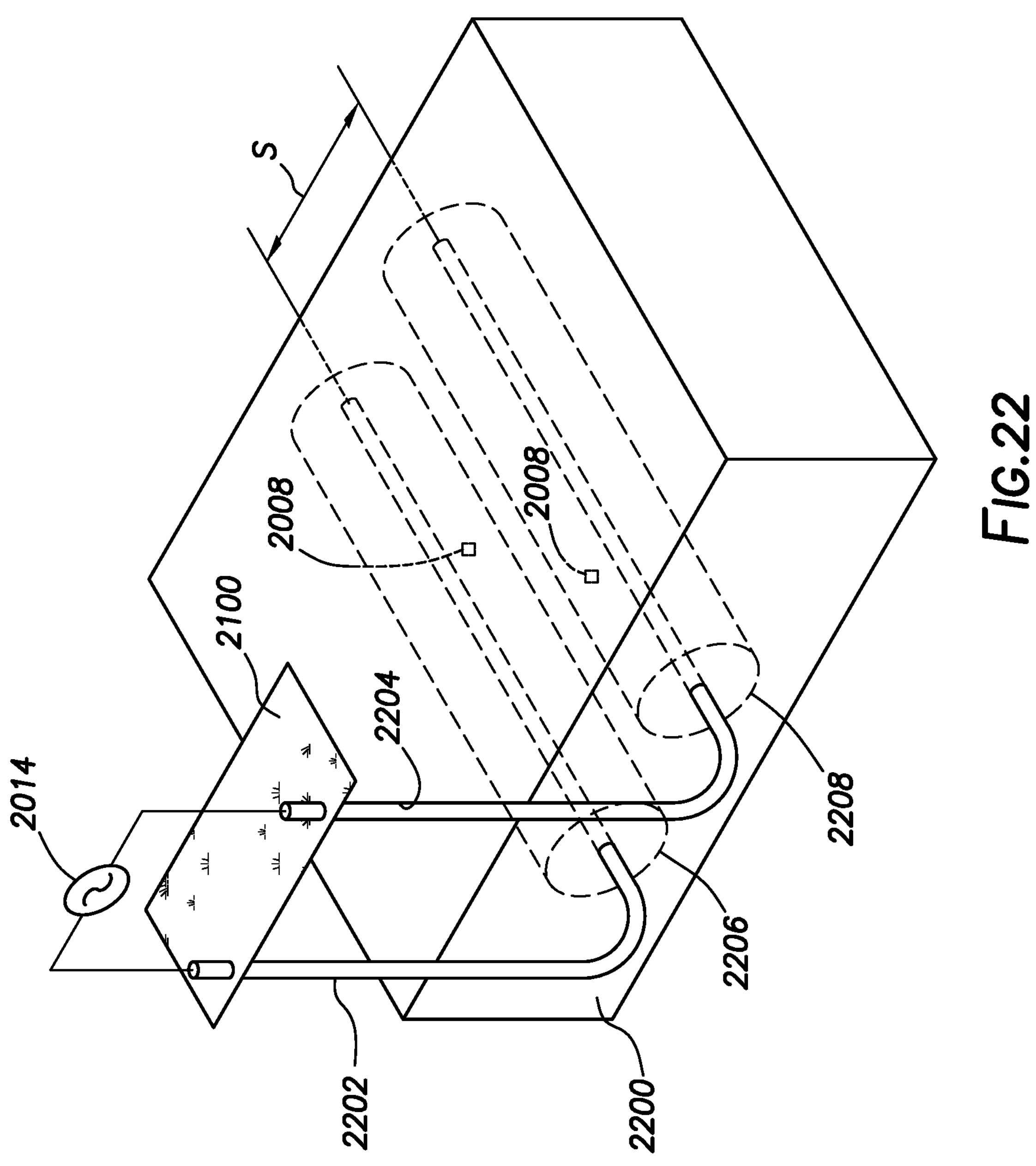
FIG. 22 shows a perspective, partial cut-away view, of a set of hydrocarbon wells in accordance with at least some embodiments.

FIG. 22 shows a perspective, partial cut-away view, of a set of hydrocarbon wells to describe a further more specific example embodiment. In particular, visible in FIG. 22 is the surface 2100 of the Earth. Below the surface 2100 is a hydrocarbon-bearing formation 2200 (hereafter just underground formation or formation 2200). The depth between the surface 2100 and the formation 2200 varies from location-to-location, but in many cases will be between 2000 and 20000 feet. Between the surface 2100 and the hydrocarbon-bearing formation 2200 resides several thousand feet of overburden (the overburden not specially shown so as not to unduly complicate the figure). The example system further comprises a casing 2202 that extends within a borehole (not specifically shown) from the surface 2100 into the formation 2200, with the horizontal portion of the casing 2202 in many cases directionally drilled so as to follow the contours of the formation 2200 (e.g., the contours of a shale formation, though no contours specifically shown). In situations where the formation 2200 is a shale formation, in order to economically extract hydrocarbons many times a series of boreholes are drilled in parallel within the formation, and thus the example system further comprises a second casing 2204 that extends within a borehole (not specifically shown) from the surface 2100 into the formation 2200, with the horizontal portion of the casing 2204 parallel to the horizontal portion of the casing 2202.

Further, in order to economically extract hydrocarbons, the formation 2200 may be hydraulically fractured using specially designed fluids with proppant material entrained therein. The hydraulic fracturing through casings 2202 and 2204 creates fracture zones 2206 and 2208, respectively, with the outer boundaries of the fracture zones defined at the farthest radial extent of the fractures from the respective borehole or casing. In accordance with example embodiments, the fracturing fluid includes not only proppant materials, but also RFID chips 2008 as discussed with respect to FIG. 20. Thus, the formation 2200, and more specifically portions of the fracture zones 2206 and 2208 may be considered a sample volume into which RFID chips are placed, such as during the hydraulic fracturing. Moreover, hydrocarbons generally have a low conductivity, and thus the formation 2200 and/or fracture zones 2206 and 2208 may be considered a non-conductive environment.

In the example situation of FIG. 22, the RFID chips 2008 extract energy responsive to an electric field within formation. That is, in the example system a voltage is applied between the casing 2202 and the spaced-apart casing 2204 by voltage source 2014. The voltage source 2014 thus creates a time-varying electric field in the formation between the casing (including between the horizontal portions of the casing), and in accordance with various embodiments the RFID chips 2008 extract energy from the electric field. The distance between the horizontal portions of the casings depends on the formation and extent of the hydraulic fracturing. In an example case, with spacing S between the horizontal portions of the casing of about 50 meters, voltage source 2014 may apply a time-varying voltage of about 100 kV at a frequency of about 1 kHz. In other situations, the voltage source 2014 may apply about 50 kV between the casings at a frequency of 16 kHz. Each RFID chip 2008 may thus extract energy from the electric field, and using the harvested energy power the sensor to read a parameter of the formation and store the parameter in nonvolatile memory within the RFID chip 2008. Moreover, the reading and storing of the values indicative of the parameter may take place on several occasions as the RFID chip 2008 moves into the formation, and thus the RFID chips 2008 may contain data to help map the fracture network within the formation.

The RFID chips 2008 of FIG. 22 are described in the context of being entrained in the hydraulic fracturing fluid, and thus may be expected to return to the surface during the flow back operations as discussed above. Thus, in some cases the RFID chips 2008 are interrogated by an interrogating signal when returned to the surface, and at that point the RFID chips 2008 may provide information to the RFID reader 2018 (not shown in FIG. 22). In other cases, however, the RFID chips 2008 may be designed and constructed with the expectation of remaining in the formation (e.g., the RFID chips have a largest dimension on the order of the proppant material (about 400 microns to few millimeters)) such that it is expected that some of the RFID chips 2008 will remain lodged in the formation during the flow-back procedures. In such cases, the RFID chips 2008 may implement the receive and re-broadcast techniques discussed above as a mechanism to read the data stored on the chip (e.g., values indicative of physical parameters read by sensors of the chip). In such cases an interrogating antenna of the RFID reader 2018 may be placed within the casing (but likely outside the production tubing) such that the interrogating antenna may be close to the perforations (not specifically shown) and the fracture zones. In another case, the RFID reader may use the casing as an antenna to read the signals of the RFID devices coupled to the casing.

Figure 23:
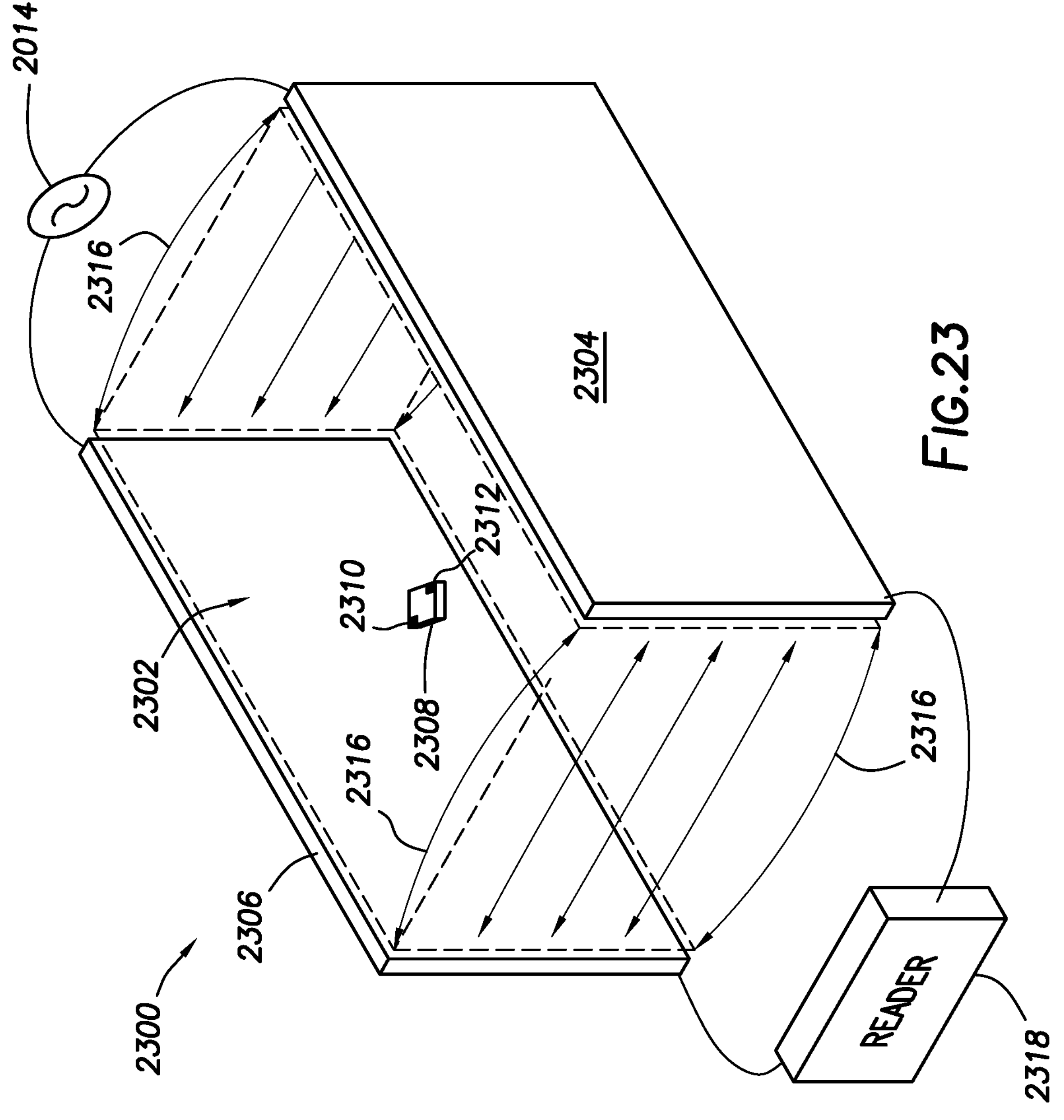
FIG. 23 shows a perspective view of an example environment in accordance with at least some embodiments.

FIG. 23 shows a perspective view of an example environment in accordance with at least some embodiments. In particular, the example system 2300 comprises a sample volume 2302 in the form of a rectangular cuboid (shown by dashed lines), and the sample volume 2302 of FIG. 23 is conductive environment. For purposes of explanation, the sample volume 2302 is disposed between a first plate 2304 of metallic material and a second plate 2306 of metallic material. Disposed within the sample volume 2302 is an RFID chip 2308 (example structures discussed more below), the RFID chip 2308 comprising a first electrode 2310 of metallic material and a second electrode 2312 of metallic material. As shown, the first and second electrodes 2310 and 2312 are spaced apart from each other on the RFID chip 2308.

In accordance with example embodiments, RFID chip 2308 (and others like it) may be small enough to travel through the channels in underground formations, such as geothermal well and hydrocarbon formations. Thus, the example RFID device 2308 does not include separately mounted batteries or capacitors as these externally attached devices increase the size and cost of the RFID chip 2308; rather, the RFID chip 2308 is monolithically constructed with onboard capacitance and other devices (e.g., electrodes, antennas) that harvest energy. In the example situation of FIG. 23 where the sample volume 2302 is a conductive environment, the example RFID device 2308 harvests or extracts energy responsive to electrical current flow permeating the sample volume (which current flow is caused by an applied electric field). In particular, a time-varying electric field is applied across the sample volume 2302 by applying a time-varying voltage (e.g., sine wave) to the first and second plates 2304 and 2306 by way of voltage source 2314. The time-varying voltage provided by voltage source 2314 thus induces time-varying electrical current, illustrated in the static picture of FIG. 23 as lines of current 2316 (not all the current lines specifically marked). The electrical current lines are shown only at the ends of the cuboid so as not to unduly complicate the figure, but such electrical current would exist at substantially all locations as function of the distribution of conductance through the sample volume. The frequency of the voltage applied by the voltage source 2314 depends on the situation, such as the amount of electrical current the sample volume 2302 can support without undue resistive heating and/or vaporization. In some cases, the frequency of the time-varying current flow may be less than 1 (Hertz) to about 100 Megahertz, and in some cases about 1 kilohertz.

Still referring to FIG. 23, in accordance with example systems, the electrical current flow through the sample volume 2302 creates a spatial voltage drop of about 1 V/mm. Given that the RFID chip 2308 resides within the sample volume 2302 and the RFID chip 2308 extends for a finite distance along a line normal to the plates 2304 and 2306, the spatial voltage drop may be used by the RFID chip to harvest or extract energy.

The example RFID chip 2308 further comprises a sensor (discussed more below) that senses a parameter associated with the sample volume 2302, with the sensor powered utilizing extracted energy. The sensor may be designed and constructed to sense any suitable parameter of interest proximate to the RFID chip 2308, such as: temperature; pressure; pH; electrical conductivity; electrical permittivity; magnetic permeability; nuclear magnetic resonance (NMR) spectrum; electron spin resonance (ESR) spectrum; florescence response; porosity; and/or permeability.

In some embodiments, the electrical current flow through the sample volume powers the RFID chip 2308 while the RFID chip 2308 is within the sample volume 2302, and the data gathered by the RFID chip 2308 is read by an RFID reader as the RFID chip 2308 is removed from the sample volume 2302. For example, near a point where RFID chip 2308 exits the sample volume 2302, or any time after the RFID chip 2308 is outside the sample volume, an RFID reader may interrogate the RFID chip 2308, and the RFID chip 2308 broadcasts its stored data (e.g., values indicative of the parameter read by the sensor) at a predetermined frequency, in some cases the broadcast at a frequency of 1 GHz or above.

In additional to or in place of reading the RFID chip 2308 by way of the RFID chip 2308 broadcasting at a frequency of 1 GHz or above, the example RFID chip 2308 is designed and constructed to communicate its stored values by inducing an electrical current flow within sample volume 2302. More particularly, the example RFID chip 2308 may create a time-varying voltage with a predetermined frequency between two electrodes on the RFID chip 2308. The electrodes on which the RFID chip 2308 induces the time-varying voltage may be electrodes 2310 and 2312, or may be separate electrodes specifically dedicated to communicate within the conductive environment (discussed more below). The voltage applied to the electrodes creates an electric field and induces a current flow within the conductive medium. The voltage and/or electrical field created by the RFID chip 2308 may be detected by a reader system 2318 electrically coupled to the conductive sample volume. Any suitable modulation scheme may be used (e.g., each RFID chip having a different frequency, each RFID chip using the same modulation scheme but with individual identification numbers, spread spectrum communication, code division multiplexing, and the like). In most cases, the frequency of the time-varying voltage created by the RFID chip 2308 (and thus the time varying electrical current between the electrodes) will be different than the frequency of the voltage applied to the plates 2304 and 2306 to create the time-varying current within the sample volume 2302 and from which energy is harvested. Nevertheless, the reader system 2318 detects and decodes the transmission to extract the values indicative of the parameter read by the sensor. Thus, the RFID chips 2308 need not be removed from the sample environment to be read, even in the case where the RFID chip 2308 cannot broadcast its data by way of an electromagnet wave propagating through the conductive sample volume to a reader or to other RFID chips 2308. The RFID chips 2308 may also utilize the receive and re-broadcast techniques discussed above in certain situations, but the conductivity of the sample volume 2302 may limit the distance over which the RFID chips can communicate at frequencies of 1 GHz and above.

Figure 24:
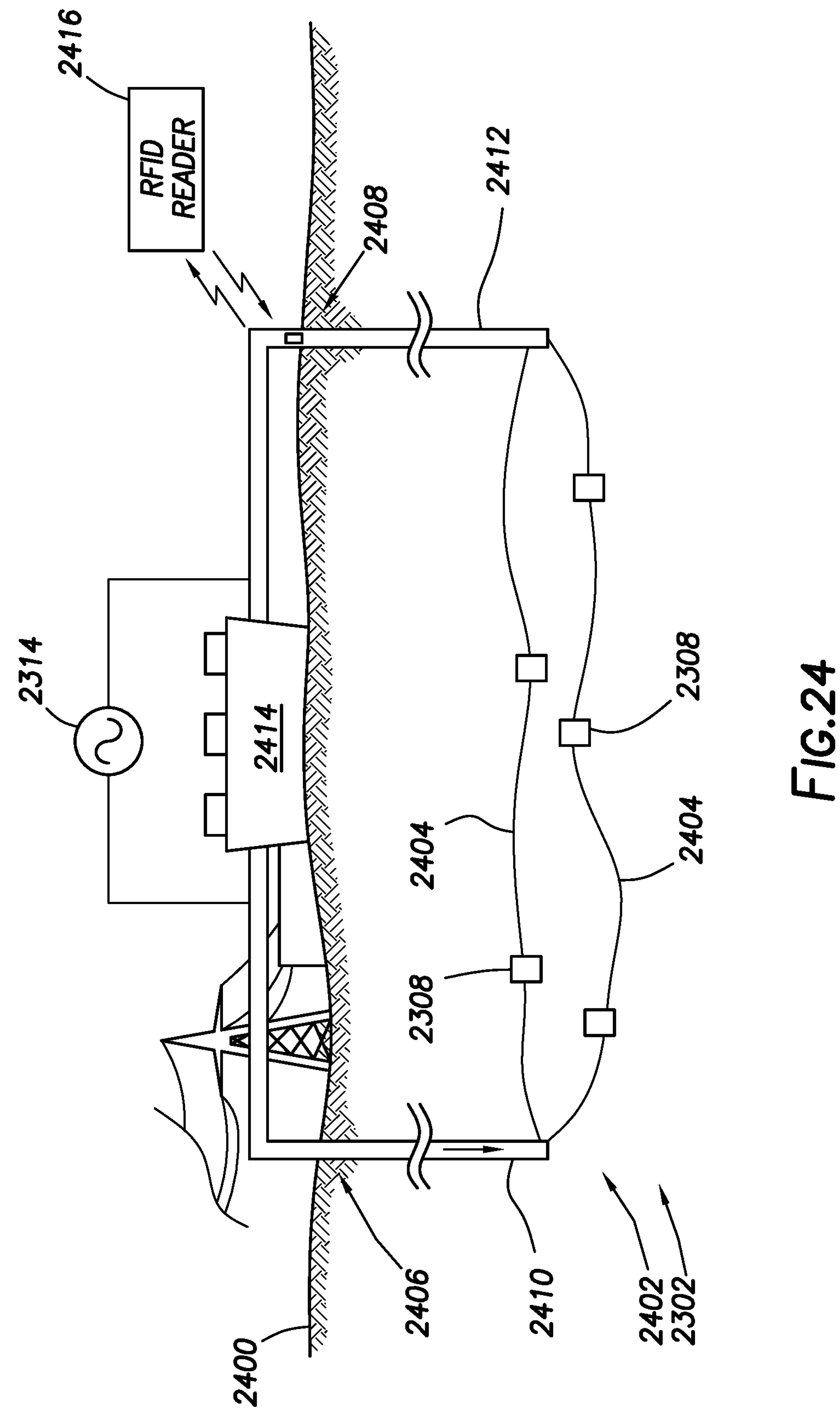
FIG. 24 shows a cross-sectional, partial block diagram, view of a geothermal operation in accordance with at least some embodiments.

FIG. 23 discusses a sample volume 2302 (and extracting energy from electric current flowing therein) in a generic conductive environment for purposes of explanation. FIG. 24 shows a cross-sectional, partial block diagram view of a geothermal operation to describe a specific example embodiment. In particular, shown in the FIG. 24 is the surface 2400 of the Earth. At some distance below the surface is a geothermal formation 2402 having a plurality of hydrofractures 2404 therein (only two hydrofractures shown so as not to unduly complicate the figure). The hydrofractures 2404 extend between an injection well 2406 and a production well 2408. The injection well 2406 has a casing 2410 of metallic material, and likewise the production well 2408 has a casing 2412 of metallic material. In the example geothermal context, the hydrofractures 2404 may pass through a geologically active region having magma near the surface, and in operation the overall system of FIG. 24 may heat water by injecting the water into the injection well 2406, forcing the water through hydrofractures 2404 in which the water temperature is increased, and then producing the water by way of the production well 2408. The example plant 2414 may use the heated water for any suitable purpose, such as steam production generating electricity or space heating.

In the example embodiments of FIG. 24, the geothermal formation 2402 between the casings 2410 and 2412 is a sample volume 2302 comprising a conductive environment. In order to gauge the efficiency of the operation, for example, the water that flows through the geothermal formation 2402 may have RFID chips 2308 entrained therein (only a few of the RFID chips are specifically numbered, but the RFID chips are illustrated as rectangles). Thus, the RFID chips 2308 may be injected through the injection well 2406, flow through the hydrofractures 2404, and arrive again at the surface by way of the production well 2408. It follows from the discussion above that the RFID chips may be powered within the geothermal formation 2402 by extracting energy responsive to an electric field applied across the conductive formation, and more specifically by extracting energy from electric current flow through the geothermal formation 2402 flowing between the casings 2410 and 2412. That is, in the example situation of FIG. 24 a time-varying electric field is applied across the geothermal formation 2402 by applying a time-varying voltage (e.g., sine wave) across the casings 2410 and 2412 (as shown by voltage source 2314 by way of voltage source 2314). The time-varying voltage provided by voltage source 2314 thus induces time-varying electrical current through the geothermal formation 2402. The frequency of the voltage applied by the voltage source 2314 depends on the situation, and in some cases the frequency may be less than 1 (Hertz) to about 100 Megahertz, and in some cases about 1 kilohertz.

Still referring to FIG. 24, for spacing between the injection well 2406 and the production well 2408 of about 50 m, the voltage source 2314 may apply a time-varying voltage of about 50 kV to 100 kV in order to produce a spatial voltage drop of about 1 V/mm. As before, the applied voltage may be reduced if the frequency of the time varying voltage is increased. The example RFID chips 2308 of FIG. 24 each comprise a sensor, and in the example case of the geothermal formation 2402 the sensors may be temperature sensors. Although it may be possible to read data from the RFID chips 2308 that reside within the geothermal formation 2402 using the voltage sensing techniques discussed above, in the particular situation it is expected that an RFID reader 2416 is disposed at the surface to send an interrogating signal to the RFID chips at or near the surface (e.g., interrogating signal at above 1 GHz, and in some case about 2.45 GHz) and receive back from each RFID chip 2308 values indicative of the parameter by way of a signal broadcast above 1 GHz, such as 1.2 GHz.

Figure 25:
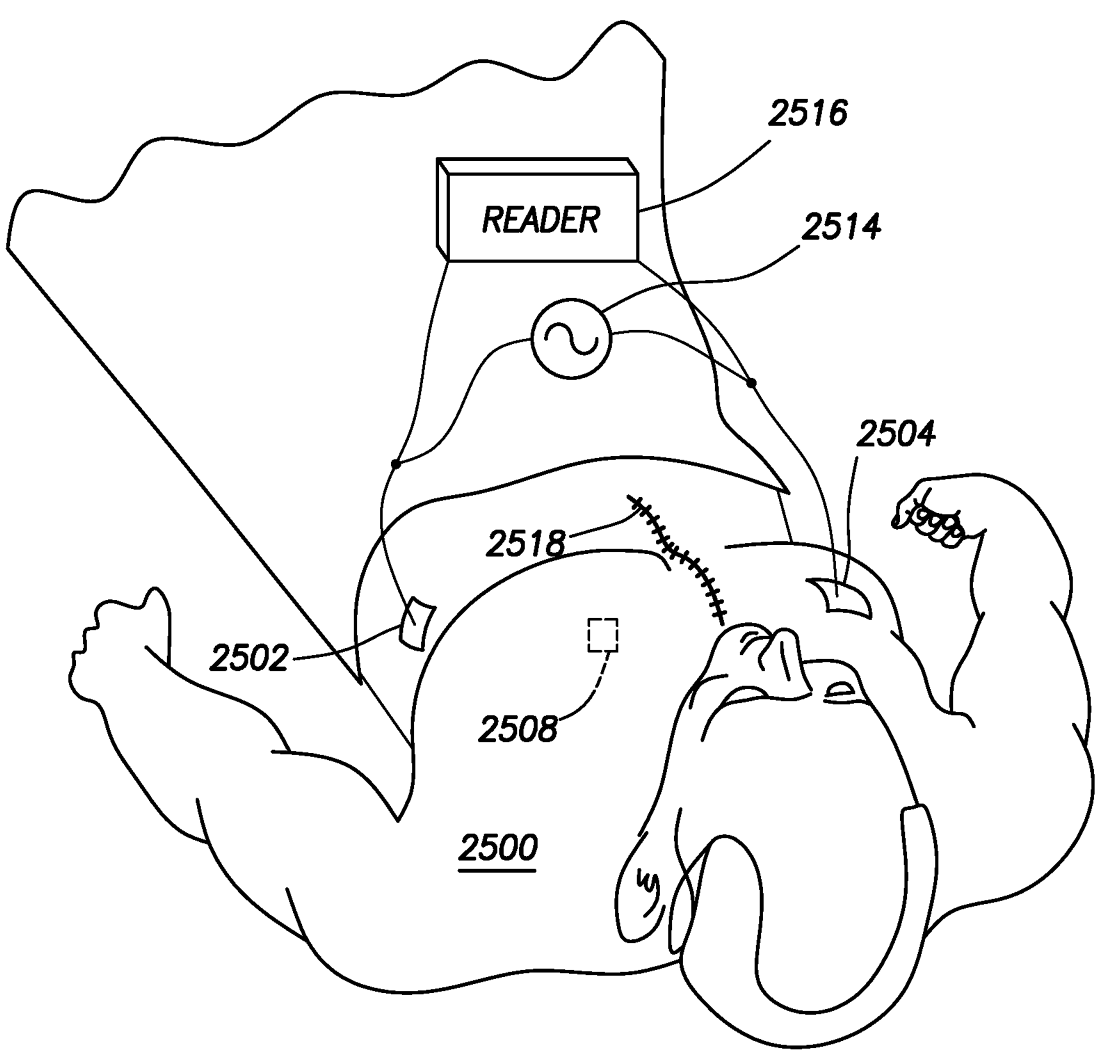
FIG. 25 shows a perspective view of a person in accordance with at least some embodiments.

FIG. 25 shows a perspective view of a person to describe another example embodiment. In particular, in the example situation of FIG. 25 the sample volume is the organic tissue of a human body 2500, and in this example the sample volume is the chest cavity. The example system comprises electrodes 2502 and 2504 on the patient's skin. Disposed within the chest cavity is an RFID chip 2508 (example structures discussed more below), the RFID chip 2508 including electrodes as discussed above, but not specifically shown.

In accordance with example embodiments, RFID chip 2508 may be small enough to travel through the circulatory system, or the RFID chip 2508 may be placed at a particular location (e.g., aorta, right ventricle, left ventricle), such as through incision 2518 during open heart surgery. As before, in example systems the RFID chip 2508 does not include separately mounted batteries or capacitors; rather, the RFID chip 2508 is monolithically constructed with onboard capacitance and other devices (e.g., electrodes, antennas) that harvest energy. In the example situation of FIG. 25 where the sample volume is the chest cavity of a human body, the environment is a conductive environment. Thus, as before the example RFID chip 2508 harvests or extracts energy responsive to electrical current flow permeating the sample volume. In particular, a time-varying electric field is applied across the chest cavity of the human body 2500 by applying a time-varying voltage (e.g., sine wave) to the electrodes 2502 and 2504 by way of voltage source 2514. The time-varying voltage provided by voltage source 2514 thus induces a small time-varying electric current through the chest cavity. The frequency of the applied voltage depends on the situation, but in some cases, the frequency of the time-varying current flow may be less than 1 (Hertz) to about 100 Megahertz, and in some cases about 1 kilohertz to about 100 kilohertz.

The example RFID chip 2508 further comprises a sensor (not specifically shown) that senses a parameter proximate to the RFID chip 2508, with the sensor powered utilizing extracted energy. The sensor may be designed and constructed to sense any suitable parameter of interest proximate to the RFID chip 2508, such as: temperature; pressure; pH; and electrical conductivity. In some embodiments, the electrical current flow through the sample volume powers the RFID chip 2508 while the RFID chip 2508 is within the chest cavity, and the data gathered by the RFID chip 2508 is read by an RFID reader as the RFID chip 2508 is removed. In additional to or in place of reading the RFID chip 2508 once removed, the example RFID chip 2508 is designed and constructed to communicate its stored values by inducing an electrical current flow within chest cavity between two electrodes. More particularly, the example RFID chip 2508 may create a time-varying voltage with a predetermined frequency between two electrodes on the RFID chip 2508. The voltage applied to the electrodes creates an electric field and induces a current flow within the conductive medium. The voltage and/or electrical field created by the RFID chip 2508 may be detected by a reader system 2516 electrically coupled to the conductive environment. The RFID chip 2508 may also utilize the receive and re-broadcast techniques discussed above in certain situations, but the potentially detrimental physiological effects and/or the conductivity of the organic tissue may severely limit the distance over which the RFID chips can communicate at frequencies of 1 GHz and above.

Figure 26:
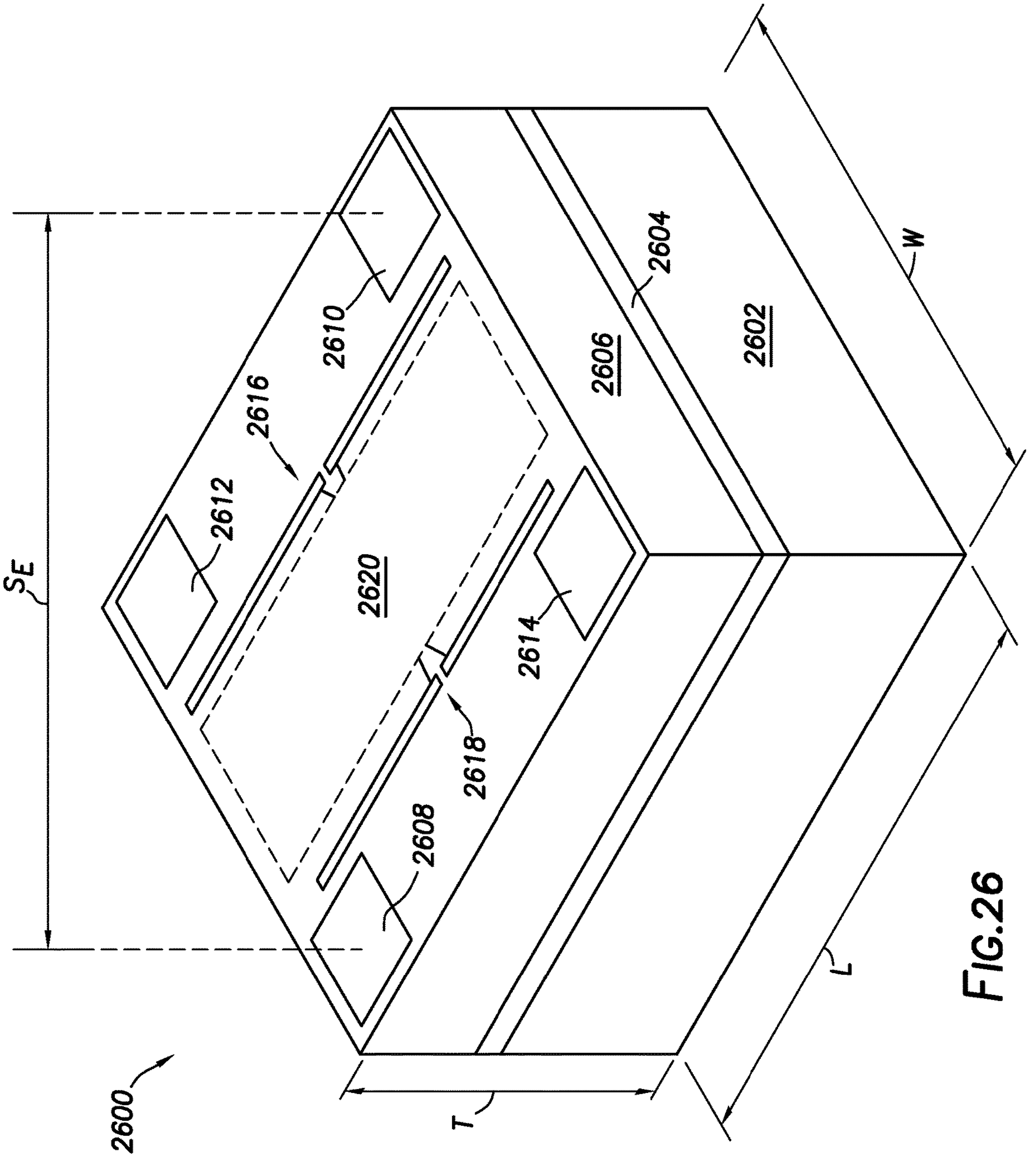
FIG. 26 shows a perspective view of an RFID chip in accordance with at least some embodiments.

FIG. 26 shows a perspective view of an RFID chip 2600 in accordance with at least some embodiments. In particular, the example RFID chip 2600 could be any of the previously discussed RFID chips (e.g., 2008, 2308, 2508). The example RFID chip 2600 comprises a substrate 2602. In many cases the substrate 2602 is made of silicon, but other substrates are also possible. Constructed upon the substrate 2602 are the various circuits, antennas, and sensors. In some cases, particularly for high temperature operation (e.g., hydrocarbon formations, geothermal wells) an insulator 2604 separates the substrate 2602 from an active area 2606 (i.e., a silicon-on-insulator (SOI) construction). However, in other cases the components of the active area 2606 are built directly on the substrate 2602 and thus no delineation (other than perhaps depth) may be present. The RFID chip has a thickness T, a width W, and length L. The relative thicknesses of the layers along the thickness T are not shown to scale in the figure, nor are the width and length. Nevertheless, in example systems the substrate 2602 may have a thickness of about 300 microns, the insulator 2604 may have a thickness of about 1 to 10 microns, and the active area 2606 may have a thickness of about 10 to 100 microns depending on specific design criteria for the chip. Thus, the overall RFID chip 2600 may have a thickness T of 400 microns or less (measured perpendicular to the substrate 2602). In some cases, the RFID chip 2600 may have a thickness T of about 300 microns or less. Further in example systems, the RFID chip 2600 may have a length L of 400 microns or less, and a width W of 400 microns or less, as L and W are depicted in FIG. 26 (i.e., measured in a plane parallel to the substrate 2602). In yet still further embodiments, the largest external dimension of the RFID chip 2600 (i.e., the longest of any one of T, L, and W in FIG. 26) may be a few millimeters to 400 microns or less.

Visible on the upper surface of the example RFID chip 2600 are several components. In particular, shown on the upper surface are a plurality of electrodes 2608, 2610, 2612, and 2614. Each electrode is defined on the substrate 2602 and exposed on the outer surface of the RFID chip 2600. Each electrode is a metallic material. Electrode 2608 is disposed in a first corner of the device, and electrode 2610 is disposed in an opposite corner of the device. The example placements of electrodes 2608 and 2610 provide longest spacing of the electrodes. As shown, the spacing $S_E$ between electrodes 2608 and 2610 (measured center-to-center) is longer than the length L. Regardless of whether the energy extraction is by way of an electric field or based on current flow near the RFID chip 2600, longer spacing provides better performance. While the electrodes 2608 and 2610 are placed in opposite corners, such is not required, and other placements are possible. In some cases, the spacing $S_E$ between the electrodes is at least half the width W (where width W is the smaller of the two non-thickness dimensions).

Likewise, electrode 2612 is disposed in a corner of the device, and electrode 2614 is disposed in an opposite corner of the device. The example placements of electrodes 2612 and 2614 again provide longest spacing of the electrodes, with similar spacing $S_E$ (not specifically shown in the figure). The second set of electrodes 2612 and 2614 may also be used to extract energy, or may be used to communicate with the reader by driving voltages across the electrodes 2612 and 2614, and thus inducing an electrical current flow. While the electrodes 2612 and 2614 are placed in opposite corners, such is not required, and other placements are possible.

Still referring to FIG. 26, the example RFID chip 2600 further comprises a power antenna 2616 on the substrate, the power antenna 2616 in the form of a half-wave dipole antenna. In example systems the power antenna 2616 has a resonant frequency above 1 MHz, and in some cases the power antenna 2616 has a resonant frequency of 2.45 Gigahertz. As the name implies, the power antenna 2616 is used by the RFID chip 2600 to harvest or extract electromagnetic energy (at or near the resonant frequency) to power the RFID chip 2600 when in the proximity of reader (e.g., RFID reader 2018), in many cases after having been removed from the sample volume. In some cases, the same electromagnetic signals received by the power antenna 2616 that power the RFID chip can carry coded signals to trigger the RFID chip 2600 to transmit encoded data back to the reader. For example, when the RFID chip 2600 is being pumped downhole in a hydraulic fracturing operation, an RFID reader may broadcast electromagnetic energy having a frequency above 1 MHz but with no encoded data. The RFID chip 2600, in turn, receives the electromagnetic energy by way of power antenna 2616 and stores the energy for later use, but does not trigger transmission of the recorded data because the absence of encoded data in the interrogating signal (or at least not the encoded data that triggers a data transfer). By contrast, as the RFID chip 2600 is flowing back to the surface out, RFID reader 2018 may broadcast electromagnetic energy including encoded data that triggers data transfer.

The example RFID chip 2600 further comprises a transmission antenna 2618 on the substrate, the transmission antenna 2618 also in the form of a half-wave dipole antenna. In example systems, the transmission antenna 2618 has a resonant frequency above 1 MHz, and in some cases the transmission antenna 2618 has a resonant frequency of about 1.2 GHz. As the name implies, the transmission antenna 2618 is used by the RFID chip 2600 to transmit data stored in the RFID chip 2600 back to the RFID reader, the data including values indicative of physical parameters measured by the sensor of the RFID chip 2600. The frequency of transmission by the transmission antenna 2618 is illustratively lower than the frequency at which the RFID chip 2600 harvests or extracts energy by way of the power antenna 2616 to make detection by the RFID reader easier. In further example systems, the frequency at which the transmission antenna 2618 operates may be the same as or higher than the frequency at which the power antenna 2616 extracts energy.

Finally, FIG. 26 shows generically that the RFID chip 2600 contains various other electrical components within area 2620 (discussed in greater detail below). Again, it is noted that the drawing of FIG. 26 is not to scale. Moreover, the relative placement electrodes 2608, 2610, 2612, and 2614 visible in the figure, along the antennas 2616 and 2618, and other components in area 2620 are merely an example, and should not be read to limit the physical layout to what is shown.

Figure 27:
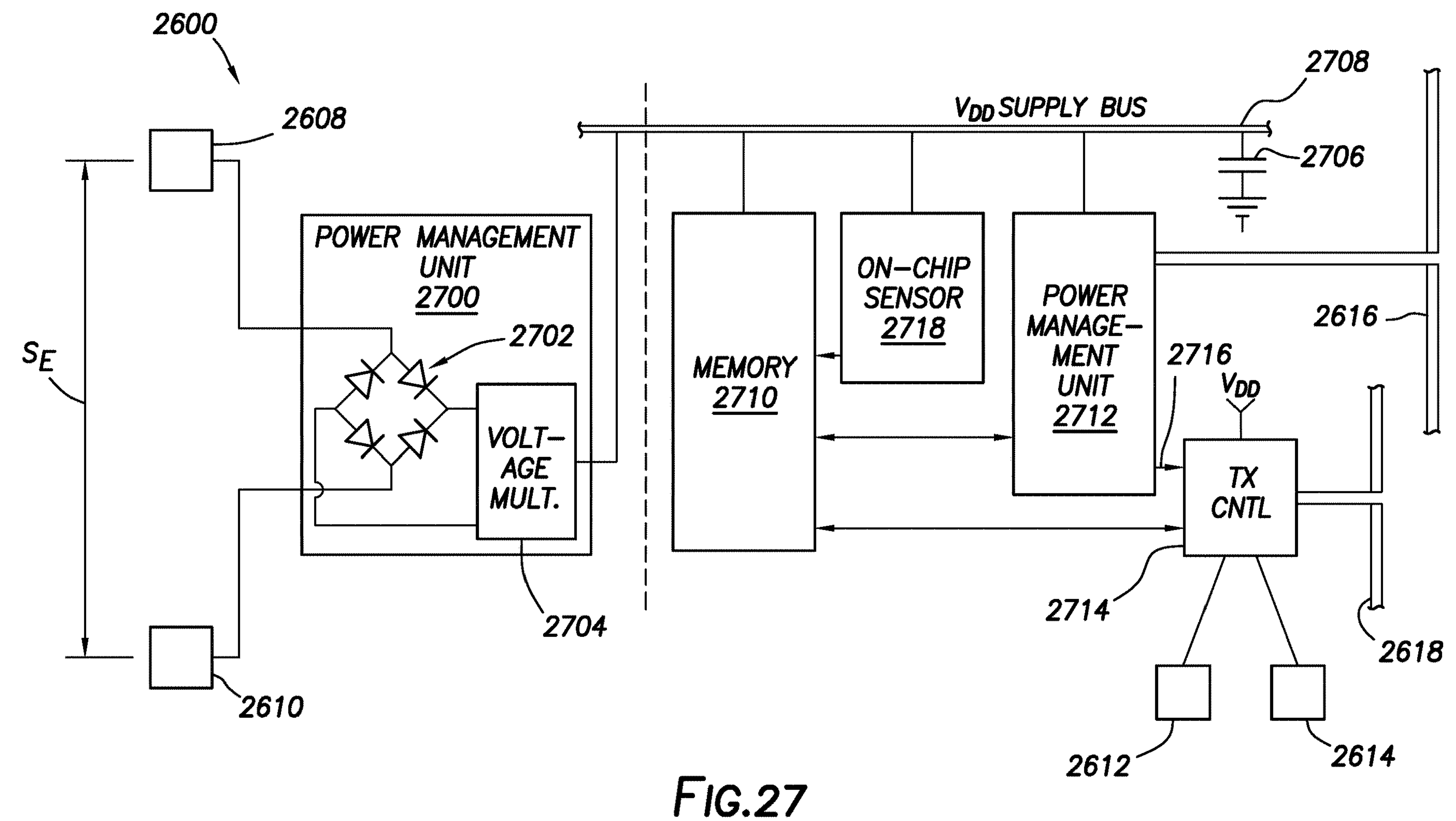
FIG. 27 shows, in block diagram form, various electrical components of an RFID chip in accordance with at least some embodiments.

FIG. 27 shows, in block diagram form, various electrical components of an RFID chip 2600 in accordance with at least some embodiments. In particular, all the components that are discussed with respect to FIG. 27 are created on and thus defined on the substrate 2602 (FIG. 26). The RFID chip 2600 comprises a power management unit 2700. The power management unit 2700 electrically coupled to electrode 2608 and electrode 2610. The power management unit 2700 produces energy based on interaction of the electrodes 2608 and 2610 with an electric field in, around, and permeating the RFID chip 2600. As discussed above, the energy extraction may be based on a capacitive coupling in non-conductive environments, or may be based on an electric current in conductive environments. From the perspective of the power management unit 2700 the extraction technique is conceptually the same, though a power management unit 2700 designed for operation in a capacitive coupling environment may not necessarily be operational in a conductive environment, and vice-versa.

The energy extracted across the electrodes 2608 and 2610 is applied to a rectifier 2702, the rectifier 2702 being part of the power management unit 2700. FIG. 27 shows the rectifier 2702 as a full-wave rectifier, but half-wave rectification may be operational (with less extraction efficiency). While the full-wave rectification is shown to be implemented with diodes, diode drop may limit the suitability of the use of diodes in the rectification, and thus the switching may be implemented by field effect transistors (FETs) to increase efficiency. In some cases, and as shown, the voltage produced by rectification may be supplied to a voltage multiplier 2704. The voltage multiplier 2704 may take any suitable form, such as Dickson Charge Pump (the Dickson Charge Pump fed the rectified DC signal and clock signals). Regardless of the precise design of the power management unit 2700, the power management unit 2700 provides power to the storage capacitor 2706, and other components, by way of the $V_{DD}$ supply bus 2708. It is estimated that a power of about 1 microwatt can be extracted from an electric field of about 1 V/m at 1 kHz for an RFID chip largest dimension of about 1 mm (i.e., an electrode spacing $S_E$ of about 1 mm).

Still referring to FIG. 27, the example RFID chip 2600 further comprises a memory 2710 configured to store data, and the memory 2710 is nonvolatile in the sense that data values written therein remain even after all the stored energy of the RFID chip 2600 has been depleted. The example RFID chip 2600 further comprises the power antenna 2616. The power antenna 2616 is electrically coupled to a second power management unit 2712. The power management unit 2712 receives the electromagnetic energy received by the power antenna 2616, harvests the energy, and stores the energy to storage capacitor 2706 coupled to the power management unit 2712 by way of the $V_{DD}$ supply bus 2708. The power management unit 2712 also decodes any encoded data “riding” the electromagnetic signal received by the power antenna 2616, and in the presence of the predetermined encoded data, the power management unit 2712 also triggers various other components to broadcast data. That is, the power management unit 2712 is electrically coupled to both the memory 2710 and the transmission controller 2714 (labeled “TX CNT'L” in the figure, and discussed more below), and thus the power management unit 2712, upon a command received through the power antenna 2616, triggers a broadcast of data using the transmission antenna 2618.

Again, the example RFID chip 2600 further comprises the transmission antenna 2618. The transmission antenna 2618 is electrically coupled to a transmission controller 2714. The transmission controller 2714, in turn, is electrically coupled to the $V_{DD}$ supply bus 2708, the memory 2710, and an enable signal 2716 of the power management unit 2712. The transmission controller 2714, when enabled by the power management unit 2712, reads the data from the memory 2710, and broadcasts the data to the RFID reader (e.g., reader 2018 (FIG. 20)) by way of the transmission antenna 2618. As discussed above, the transmission controller 2714 and transmission antenna 2618 in example systems are designed and constructed to transmit electromagnetic waves at frequency different than the frequency at which the power antenna 2616 harvests energy from electromagnetic waves. For example, in some cases the power antenna 2616 harvests energy at about 2.45 GHz, while the transmission antenna 2618 (as driven by the transmission controller 2714) broadcasts about 1.2 GHz. Other charging frequencies and broadcast frequencies may be used, but in most cases the charging and broadcast frequencies are 1 MHz and above, and in many cases above 1 GHz.

The example transmission controller 2714 also electrically couples to the electrodes 2612 and 2614. Thus, in addition to or in place of transmission of the data (e.g., values indicative of a physical parameter sensed by the RFID chip) using electromagnetic waves by way of the transmission antenna 2618, in conductive environments the transmission controller 2714 may transmit a value indicative of the parameter by inducing electrical current across the electrodes 2612 and 2614. Other example RFID chips 2600 implement a single set of electrodes (e.g., electrodes 2608 and 2610), and in such cases the transmission controller 2714 may work together with the power management unit 2700 to cease extraction of energy by the electrodes 2608 and 2610 (e.g., by opening the transistors implementing the rectifier 2702), coupling the transmission controller 2714 to the electrodes 2608 and 2610, and then inducing the electrical current flow between the electrodes 2608 and 2610 by the transmission controller 2714. Thereafter, the transmission controller 2714 may electrically disconnect from the electrodes 2608 and 2610, and the extraction of energy by way of the electrodes 2608 and 2610 may resume by the power management unit 2700. Parasitic creation of electromagnetic waves when inducing electrical current across electrodes 2612 and 2614 (or 2608 and 2610) for purposes of communication through the conductive environment shall not be considered to be a broadcast of electromagnetic waves.

Finally with respect to FIG. 27, the example RFID chip 2600 comprises an on-chip sensor 2718. The on-chip sensor 2718 electrically couples to the $V_{DD}$ supply bus 2708 and draws power therefrom. Depending on the nature of the on-chip sensor 2718, additional supply and/or reference voltages may be needed, and in such cases the power management unit 2700 or the power management unit 2712 may supply such voltages. The on-chip sensor 2718 also electrically couples to the memory 2710. Thus, when powered and activated, the on-chip sensor 2718 reads a physical parameter proximate to the RFID chip 2600, and provides the data to the memory 2710 for storage and later broadcast by the transmission controller 2714. The various physical parameters that the on-chip sensor 2718 may be constructed to read are discussed above.

The example RFID chips 2600 may implement on-chip sensors 2718 taking any of a variety of forms. Temperature sensing, however, may be a power intensive operation. For example, temperature measurement may be implemented in CMOS structures in the form of an electro-thermal filter (ETF) system; however, ETF systems utilize on-chip resistive heating elements to create heat pulses that are incident upon a thermocouple, and voltage differences as between pre- and post-application of the heat pulses can be used to determine ambient temperature of the substrate. ETF systems may be implemented in the on-chip sensor 2718 in situations where sufficient energy can be harvested. Other, possibly lower power, temperature sensing may be used as well. For example, temperature sensing may be implemented based on predetermined operational characteristics as a function of temperature of bipolar-junction transistors (BJT).

Figure 28:
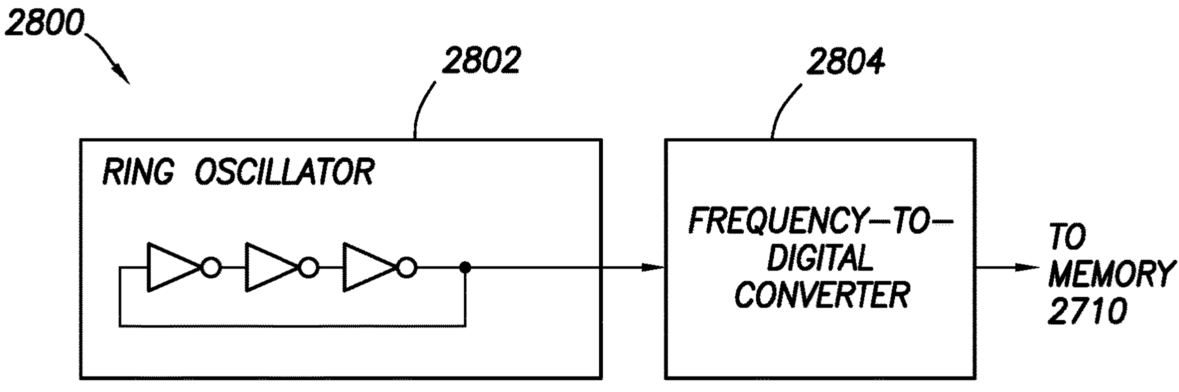
FIG. 28 shows a temperature sensor in accordance with at least some embodiments.

In accordance with other embodiments, a low power temperature measurement system is implemented by the on-chip sensor 2718 in the form of a temperature dependent ring oscillator. In particular, FIG. 28 shows a temperature sensor 2800 in accordance with example embodiments, where the temperature sensor 2800 may be implemented alone or with other sensors as part of the on-chip sensor 2718. The example temperature sensor 2800 comprises a ring oscillator 2802 electrically coupled to a frequency-to-digital (FD) converter 2804 (e.g., a ripple counter). The FD converter 2804 is electrically coupled to the memory 2710 (FIG. 27). The ring oscillator 2802 is illustratively shown as three NOT gates coupled in series, with a feedback path. Having three NOT gates is merely an example, and any odd number of gates may be used depending on the desired frequency of oscillation. The frequency of oscillation of the ring oscillator 2802 is a function of the combined gate delays through the gates. Gate delay is dependent upon the temperature of the silicon in which the various gates are created, with the gate delays shorter when the devices are cool (i.e., frequency of oscillation is higher), and gate delays longer when the devices are hot (i.e., frequency of oscillation is lower). The low power temperature measurement in accordance with example embodiments takes advantage of the oscillation frequency temperature dependence. That is, the ring oscillator 2802 couples to the FD converter 2804, which produces a digital output proportional to the frequency of oscillation of the ring oscillator 2802. Thus, as the temperature of the environment in which the RFID device increases, the temperature of the RFID chip increases, and the frequency of oscillation of the ring oscillator 2802 changes. The changes in oscillation frequency are captured by the output value of the FD converter 2804, which output is stored in the memory 2710. Thus, the temperature of the RFID chip, and thus the temperature of the surrounding environment, may be determined (either on the RFID device itself, or by later analysis of the data from the FD converter 2804). The temperature sensor 2800 is estimated to consume less than 100 nanoWatts in operation at 250 degrees Celsius.

Figure 29:
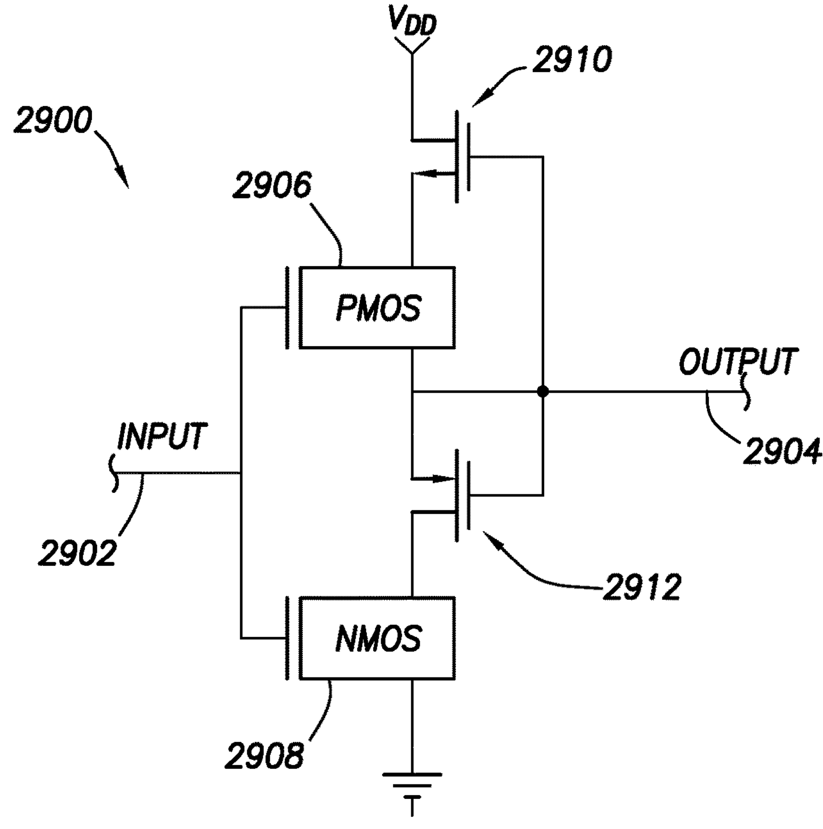
FIG. 29 shows an electrical circuit diagram of a NOT gate in accordance with at least some embodiments.

FIG. 29 shows an electrical circuit diagram of a NOT gate in accordance with at least some embodiments. In particular, NOT gate 2900 comprises an input port 2902 and an output port 2904. The input port 2902 couples to the gate of a p-channel metal oxide semiconductor field-effect transistor (MOSFET) 2906 (hereafter just PMOS FET 2906), and the input port 2902 also couples to the gate of an n-channel MOSFET 2908 (hereafter just NMOS FET 2908). The output port 2904 couples to the drain of the PMOS FET 2906 and the drain of the NMOS FET 2908. The example NOT gate further comprises a first feedback field effect transistor (FET) 2910 in the form of a p-channel FET with its drain coupled to $V_{DD}$, its source coupled to the PMOS FET 2906, and its gate coupled to the output port 2904. The example NOT gate further comprises a second feedback FET 2912 in the form of an n-channel FET with its source coupled to the drain of the PMOS FET 2906 and output port 2904, its drain coupled to the drain of the NMOS FET 2908, and its gate coupled to the output port 2904.

The PMOS FET 2906 and NMOS FET 2908 work together to create the inverting operation of the NOT gate 2900. However, in the absence of the feedback FETs 2910 and 2912 there is a fleeting but non-zero period of time in the transition between state changes of the output port 2904 that the FETs 2906 and 2908 short the $V_{DD}$ to ground, which consumes and wastes energy. In order to reduce the overall power consumption of the NOT gate (and thus the ring oscillator 2802 and any other device of the RFID chip 2600), the feedback FETs 2910 and 2912 work to reduce the temporary short through the FETs 2906 and 2908. In particular, when the input port 2902 of the NOT gate 2900 is at a low voltage, feedback FET 2910 is conducting drain-to-source to enable the PMOS FET 2906 to apply $V_{DD}$ to the output port, and feedback FET 2912 is open (as is NMOS FET 2908). When the input port 2902 transitions to a high voltage, the states of the PMOS FET 2906 and NMOS FET 2908 transition to opposite states. During the period of time when otherwise a temporary short would exist, the feedback FET 2912 is still non-conductive source-to-drain, thus blocking the temporary short. As the output port 2904 bleeds down, the feedback FET 2912 eventually becomes conductive (thus pulling the output port 2904 to ground through the feedback FET 2912 and NMOS FET 2908) and the feedback FET 2910 becomes non-conductive. In the opposite transition of the input port (from a high voltage to a low voltage), during the period of time when otherwise a temporary short would exist, the feedback FET 2910 is still non-conductive drain-to-source, thus blocking the temporary short.

Figure 30:
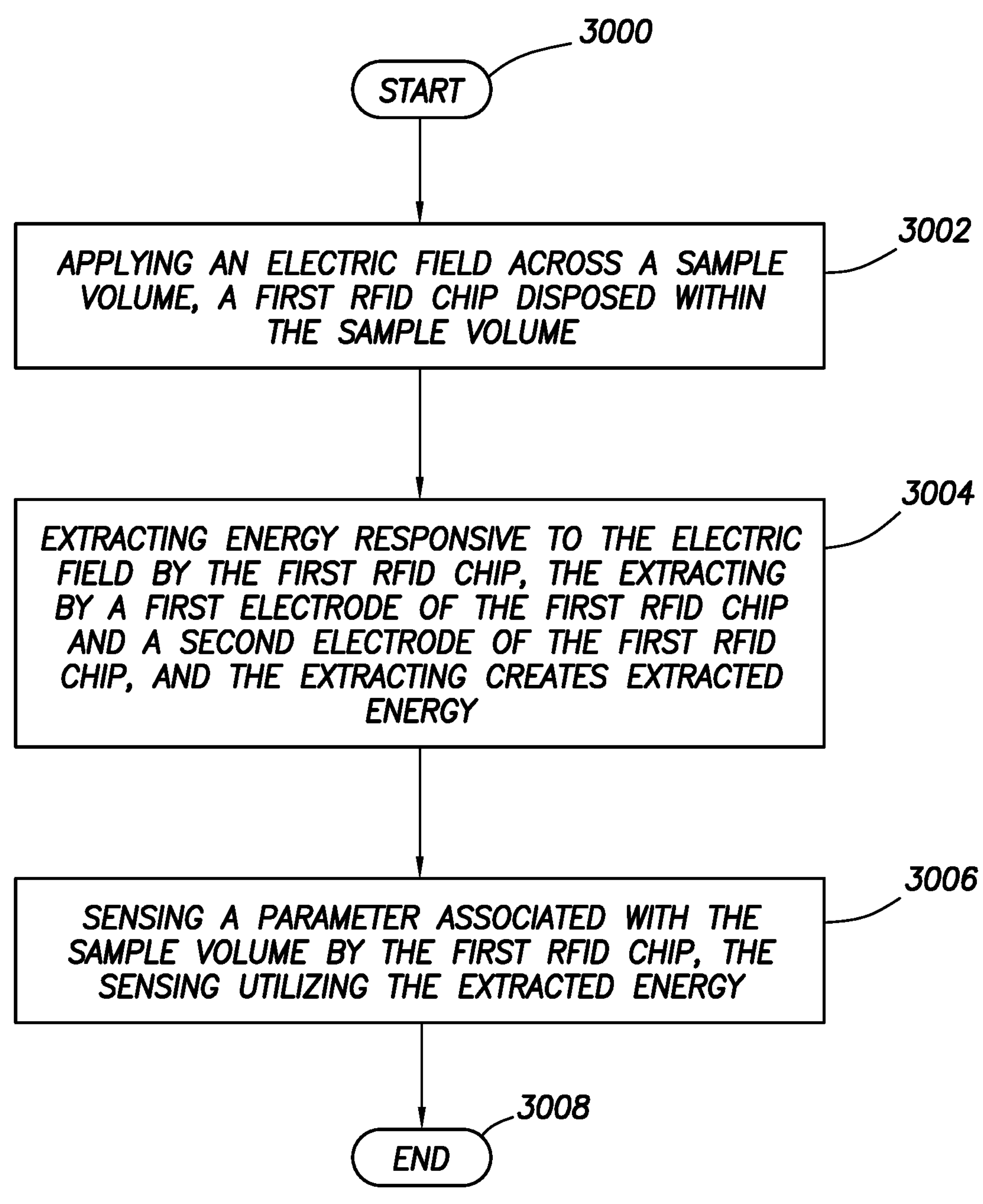
FIG. 30 shows a method in accordance with at least some embodiments.

FIG. 30 shows a method in accordance with at least some embodiments. In particular, the method starts (block 3000) and comprises: applying an electric field across a sample volume, a first RFID chip disposed within the sample volume (block 3002); extracting energy responsive to the electric field by the first RFID chip, the extracting by a first electrode of the first RFID chip and a second electrode of the first RFID chip, and the extracting creates extracted energy (block 3004); and sensing a parameter associated with the sample volume by the first RFID chip, the sensing utilizing the extracted energy (block 3006). Thereafter, the method ends (block 3008), likely to be immediately restarted.

The above discussion regarding energy harvesting related to electric fields applied to a sample volume is meant to be illustrative of the principles and various embodiments. Numerous variations and modifications will become apparent to those skilled in the art once the above disclosure is fully appreciated. It is intended that the following claims be interpreted to embrace all such variations and modifications.

What is claimed is:

1. A passive optoelectronic device on a substrate, the passive optoelectronic device comprising:

a photodetector configured to receive ambient optical energy incident upon the photodetector and convert the ambient optical energy into electrical energy at a first voltage, the ambient optical energy having a wavelength of less than 1.2 microns;

a voltage regulator electrically coupled to the photodetector, wherein the voltage regulator is configured to convert the electrical energy to a second voltage different than the first voltage;

a sensor electrically coupled to the voltage regulator and powered by the electrical energy, wherein the sensor is configured to create sensor data;

a first waveguide that defines a first end, a second end, and a length between the first end and the second end, the first waveguide has an internal volume of silicon;

a first grating coupler optically coupled to the first end of the first waveguide, the first grating coupler having a plurality of ridges parallel to each other, and the ridges transverse to the length of the first waveguide;

a second grating coupler optically coupled to the second end of the first waveguide, the second grating coupler having a plurality of ridges parallel to each other, and the ridges of the second grating coupler transverse to the length of the first waveguide;

a modulator electrically coupled to the voltage regulator, the modulator disposed between the first and second grating couplers, the modulator configured to modulate optical waves that propagate through the first waveguide, and towards the second grating coupler, using the electrical energy from the photodetector; and a driver circuit electrically coupled to the modulator, wherein the driver circuit configured to selectively change a state of the modulator responsive to the sensor data, wherein, the optical waves that propagate through the first waveguide, and towards the second grating coupler, are coupled out of the first waveguide into air or free space and transmitted to a reader device.

2. The passive optoelectronic device of claim 1, wherein the photodetector further comprises a photodiode configured to convert optical energy with a wavelength of about 850 nanometers into electrical energy at a first voltage.

3. The passive optoelectronic device of claim 2, wherein the photodetector further comprises at least one selected from a group comprising:

a photodiode exposed on an outer surface of the passive optoelectronic device;

a plurality of photodiodes connected in series and exposed on the outer surface of the passive optoelectronic device; and a photodiode optically coupled to the first waveguide.

4. The passive optoelectronic device of claim 1, wherein the modulator further comprises:

a first optical path having a first length and a second optical path having a second length, the second optical path distinct from the first optical path, and the first and second optical paths form a portion of the first waveguide;

a depletion region of a semiconductor junction disposed within the first optical path;

the first optical path electrically coupled to the driver circuit, wherein:

the first optical path and depletion region have a first state in which the first optical path induces a 180 degree phase shift in an optical wave that traverses the first optical path relative to an optical wave that simultaneously traverses the second optical path; and the first optical path and the depletion region have a second state in which the first optical path induces 90 degrees or less of phase shift in an optical wave that traverses the first optical path relative to an optical wave that simultaneously traverses the second optical path.

5. The passive optoelectronic device claim 1, wherein the modulator further comprises:

a second waveguide that defines a closed path with a length and a silicon internal volume;

a first region of the second waveguide evanescently coupled to the first waveguide;

a depletion region of a semiconductor junction disposed at a second region within the closed path of the second waveguide, the second region distinct from the first region, and the second region coupled to the driver circuit; and wherein the second waveguide and the depletion region are configured to selectively induce a phase shift in an optical wave that traverses the second waveguide.

6. The passive optoelectronic device of claim 1, wherein the modulator further comprises:

a second waveguide that defines a closed path with a length and has a silicon internal volume, a portion of the closed path of the second waveguide evanescently coupled to the first waveguide;

a first depletion region within the closed path of the second waveguide, the first depletion region electrically coupled to the driver circuit;

a third waveguide that defines a closed path with a length and has a silicon internal volume, a portion of the closed path of the third waveguide evanescently coupled to the first waveguide;

a second depletion region within the closed path of the second waveguide, the second depletion region electrically coupled to the driver circuit;

a fourth waveguide that defines a closed path with a length and has a silicon internal volume, a portion of the closed path of the fourth waveguide evanescently coupled to the first waveguide;

a third depletion region within the closed path of the fourth waveguide, the third depletion region electrically coupled to the driver circuit;

wherein the first, second and third depletion regions are each configured to selectively induce a phase shift in optical waves that traverse the second, third, and fourth waveguides, respectively; and the length of the second waveguide is shorter than the length of the third waveguide, and the length of the third waveguide is shorter than the length of the fourth waveguide.

7. The passive optoelectronic device of claim 1, wherein the sensor is configured to sense a physical parameter in proximity of the passive optoelectronic device, and to create the sensor data responsive to the physical parameter.

8. The passive optoelectronic device of claim 7, further comprising:

the sensor configured to sense the physical parameter being at least one selected from a group comprising:

electrical current through the passive optoelectronic device;

electric field in the area of the passive optoelectronic device;

pressure proximate the passive optoelectronic device;

temperature proximate the passive optoelectronic device; and movement of the passive optoelectronic device.

9. The passive optoelectronic device of claim 1, further comprising that the passive optoelectronic device defines:

a length of 100 microns or less;

a width of 100 microns or less; and a thickness of 100 microns or less.

10. The passive optoelectronic device of claim 1, further comprising that the passive optoelectronic device defines:

a length of 100 microns or less measured parallel to the first waveguide;

a width of 100 microns or less measured perpendicular to the length and parallel to the substrate; and a thickness of 400 microns or less measured perpendicular to the substrate.

11. A method comprising:

receiving a light by a photodetector exposed on an outer surface of a passive optoelectronic device;

generating an electrical current from the light;

powering a sensor from the electrical current, the sensor creates sensor data based on the electrical current; and wirelessly transmitting the sensor data from the passive optoelectronic device to a receiving device remote from the passive optoelectronic device, wherein the wirelessly transmitting comprises:

receiving a first infrared light by an optical coupler defined on the passive optoelectronic device;

coupling the first infrared light to a first waveguide of the passive optoelectronic device, and propagating the first infrared light along a first portion of the first waveguide; and then modulating the first infrared light responsive to data to create modulated infrared light;

propagating the modulated infrared light along a second portion of the first waveguide distinct from the first portion; and coupling the modulated infrared light out of the first waveguide and towards the receiving device.

12. The method of claim 11, wherein receiving the light further comprises receiving the light having a wavelength being at least one selected from a group comprising:

less than 1.2 microns;

less than 1.0 microns; and 850 nanometers.

13. The method of claim 11, wherein:

the light has a wavelength of 1.0 micron or less; and the first infrared light has a wavelength of 1.2 microns or greater.

14. The method of claim 11:

wherein coupling the first infrared light to the first waveguide further comprising coupling by way of a first optical coupler that comprises a first grating structure; and wherein coupling the modulated infrared light toward out of the first waveguide further comprising coupling by way of a second optical coupler that comprises a second grating structure.

15. The method of claim 11, wherein the modulating the first infrared light further comprises modulating by way of a Mach-Zehnder modulator disposed within an optical path of the first waveguide.

16. The method of claim 11, wherein the modulating the first infrared light further comprises modulating by way of an optical ring modulator having a first closed path.

17. The method of claim 16, wherein the modulating by way of the optical ring modulator further comprises modulating by way of the optical ring modulator having a plurality of closed paths.

18. The method of claim 11, further comprises sensing at least one selected from the group consisting of:

electrical current through the passive optoelectronic device;

pressure proximate to the passive optoelectronic device;

temperature proximate to the passive optoelectronic device; and movement of the passive optoelectronic device.

* * * * *